(12) United States Patent
Rudnicki et al.

(10) Patent No.: US 10,071,138 B2
(45) Date of Patent: Sep. 11, 2018

(54) COMPOSITIONS AND METHODS FOR MODULATING STEM CELLS AND USES THEREOF

(71) Applicant: Ottawa Hospital Research Institute, Ottawa (CA)

(72) Inventors: Michael A. Rudnicki, Ottawa (CA); Fabien Le Grand, Cachan (FR)

(73) Assignee: Ottawa Hospital Research Institute, Ottawa (CA)

( * ) Notice: Subject to any disclaimer, the term of this patent is extended or adjusted under 35 U.S.C. 154(b) by 0 days.

(21) Appl. No.: 15/241,523

(22) Filed: Aug. 19, 2016

(65) Prior Publication Data
US 2017/0042973 A1 Feb. 16, 2017

Related U.S. Application Data

(63) Continuation of application No. 13/266,428, filed as application No. PCT/CA2010/000601 on Apr. 27, 2010.

(60) Provisional application No. 61/172,832, filed on Apr. 27, 2009.

(51) Int. Cl.
| | |
|---|---|
| A61K 35/34 | (2015.01) |
| A61K 38/17 | (2006.01) |
| C07K 14/475 | (2006.01) |
| C07K 14/47 | (2006.01) |
| C12N 5/077 | (2010.01) |
| A61K 38/18 | (2006.01) |
| A61K 48/00 | (2006.01) |
| C12N 5/0797 | (2010.01) |
| C12N 15/11 | (2006.01) |
| C12N 15/113 | (2010.01) |
| G01N 33/50 | (2006.01) |
| A61K 35/545 | (2015.01) |

(52) U.S. Cl.
CPC ............ *A61K 38/18* (2013.01); *A61K 35/545* (2013.01); *A61K 38/1709* (2013.01); *A61K 48/005* (2013.01); *C07K 14/4702* (2013.01); *C12N 5/0623* (2013.01); *C12N 5/0658* (2013.01); *C12N 5/0659* (2013.01); *C12N 15/111* (2013.01); *C12N 15/113* (2013.01); *G01N 33/5073* (2013.01); *A61K 35/34* (2013.01); *C12N 2310/14* (2013.01); *C12N 2501/415* (2013.01); *C12N 2800/107* (2013.01)

(58) Field of Classification Search
None
See application file for complete search history.

(56) References Cited

U.S. PATENT DOCUMENTS

| | | | |
|---|---|---|---|
| 4,544,752 A | 10/1985 | Beck et al. | |
| 4,751,180 A | 6/1988 | Cousens et al. | |
| 4,935,233 A | 6/1990 | Bell et al. | |
| 5,679,647 A | 10/1997 | Carson et al. | |
| 5,739,118 A | 4/1998 | Carrano et al. | |
| 5,837,533 A | 11/1998 | Boutin | |
| 6,297,030 B1 | 10/2001 | Barnes et al. | |
| 6,337,184 B1 | 1/2002 | Miller | |
| 6,590,075 B2 | 7/2003 | Ruben et al. | |
| 7,153,832 B2 | 12/2006 | Nusse et al. | |
| 7,335,643 B2 | 2/2008 | Nusse et al. | |
| 7,541,183 B2 | 6/2009 | Rudnicki et al. | |
| 9,732,130 B2 | 8/2017 | Rudnicki et al. | |
| 2004/0005579 A1 | 1/2004 | Birse et al. | |
| 2005/0130181 A1 | 6/2005 | McSwiggen | |
| 2006/0171931 A1 | 8/2006 | Rudnicki et al. | |
| 2008/0226707 A1 | 9/2008 | Helms et al. | |
| 2008/0299135 A1 | 12/2008 | Zou | |
| 2009/0074777 A1 | 3/2009 | Wands et al. | |
| 2011/0319337 A1 | 12/2011 | Bravo et al. | |
| 2012/0213744 A1 | 8/2012 | Rudnicki et al. | |
| 2014/0142046 A1 | 5/2014 | Lee et al. | |
| 2014/0200179 A1 | 7/2014 | Garcia et al. | |
| 2015/0099708 A1 | 4/2015 | Lee et al. | |
| 2015/0111822 A1 | 4/2015 | Rudnicki et al. | |

FOREIGN PATENT DOCUMENTS

| | | |
|---|---|---|
| JP | 2006-509497 | 3/2006 |
| JP | 2007524611 | 8/2007 |
| JP | 2008511662 | 4/2008 |
| JP | 2010-520286 A | 6/2010 |
| JP | 2014-506568 A | 3/2014 |

(Continued)

OTHER PUBLICATIONS

Von Maltzahn et al., Nature Cell Biology, 14(2):186-191, 2012. WO.*
Alland, L. et al. "Dual myristylation and palmitylation of Src family member p59fyn affects subcellular localization", Journal of Biological Chemistry, 269:16701-16705 (1994).
Altschul et al., "Gapped BLAST and PSI-BLAST: a new generation of protein database search programs", Nucleic Acids Research, 25(17): 3389-402 (1997).
Amerongen, "Alternative Wnt Pathways and Receptors", Cold Spring Harbor Perspectives in Biology, 4(10): a007914, 18 pages (2012).
Anakwe et al., "Wnt signalling regulates myogenic differentiation in the developing avian wing", Development, 130(15): 3503-3514 (2003).

(Continued)

*Primary Examiner* — Marianne P Allen
(74) *Attorney, Agent, or Firm* — Weaver Austin Villeneuve & Sampson LLP

(57) ABSTRACT

There are provided compositions and methods for modulating stem cell division decisions, in particular, division symmetry. It has been demonstrated that wnt7a acts through frizzled-7 receptor expressed on the surface of adult stem cells, e.g. satellite stem cells, to activate the planar cell polarity (PCP) pathway, thereby promoting symmetrical expansion of stem cells. The compositions and methods of the invention are useful, for example, in modulating stem cell division symmetry in vitro and in vivo, in replenishing and expanding the stem cell pool, and in promoting the formation, maintenance, repair and regeneration of tissue.

7 Claims, 29 Drawing Sheets

Specification includes a Sequence Listing.

(56) References Cited

FOREIGN PATENT DOCUMENTS

| WO | WO 1992/006180 | | 4/1992 |
|---|---|---|---|
| WO | WO 1992/022635 | | 12/1992 |
| WO | WO 1993/014188 | | 7/1993 |
| WO | WO 1993/020221 | | 10/1993 |
| WO | WO 2004/029229 A2 | | 4/2004 |
| WO | WO 2004/113513 | * | 12/2004 |
| WO | WO 2006/026652 | | 3/2006 |
| WO | WO 2006/072016 A2 | | 7/2006 |
| WO | WO 2007/059612 | * | 5/2007 |
| WO | WO 2008/109119 A2 | | 9/2008 |
| WO | WO 2010/014948 A1 | | 2/2010 |
| WO | WO 2010/078458 A1 | | 7/2010 |
| WO | WO 2010/124365 | | 11/2010 |
| WO | WO 2011/004911 | | 1/2011 |
| WO | WO 2011/088127 A1 | | 7/2011 |
| WO | WO 2012/097093 A2 | | 7/2012 |
| WO | WO 2012/103360 A2 | | 8/2012 |
| WO | WO 2013/040309 A2 | | 3/2013 |

OTHER PUBLICATIONS

Anastas, et al., "WNT signalling pathways as therapeutic targets in cancer," Nature Reviews Cancer, 13(1):11-26 (2012).
Bae et al., "Regulation of myoblast motility and fusion by the CXCR4-associated sialomucin, CD164," J Biol Chem, 283(13):8301-8309, 2008.
Bass et al., "Syndecan-4-dependent Rac1 regulation determines directional migration in response to the extracellular matrix", The Journal of Cell Biology, 177(3): 527-538 (2007).
Bazan, et al., "Structural architecture and functional evolution of Wnts," Dev Cell., 23(2): 227-232 (2012).
Bentzinger et al., "Extrinsic regulation of satellite cell specification", Stem Cell Res Ther, 1 (3): 27 (2010).
Bhanot, et al., "A new member of the frizzled family from *Drosophila* functions as a Wingless receptor," Nature, 382(6588):225-230 ( 1996).
Bird et al., "Single-chain antigen-binding proteins", Science, 242: 423-426 (1988).
Bodine et al., "Akt/mTOR pathway is a crucial regulator of skeletal muscle hypertrophy and can prevent muscle atrophy in vivo", Nature Cell Biology, 3: 1014-1019 (2001).
Bonnemann et al., "Beyond dystrophin: current progress in the muscular dystrophies," Curr. Opin. Ped., 8(5):569-582, 1997.
Borello et al., "The WnU~-catenin pathway regulates Gli-mediated Myf5 expression during somitogenesis," Development, 133:3723-3732, 2006.
Bosnakovski et al., "Prospective isolation of skeletal muscle stem cells with a Pax7 reporter", Stem Cells, 26(12): 3194-3204 (2008). Epub Sep. 18, 2008.
Bracket al., "A Temporal Switch from Notch to Wnt Signalling in Muscle Stem Cells is Necessary for Normal ~dult Myogenesis," Cell Stem Cell, 2:50-59, 2008.
Bradley, et al., "A soluble form of Wnt-1 protein with mitogenic activity on mammary epithelial cells," Mol Cell Biol, 15(8):4616-4622 (1995).
Brown, "Dystrophin-Associated Proteins and the Muscular Dystrophies," Annu. Rev. Med., 48:457-466, 1997.
Burrus et al., "Biochemical analysis of murine Wnt proteins reveals both shared and distinct properties", Exp Cell Res., 220(2): 363-373 (1995).
Canadian Patent Application No. 2,760,042, Office Action dated Feb. 19, 2016.
Cerletti et al., "Highly efficient, functional engraftment of skeletal muscle stem cells in dystrophic muscles," Cell, 134:37-47,2008.
Charge et al., "Aging-related satellite cell differentiation defect occurs prematurely after Ski-induced muscle hypertrophy," Am J Physiol Cell Physiol, 283:C1228-1241, 2002.
Charge et al., "Cellular and molecular regulation of muscle regeneration," Physiol Rev, 84:209-238., 2004.
Chaudhary et al., "A rapid method of cloning functional variable-region antibody genes in *Escherichia coli* as single-chain immunotoxins", Proc. Natl. Acad. Sci. U.S.A., 87: 1066-1070 (1990).
Chen et al., "Protein kinase A signalling via CREB controls myogenesis induced by Wnt proteins," Nature, ~33(7023):317-322, 2005.
Ching et al. "Lipid-independent Secretion of a *Drosophila* Wnt Protein", Journal of Biological Chemistry, 283(25): 17092-17098 (2008).
Ciciliot and Schiaffino, "Regeneration of mammalian skeletal muscle. Basic mechanisms and clinical implications", Current Pharmaceutical Design, 16(8): 906-914 (2010).
Ciruna et al., "Planar cell polarity signalling couples cell division and morphogenesis during neurulation," Nature 439:220-224. 2006.
Clevers, "WnU~-Catenin Signaling in Development and Disease," Cell127:469-480, 2006.
Collins et al., "Stem Cell Function, Self-Renewal, and Behavioral Heterogeneity of Cells from the Adult Muscle Satellite Cell Niche," Cell122, 289-301, 2005.
Cooper "Advances in membrane receptor screening and analysis," Journal of Molecular Recognition, 17(4):286-315 (2004).
Cornelison et al., "Essential and separable roles for Syndecan-3 and Syndecan-4 in skeletal muscle development and regeneration," Genes & Development, 18:2231-2236, 2004.
Cornelison et al., "Syndecan-3 and Syndecan-4 Specifically Mark Skeletal Muscle Satellite Cells and are Implicated in Satellite Cell Maintenance and Muscle Regeneration," Dev Biol, 239:79-94, 2001.
Cosgrove et al., "A home away from home: challenges and opportunities in engineering in vitro muscle satellite cell niches", Differentiation, 78(2-3): 185-194 (2009).
Cossu et al., "Wnt signaling and the activation of myogenesis in mammals," Embo J, 18, 6867-6872, 1999.
Couso, et al., "Notch is Required for wingless Signaling in the Epidermis of *Drosophila*," Cell, 79(2): 259-272 (1994).
Crise et al., "Identification of palmitoylation sites on CDR, the Human Immunodeficiency Virus receptor" Journal of Biological Chemistry 267: 13593-13597 (1992).
Daley et al., "A focal adhesion protein-based mechanochemical checkpoint regulates cleft progression during branching morphogenesis", Dev Dyn., 240(9): 2069-2083 (2011).
Daley et al., "Identification of a mechanochemical checkpoint and negative feedback loop regulating branching morphogenesis", Developmental Biology, 336(2):169-182 (2009). Epub Oct. 3, 2009.
Dann et al., "Insights into Wnt binding and signalling from the structures of two Frizzled cysteine-rich domains," Nature, 412:86-90, 2001.
Database EMBL [Online] "*Rattus norvegicus* (Norway rat) rCG56255", Aug. 9, 2005 (Aug. 9, 2005), NPL reference No. XP002734433: obtained on NCBI, NCBI Accession No. EDL91364.
Del Alamo and Miodzik, "Frizzled/PCP-Dependent Asymmetric Neuralized Expression Determines R3/R4 Fates in the *Drosophilia* Eye," Developmental Cell, 11:887-894, 2006.
Devos et al., "Human growth hormone and extracellular domain of its receptor: crystal structure of the complex", Science, 255:306-312 (1992).
Diatchenko et al., "Suppression subtractive hybridization: a method for generating differentially regulated or tissue-specific eDNA probes and libraries," Proc Nat/ Acad Sci USA, 93:6025-6030, 1997.
Dierick and Bejsovec, "Cellular Mechanisms of Wingless/Wnt Signal Transduction," Current Topics in Developmental Biology, 43:153-178, 1999.
Doubravska et al. "Fatty acid modification of Wnt1 and Wnt3a at serine is prerequisite for lipidation at cysteine and is essential for Wnt signalling", Cellular Signalling, 23(5): 837-848 (2011).
Egger-Adam et al., "Trimeric G protein-dependent signaling by Frizzled receptors in animal development," Front Biosci, 13:4 7 40-4 755, 2008.
EMBL Accession No. EDL91364, Aug. 9, 2005, XP-002934433, 1 page.

(56) References Cited

OTHER PUBLICATIONS

European Application No. 10769170.1, (Corrected) European Search Report dated May 27, 2013.
European Application No. 10769170.1, European Search Report dated Apr. 24, 2013.
European Application No. 10769170.1, Office Action dated Feb. 20, 2017.
European Application No. 10769170.1, Office Action dated May 18, 2016.
European Application No. 10769170.1, Office Action dated Sep. 3, 2015.
European Application No. 12734079.2, Extended European Search Report dated Apr. 2, 2015.
European Application No. 12734079.2, Partial European Search Report Dec. 4, 2014.
European Application No. 12738949.2, Extended European Search Report dated Jul. 4, 2014.
European Application No. 12831452.3, Extended European Search Report dated Dec. 23, 2014.
European Application No. 12831715.3, Extended European Search Report dated Feb. 9, 2015.
Fisher et al., "Molecular genetics of facioscapulohumeral muscular dystrophy (FSHD)," Neuromuscul. Disorders, 7(1):55-62, 1997.
Franch-Marro et al., "Wingless secretion requires endosome-to-Golgi retrieval of Wntless/Evi/Sprinter by the retromer complex", Nature Cell Biology, 1 0(2): 170-177 (2008). Published online: Jan. 13, 2008.
Fredriksson et al., "Protein detection using proximity-dependent DNA ligation assays", Nature Biotechnology, 20: 473-477 (2002).
Funakoshi et al., "Emerin and cardiomyopathy in Emery-Dreifuss muscular dystrophy," Neuromuscul. Disorders, 9(2): 1 08-114, 1999.
Galli and Burrus, "Differential Palmit(e)oylation of Wnt1 on C93 and S224 Residues Has Overlapping and Distinct Consequences", PLoS One, 6(10): e26636, pp. 1-17 (2011).
GenBank Accession No. NP 004616.
GenBank Accession No. P24383.
GenBank Accession No. P28047.
GenBank Accession No. PF6706.
Giles, et al., "Caught up in a Wnt storm: Wnt signaling in cancer," Biochim Biophys Acta, 1653(1):1-24 (2003).
Glass et al., "Signalling pathways that mediate skeletal muscle hypertrophy and atrophy", Nature Cell Biology, 5: 87-90 (2003).
Goto et al., "Planar Cell Polarity Genes Regulate Polarized Extracellular Matrix Deposition During Frog Gastrulation," Curr Bioi, 15:787-793, 2005.
Green et al., "Opposing Wnt pathways orient cell polarity during organogenesis," Nature, 134:646-656, 2008.
Gros et al., "WNT11 acts as a directional cue to organize the elongation of early muscle fibres," Nature, ~57:589-593, 2009.
Hall et al., "Axonal Remodeling and Synaptic Differentiation in the Cerebellum Is Regulated by WNT-7a SiQnalinQ," Cell, 100:525-535, 2000.
Hayman and Ruoslahti, "Distribution of fetal bovine serum fibronectin and endogenous rat cell fibronectin in extracellular matrix", The Journal of Cell Biology, 83(1): 255-259 (1979).
Henikoff and Henikoff, "Amino acid substitution matrices from protein blocks", Proc Natl Acad Sci USA, 89(22): 10915-10919 (1992).
Hirabayashi et al., "The WnU~-catenin pathway directs neuronal differentiation of cortical neural precursor cells," Development 131:2791-2801, 2004.
Hoffman et al., Characterization of dystrophin in muscle-biopsy specimens from patients with Duchenne's or Becker's muscular dystrophy, New England Journal of Medicine, 318:1363-1368, 1988.
Hoppler, et al., "Expression of a dominant-negative Wnt blocks induction of MyoD in Xenopus embryos," Genes & Development, 10(21):2805-2817 (1996).

Hruby, "Designing peptide receptor agonists and antagonists," Nature Reviews Drug Discovery, 1 (11):847-858 (2002).
Hsieh, et al., "Biochemical characterization of Wnt-Frizzled interactions using a soluble, biologically active vertebrate Wnt protein," Proceedings of the National Academy of Sciences, 96(7):3546-3551 (1999).
Huang et al., "Interference of tenascin-C with syndecan-4 binding to fibronectin blocks cell adhesion and stimulates tumor cell proliferation", Cancer Research, 61 (23): 8586-8594 (2001).
Huston et al., "Protein engineering of antibody binding sites: recovery of specific activity in an anti-digoxin single-chain Fv analogue produced in *Escherichia coli*", Proc. Natl. Acad. Sci. U.S.A., 85: 5879-5883 (1988).
Hynes and Yamada, "Fibronectins: Multifunctional Modular Glycoproteins", The Journal of Cell Biology, 95: 369-377 (1982).
Ingham, "Has the quest for a Wnt receptor finally frizzled out?," Trends Genet., 12(1 0)382-384 (1996).
Ishibashi et al, "MyoD induces myogenic differentiation through cooperation of its NH2- and COOH-terminal regions," J Cell Bioi, 171, 471-482, 2005.
Ishikawa et al., Seibutsugaku Jiten [Biology Dictionary], first print, Tokyo Kagaku Dojin K.K., (2010); Housekeeping gene (plants) (genes); A gene encoding a protein required for general functions of a cell, which is constitutively expressed (constitutive gene). (Japanese dictionary reference with English summary of relevant portion.).
Janda, et al., "Structural basis of Wnt Recognition by Frizzled," Science, 337(6090):59-64, (2012).
Kadowaki et al., "The segment polarity gene porcupine encodes a putative multitransmembrane protein involved in Wingless processing", Genes Development, 10:3116-3128 (1996).
Kengaku et al., "Distinct WNT Pathways Regulating AER Formation and Dorsoventral Polarity in the Chick Limb Bud," Science 280:1274-1277, 1998.
Kikuchi, et al., "Multiplicity of the interactions of Wnt proteins and their receptors," Cell Signal, 19(4):659-671 (2007).
Klaus, et al., "Wnt signalling and its impact on development and cancer," Nature Reviews Cancer, 8(5):387-398 (2008).
Koller and Smithies, "Inactivating the ~2-microglobulin locus in mouse embryonic stem cells by homologous recombination", Proc. Natl. Acad. Sci. USA, 86: 8932-8935 (1989).
Komekado, H. et al. "Giycosylation and palmitoylation of Wnt-3a are coupled to produce an active form of Wnt-3a", Genes to Cells, 12(4): 521-534 (2007).
Kuang et al., "Asymmetric self-renewal and commitment of satellite stem cells in muscle," Cell, 129(5):999-1010, 2007.
Kuang et al., "Distinct roles for Pax7 and Pax3 in adult regenerative myogenesis," J Cell Bioi, 172:103-113, 2006.
Kuang et al., "Niche Regulation of Muscle Satellite Cell Self-Renewal and Differentiation," Cell Stem Cell, 2:22-31' 2008.
Kurayoshi et al. "Post-translational palmitoylation and glycosylation of Wnt-5a are necessary for its signalling", Biochem J., 402(3): 515-523 (2007).
LeGrand et al., "Wnt7a activates the planar cell polarity pathway to drive the symmetric expansion of satellite stem cells," Cell Stem Cell, 4:535-547, 2009.
Lim and Campbell, "The sarcoglycan complex in limb-girdle muscular dystrophy," Curr. Opin. Neural., 11 (5):443-452, 1998.
Lim et al. "Direct Binding of Syndecan-4 Cytoplasmic Domain to the Catalytic Domain of Protein Kinase C (PKC alpha) Increases Focal Adhesion Localization of PKC alpha" JBC 278(16): 13795-13802 (2003).
Logan, et al., "The Wnt Signaling Pathway in Development and Disease," (2004) Annu Rev Cell Dev Biol 20:781-810 (2004).
Lyon et al., "Elucidation of the structural features of heparan sulfate important for interaction with the Hep-2 domain of fibronectin", The Journal of Biological Chemistry, 275(7): 4599-4606 (2000).
Lyu and Joo, "Wnt-7a Up-regulates Matrix Metalloproteinase-12 Expression and Promotes Cell Prliferation in Corneal Epithelial Cells during Sound Healing," The Journal of Biological Chemistry, 280(22):21653-21660, 2005.

(56) References Cited

OTHER PUBLICATIONS

Maltzahn et al., "A truncated Wnt7a retains full biological activity in skeletal muscle", Nature Communications, 4: 2869, 9 pages (2013).
Mara Tea et al., "Deletion and fusion analysis of the phage phi X174lysis gene E", Gene, 40: 39-46 (1985).
Mason et al., "Mutational analysis of mouse Wnt-1 identifies two temperature-sensitive alleles and attributes of Wnt-1 protein essential for transformation of a mammary cell line", Mol. Bioi. Cell, 3: 521-533 (1992).
Massie et al., "New adenovirus vectors for protein production and gene transfer", Cytotechnology, 28(1-3): 53-64 (1998).
Matthews et al., "Directional migration of neural crest cells in vivo is regulated by Syndecan-4/Rac1 and non-canonical Wnt siQnalinQ/RhoA," Development, 135:1771-1780, 2008.
McKinnell et al., "Pax7 activates myogenic genes by recruitment of a histone methyltransferase complex," Nat Cell Bioi, 1 0:77-84, 2008.
McMahon, "The Wnt family of developmental regulators," Trends Genet., 8(7):236-242 (1992).
Miller and Sassoon, "Wnt-7a maintains appropriate uterine patterning during the development of the mouse female reproductive tract," Development, 125:3201-3211, 1998.
Miller, "The Wnts," Genome Bioi., 3(1)reviews3001.1-3001.15 (2001).
Montarras et al., "Direct Isolation of Satellite Cells for Skeletal Muscle Regeneration," Science, 309:2064-2067,2005.
Montcouquiol et al., "Asymmetric localization ofVangl2 and Fz3 indicate novel mechanisms for planar cell polarity in mammals," J Neurosci, 26:5265-5275, 2006.
Montcouquiol et al., "Identification of Vangl2 and Scrb1 as planar polarity genes in mammals," Nature, ~23: 173-177' 2003.
Morrell, et al., "Liposomal Packaging Generates Wnt Protein with In Vivo Biological Activity," PLoS One, 3(8):e2930 (2008).
Munoz et al., "Syndecan-4 regulates non-canonical Wnt signalling and is essential for convergent and extension movements in Xenopus embryos," Nat Cell Bioi, 8:492-500, 2006.
Murakami et al., "Non-canonical fibroblast growth factor signalling in angiogenesis", Cardiovascular Research, 78: 223-231 (2008).
Murphy et al., "Genetic construction, expression, and melanoma-selective cytotoxicity of a diphtheria toxin-related alpha-melanocyte-stimulating hormone fusion protein", Proc. Natl. Acad. Sci. USA, 83: 8258-8262 (1986).
Nagaoka et al., "Cripto-1 enhances the canonical WnU~-catenin signaling pathway by binding to LRP5 and LRP6 co-receptors", Cell Signal, 25(1): 178-189 (2013). Published online Sep. 27, 2012. doi: 10.1 016/j.cellsig.2012.09.024.
Nusse, "Wnt signaling in disease and in development," Cell Research, 15(1):28-32 (2005).
Nusse, et al., "Many Tumors Induced by the Mouse Mammary Tumor Virus Contain a Provirus Integrated in the Same Region of the Host Genome," Cell, 31 (1):99-109 (1982).
Nusse, R., "Wnts and Hedgehogs: lipid-modified proteins and similarities in signaling mechanisms at the cell surface", Development, 130: 5297-5305 (2003).
O'Dowd et al., "Palmitoylation of the human beta 2 adrenergic receptor" Journal of Biological Chemistry 269:7564-7569 (1989).
Oustanina et al., "Pax7 directs postnatal renewal and propagation of myogenic satellite cells but not their specification," The EMBO Journal, 23:3430-3439, 2004.
Papkoff, et al., "Wnt-1 Regulates Free Pools of Catenins and Stabilizes APC-Catenin Complexes," Mol. Cell Biol., 16(5):2128-2134 (1996).
Park and Moon, "The planar cell-polarity gene stbm regulates cell behaviour and cell fate in vertebrate embryos," Nat Cell Bioi, 4:20-25, 2002.
PCT Application No. PCT/CA2010/000601, International Report on Patentability dated Nov. 10, 2011.
PCT Application No. PCT/CA2010/000601, International Search Report dated Jul. 22, 2010.

PCT Application No. PCT/CA2010/000601, Written Opinion dated Jul. 22, 2010.
PCT Application No. PCT/US2012/020984, International Preliminary Report on Patentability, dated Jul. 16, 2013.
PCT Application No. PCT/US2012/020984, International Search Report and Written Opinion, dated Jul. 30, 2012.
PCT Application No. PCT/US2012/022761, International Preliminary Report on Patentability dated Aug. 10, 2012, 6 pages.
PCT Application No. PCT/US2012/022761, International Search Report and Written Opinion dated Aug. 10, 2012, 10 pages.
PCT Application No. PCT/US2012/055336, International Preliminary Report on Patentability dated Mar. 18, 2014, 7 pages.
PCT Application No. PCT/US2012/055336, International Search Report and Written Opinion dated Feb. 25, 2013, 11 pages.
PCT Application No. PCT/US2012/055396, International Preliminary Report on Patentability dated Feb. 26, 2013, 14 pages.
PCT Application No. PCT/US2012/055396, International Search Report and Written Opinion dated Feb. 26, 2013, 14 pages.
Peifer et al., "Wingless signal and Zeste-white 3 kinase trigger opposing changes in the intracellular distribution of Armadillo," Development, 120(2):369-380 (1994).
Peters et al., "Fibronectin isoform distribution in the mouse. II. Differential distribution of the alternatively spliced EIIIB, Ell 1A, and V segments in the adult mouse", Cell Adhesion and Communication, 4(2):127-48 (1996).
Pisconti et al., "Syndecan-3 and Notch cooperate in regulating adult myogenesis", J Cell Bioi., 190(3): 427-441 (2010).
Polesska YA et al., "Wnt Signaling Induces the Myogenic Specification of Resident CD45+ Adult Stem Cells During Muscle Regeneration," Cell, 113(7):841-852, 2003.
Resh, M.A. "Fatty acylation of proteins: new insights into membrane targeting of myristoylated and palmitoylated proteins" Biochimica et Biophysica Acta 1451:1-16 (1999).
Rochat et al., "Insulin and wnt1 pathways cooperate to induce reserve cell activation in differentiation and myotube hypertrophy," Mol Bioi Cell, 15:4544-4555, 2004.
Sacco et al., "Self-renewal and expansion of single transplanted muscle stern cells," Nature, 56:502-506, 2008.
Seale et al., "Pax7 Is Required for the Specification of Myogenic Satellite Cells," Cell, 1 02(6):777-786, 2000.
Seifert et al., "Frizzled/PCP signalling: a conserved mechanism regulating cell polarity and directed motility," Nat Rev Genet, 8(2): 126-138, 2007.
Singh et al., "Assembly of fibronectin extracellular matrix", Annual Review of Cell and Developmental Biology, 26: 397-419 (2010).
Smith et al., "Human interleukin 4. The solution structure of a four-helix bundle protein", J. Mol. Bioi., 224:899-904 (1992).
Smolich et al., "Wnt family proteins are secreted and associated with the cell surface", Molecular Biology of the Cell, 4(12): 1267-1275 (1993).
Srinivas et al., "Cre reporter strains produced by targeted insertion of EYFP and ECFP into the ROSA26 locus," BMC Dev Bioi, 1:4, 2001.
Struewing, et al., "Mitochondrial and Nuclear Forms of Wnt13 Are Generated via Alternative Promoters, Alternative RNA Splicing, and Alternative Translation Start Sites," Journal of Biological Chemistry, 281(11):7282-7293 (2006).
Tajbakhsh et al., "Differential activation of Myf5 and MyoD by different Wnts in explants of mouse paraxial mesoderm and the later activation of myogenesis in the absence of Myf5," Development, 125:4155-4162, 1998.
Takada et al. "Monounsaturated Fatty Acid Modification of Wnt Protein: Its Role in Wnt Secretion", Developmental Cell, 11 (6): 791-801 (2006).
Tallquist et al., "Early myotome specification regulates PDGFA expression and axial skeleton development," Development 127:5059-5070, 2000.
Tanaka et al. "*Drosophila* segment polarity gene product porcupine stimulates the posttranslational N-glycosylation of wingless in the endoplasmic reticulum", J. Bioi. Chem., 277: 12816-12823 (2002).
Torban et al., "Genetic interaction between members of the Vangl family causes neural tube defects in mice," Proc Nat/ A cad Sci US A, 105:3449-3454, 2008.

(56) References Cited

OTHER PUBLICATIONS

Torban et al., "Van Gogh-like2 (Strabismus) and its role in planar cell polarity and convergent extension in vertebrates," Trends Genet, 20(11):570-577, 2004.
Torrente et al., "Human circulating AC133(+) stem cells restore dystrophin expression and ameliorate ~unction in dystrophic skeletal muscle," J Clin Invest, 114:182-195, 2004.
U.S. Appl. No. 13/266,428, Restriction Requirement dated Feb. 15, 2013.
U.S. Appl. No. 13/266,428, Office Action dated Apr. 19, 2016.
U.S. Appl. No. 13/266,428, Office Action dated Feb. 15, 2013.
U.S. Appl. No. 13/266,428, Office Action dated Jun. 30, 2014.
U.S. Appl. No. 13/266,428, Office Action dated Jun. 9, 2015.
U.S. Appl. No. 13/266,428, Office Action dated Nov. 12, 2015.
U.S. Appl. No. 13/266,428, Office Action dated Oct. 15, 2013.
U.S. Appl. No. 13/979,368, Office Action dated Oct. 6, 2015.
U.S. Appl. No. 13/982,184, Office Action dated Jan. 4, 2016.
U.S. Appl. No. 13/982,184, Office Action dated Jun. 11, 2015.
U.S. Appl. No. 14/344,309, Office Action dated Mar. 17, 2016.
U.S. Appl. No. 14/344,309, Notice of Allowance dated Apr. 27, 2017.
U.S. Appl. No. 14/344,310, Office Action dated Dec. 30, 2015.
Uhlman and Peyman, "Antisense Oligonucleotides: A New Therapeutic Principle", Chemical Reviews, 90(4): 544-584 (1990).
Van Den Heuvel et al., "Mutations in the segment polarity genes wingless and porcupine impair secretion of the wingless protein", 12(13): 5293-5302 (1993).
Van Leeuwen, et al., "Biological activity of soluble wingless protein in cultured *Drosophila imaginal* disc cells," Nature, 368(6469):342-344 (1994).
Veeman, et al., "A Second Canon: Functions and Mechanisms of Beta-Catenin-lndependent Wnt Signaling," Dev. Cell5(3):367-377 (2003).
Voit, "Congenital muscular dystrophies: 1997 update," Brain Dev.,20(2):65-74, 1998.
Wang, et al., "Wnt7b Activates Canonical Signaling in Epithelial and Vascular Smooth Muscle Cells through Interactions with Fzd1, Fzd10, and LRP5," Mol Cell Biol., 25(12): 5022-5030 (2005).
Willert et al., "Wnt Proteins are lipid-modified and can act as stem cell growth factors", Nature, 423(6938):448-452 (2003).
Wodarz, "Mechanisms of Wnt Signalling in Development," Annu. Rev. Cell Dev. Bioi., 14:59-88, 1998.
Woods et al., "Syndecan-4 binding to the high affinity heparin-binding domain of fibronectin drives focal adhesion formation in fibroblasts", Archives of Biochemistry and Biophysics, 374(1):66-72 (2000).
Worton, "Muscular dystrophies: diseases of the dystrophin-glycoprotein complex," Science, 270:755-756, 1995.
Xian et al. "Syndecans as receptors and organizers of the extracellular matrix", Cell and Tissue Research, 339(1): 31-46 (2010).
Yamanaka et al., "Wnt11 stimulation induces polarized accumulation of dishevelled at apical adherens junctions through Frizzled 7 ," Genes to Cells Devoted to Molecular & Cellular Mechanisms, 12:961-967, 2007.
Yang-Snyder, et al., "A frizzled homolog functions in a vertebrate Wnt signaling pathway," Curr Biol., 6(1 0): 1302-1306 (1996).
Zallen, "Planar Polarity and Tissue Morphogenesis," Cell, 129(6):1 051-1063, 2007.
Zhai et al., "*Drosophila* Wnt-1 Undergoes a Hydrophobic Modification and Is Targeted to Lipid Rafts, a Process That Requires Porcupine", The Journal of Biological Chemistry, 279(32): 33220-33227 (2004).
Zhao, et al., "Controlling the In Vivo Activity of Wnt Liposomes," Methods Enzymol, 465:331-347 (2009).
Zilstra et al., "Germ-line transmission of a disrupted ~2microglobulin gene produced by homologous recombination in embryonic stem cells", Nature, 342: 435-438 (1989).
Zusinaite et al., "Mutations at the palmitoylation site of non-structural protein nsP1 of Semliki Forest virus attenuate virus replication and cause accumulation of compensatory mutations" Journal of General Virology 88: 1977-1985 (2007).

\* cited by examiner

Satellite Stem Cells Express the Wnt receptor Frizzled7

Wnt7a-Frizzled7 Signaling Drives Satellite Stem Cell Expansion

PCP Components are Expressed by Myogenic Cells

Vangl2 is Required for Symmetric Expansion of Satellite Stem Cells

Ectopic Wnt7a Enhances Muscle Regeneration

Wnt7a Drives Satellite Stem Cell Expansion

FACS purification of muscle satellite cells.

YFP⁻ satellite cell-derived myoblasts do not express Myf5 protein.

Wnt7a do not induce stabilization and nuclear localization of ß-Catenin in activated muscle satellite cells.

Wnt7a increase satellite stem cell self-renewal while not modifying satellite cells' proliferation kinetics.

Efficient electroporation of plasmids in the adult TA muscle.

Wnt7a does not effect myogenic proliferation or differentiation.

Electroporation of Wnt7a cDNA into the TA muscle of adult wt mice leads to an increase in satellite cell numbers

Number of satellite cells in mdx mice after electroporation with a Wnt7a-containing plasmid

Electroporation of Wnt7a containing plasmid increases fiber diameter in mdx and wt mice Administration of Wnt7a recombinant protein produces effects similar to electroporation of a Wnt7a plasmid > AK004683 | Mus musculus Wnt7a cDNA sequence
GGCAGTCCCCGCGCCTCAAACACTTGCCGCGATCGCTGGCGCGCAGCGGCGCCCCTTGTTGCGCTTGTTC
TCCCCTCCTCTGGCTCCGCGGCTCCCGCGCTCTGGGACAGTCTCCAGTGCCTAGCGCGGACCGACGCACC
GACGGACCGCCCAGGGAGCCTCGGCCCGCGCCCCTGCGCAGGCTATGTGGATTGCCCCGCCGGGCCCGG
CTGGCGGGATCAGCACAGCCCGGCCCGTGGCACCCGCCACCAGCGGGGACTATGACCCGGAAAGCGCGGC
GCTGCCTGGGCCACCTCTTTCTCAGCCTGGGCATAGTCTACCTCCGGATCGGTGGCTTCTCTTCGGTGGT
AGCTCTGGGTGCGAGCATCATCTGTAACAAGATCCCAGGCCTGGCTCCAGACAGCGGGCAATCTGCCAG
AGCCGGCCGGACGCCATCATCGTCATAGGAGAAGGCTCCCAAATGGGCCTGGACGAGTGTCAGTTTCAGT
TCCGAAATGGCCGTTGGAACTGCTCAGCGCTGGGAGAGCGTACTGTCTTCGGGAAGGAGCTCAAAGTGGG
GAGTCGGGAGGCTGCCTTCACCTATGCGATTATCGCTGCGGGCGTGGCCCATGCCATCACTGCTGCCTGC
ACCCAGGGCAACCTGAGCGACTGTGGCTGCGACAAGGAGAAGCAAGGCCAGTACCACCGGGACGAGGGCT
GGAAGTGGGGTGGCTGCTCTGCCGACATCCGCTACGGCATCGGCTTCGCCAAGGTCTTCGTGGATGCCCG
GGAGATCAAGCAGAATGCCCGGACGCTCATGAACTTACACAATAACGAGGCGGGTCGGAAGATCCTGGAG
GAGAACATGAAGCTGGAGTGTAAGTGCCATGGTGTGTCAGGCTCCTGTACCACTAAGACGTGCTGGACCA
CACTGCCACAGTTCCGAGAGCTAGGCTACGTGCTCAAGGACAAATACAACGAGGCCGTCCACGTGGAGCC
TGTGCGTGCCAGTCGAAACAAGCGGCCCACCTTTCTGAAGATCAAGAAGCCCCTGTCCTACCGCAAGCCC
ATGGACACTGACCTGGTGTATATCGAGAAGTCACCCAATTACTGTGAAGAGGACCCAGTGACAGGCAGCG
TGGGTACCCAGGGCCGAGCCTGCAATAAGACAGCCCCTCAGGCCAGTGGCTGTGACCTCATGTGCTGTGG
CCGTGGCTACAACACACACCAGTACGCCCGGGTGTGGCAGTGCAACTGCAAATTCCACTGGTGCTGCTAC
GTCAAGTGTAACACGTGCAGCGAGCGCACGGAGATGTATACGTGCAAGTGAATGCGGTCACAGGTCAGAT
CACAGGCAGGATACAGTTTCCCTGCAGGCCACTGCCTGGATGCTCACAGGGAAAGAACCACAGAAGCACT
GTCCTTGTCTTTCTGCTGAGGGGGAGGGGTATTCTGGGTTTCCTGCAGACTCCCGTGGGAAGCATCTC
TCAGAGGCCCGCCCATTCTTCTCCACATGGATGCTGCTCAGCCACCCTCCCCAGACACCGCCCGAGCCT
CTCCAGGGCTGGAACAAAGTTTTCTACGGCAGGAGCTCTGGAGCCTCGGGCCTCGTCATAGCAATATTTA
ACAGTTTATTCTGATATGAGATAATATTAATTTATTTAATTAAAGAGAATTCTTCCACTTCGTCGGGATC
CGTCTTCTGCAATCAAAGTGGACTGCTTGAGGTCCTGGTGGGATGACTTGCTAGGACTGGGAGCTGAGAA
CAGCTGTACATAATTATTCTTTATGCAGATGTTTCTACTAGTTGATTTCACAAGTACCCTTCTGCAGCGC
TAGGTGTTAAGTACAAAGAGAAGACGGTCTTTATACACATATAGATATATATATGCATACACATTTGTAA
CTTTGTTTTGTTTTGTTTTGCTGTTTGCTGCTACCTATCCAGACTCTAAGCTGGTCCAGATCTGGAATT
GTTTTTCTCCAGGACGTGCTCCTATCCTTTGCCCTTTACAGTTCAAACCTCTCCGTTAGAAAAGTTCCA
TTGGGAATGGCGTGTGTGTGATGGGACGAGGATCACAAATTCCCAGCAGTTTCCATCCTGAAACGTGAA
CCACTGGATAAGAGGCTTTCTAAGAGACTATTTTTCTATGGATATTTATTTATATGGAGTCTGCCTGCG
GTGCCCCATGGCCCATGCCTCTTCTTAACACTGGTACTCACTCAGGGGCAGAAGGACAAGGCCAGGTGTG
TGGGCAGGTCCCCCGGGGACCCTCACACAGCTGGAGCCTGGAGTTCTATTTGCCAAGGGGGCCATAGCAG
TTACCAGATGCCTGGGTTGGGTATCTTCTGTGTTAAACAAGAGGGAACCATCCCCTGGCTTTAGCCTGCT
AAGCTCAGGGCTTGGAATGGGGTCACTGGATGGTTATCTTGGGAGATGACCTCTGGATGAGCCTCAGCGG
TGGGTCAGTCAGTGTCTCACACACTTTGAGAAGCATGGGACCTGGCATTCATCATCAGGCAGAGGCCAGC
TCAGGGATGCCGCTATCCCATCAGGACAGCCCAGGCACTGCCTCTAGGTGAGGTGTAGTCCTAAGAGAAG
GGGTCAAGGAGGGGAAGGAGGAAGCCAAGGAGTGTTGGCCATCCTCAGTGAAAGCGATGGGAGCGTTCT
CTCAGCAGCAGAGACACAGCTGTACCTGTATCTCTCCAATGGGAAACCCCTCCAGAAGGCTGGGGATATT
TTTTATGTGTTTCCACATGCATTTCCACCTGTGTGCATGTAAGCACATGCGCACACTCCTGTGCCAGCAC
TCTGCGGCACCTCCAGGGTGCTCACGGGTACATGTGCTTACATGTATCTCTCTGTGCTTGGGAGATCAGA
CCATGTGCATGGAGCTGTATGCCTGAGCACTTGTGGTCTCAGGGGTTATTTCCAGGTATCTGCATTTGTG
GGTGGGGTGCAAGGTAGACAGCAGGGAACTGATTTGATTGTGTTGAGCCACAGTGAGACTGCAACTCTGA
ACTCTGTCTCCACAGCTGCTGGTGAAACTCAGATGCCTGTGAGACAACAGCCCTGAGCCTCATGGCCCAC
ATGCTGGGAGCCCCTCAGTGTCTAGGTCATGTCCAGTCCCCCACCTGGGTTACATCACGACCAATAAACA
TGGCTGTATGGCTGATTTCTTCCCTTG

FIG. 21

> BAB23470 | Mus musculus Wnt7a protein (amino acid sequence)
MTRKARRCLGHLFLSLGIVYLRIGGFSSVVALGASIICNKIPGLAPRQRAICQSRPDAIIVIGEGSQMGL
DECQFQFRNGRWNCSALGERTVFGKELKVGSREAAFTYAIIAAGVAHAITAACTQGNLSDCGCDKEKQGQ
YHRDEGWKWGGCSADIRYGIGFAKVFVDAREIKQNARTLMNLHNNEAGRKILEENMKLECKCHGVSGSCT
TKTCWTTLPQFRELGYVLKDKYNEAVHVEPVRASRNKRPTFLKIKKPLSYRKPMDTDLVYIEKSPNYCEE
DPVTGSVGTQGRACNKTAPQASGCDLMCCGRGYNTHQYARVWQCNCKFHWCCYVKCNTCSERTEMYTCK

FIG. 22

> NM_004625 | Homo sapiens Wnt7A cDNA sequence
GAGGGGCGGGGGCTGGAGGCAGCAGCGCCCCCGCACTCCCCGCGTCTCGCACACTTGCACCGGTCGCTCG
CGCGCAGCCCGGCGTCGCCCCACGCCGCGCTCGCTCCTCCCTCCCTCCTCCCGCTCCGTGGCTCCCGTGC
TCCTGGCGAGGCTCAGGCGCGGAGCGCGCGGACGGGCGCACCGACAGACGGCCCCGGGACGCCTCGGCT
CGCGCCTCCCGGGCGGGCTATGTTGATTGCCCCGCCGGGGCCGGCCCGCGGGATCAGCACAGCCCGGCCC
GCGGCCCCGGCCAATCGGGACTATGAACCGGAAAGCGCGGCGCTGCCTGGGCCACCTCTTTCTCAGC
CTGGGCATGGTCTACCTCCGGATCGGTGGCTTCTCCTCAGTGGTAGCTCTGGGCGCAAGCATCATCTGTA
ACAAGATCCCAGGCCTGGCTCCAGACAGCGGGCGATCTGCCAGAGCCGGCCCGACGCCATCATCGTCAT
AGGAGAAGGCTCACAAATGGGCCTGGACGAGTGTCAGTTTCAGTTCCGCAATGGCCGCTGGAACTGCTCT
GCACTGGGAGAGCGCACCGTCTTCGGAAGGAGCTCAAAGTGGGGAGCCGGGAGGCTGCGTTCACCTACG
CCATCATTGCCGCGGCGTGGCCCACGCCATCACAGCTGCCTGTACCCAGGGCAACCTGAGCGACTGTGG
CTGCGACAAAGAGAAGCAAGGCCAGTACCACCGGGACGAGGGCTGGAAGTGGGGTGGCTGCTCTGCCGAC
ATCCGCTACGGCATCGGCTTCGCCAAGGTCTTTGTGGATGCCCGGGAGATCAAGCAGAATGCCCGGACTC
TCATGAACTTGCACAACAACGAGGCAGGCCGAAAGATCCTGGAGGAGAACATGAAGCTGGAATGTAAGTG
CCACGGCGTGTCAGGCTCGTGCACCACCAAGACGTGCTGGACCACACTGCCACAGTTTCGGGAGCTGGGC
TACGTGCTCAAGGACAAGTACAACGAGGCCGTTCACGTGGAGCTGTGCGTGCCAGCCGCAACAAGCGGC
CCACCTTCCTGAAGATCAAGAAGCCACTGTCGTACCGCAAGCCCATGGACACGGACCTGGTGTACATCGA
GAAGTCGCCCAACTACTGCGAGGAGGACCCGGTGACCGGCAGTGTGGGCACCCAGGGCCGCGCCTGCAAC
AAGACGGCTCCCCAGGCCAGCGGCTGTGACCTCATGTGCTGTGGGCGTGGCTACAACACCCACCAGTACG
CCCGCGTGTGGCAGTGCAACTGTAAGTTCCACTGGTGCTGCTATGTCAAGTGCAACACGTGCAGCGAGCG
CACGGAGATGTACACGTGCAAGTGAGCCCCGTGTGCACACCACCCTCCCGCTGCAAGTCAGATTGCTGGG
AGGACTGGACCGTTTCCAAGCTGCGGGCTCCCTGGCAGGATGCTGAGCTTGTCTTTTCTGCTGAGGAGGG
TACTTTTCCTGGGTTTCCTGCAGGCATCCGTGGGGGAAAAAAAATCTCTCAGAGCCCTCAACTATTCTGT
TCCACACCCAATGCTGCTCCACCCTCCCCAGACACAGCCCAGGTCCCTCCGCGGCTGGAGCGAAGCCTT
CTGCAGCAGGAACTCTGGACCCCTGGGCCTCATCACAGCAATATTTAACAATTTATTCTGATAAAATAA
TATTAATTTATTTAATTAAAAAGAATTCTTCCACAAAAAAAAAAAAAAAAAA

FIG. 23

> O00755 | Homo sapiens Wnt7a protein (amino acid sequence)
MNRKARRCLGHLFLSLGMVYLRIGGFSSVVALGASIICNKIPGLAPRQRAICQSRPDAIIVIGEGSQMGL
DECQFQFRNGRWNCSALGERTVFGKELKVGSREAAFTYAIIAAGVAHAITAACTQGNLSDCGCDKEKQGQ
YHRDEGWKWGGCSADIRYGIGFAKVFVDAREIKQNARTLMNLHNNEAGRKILEENMKLECKCHGVSGSCT
TKTCWTTLPQFRELGYVLKDKYNEAVHVEPVRASRNKRPTFLKIKKPLSYRKPMDTDLVYIEKSPNYCEE
DPVTGSVGTQGRACNKTAPQASGCDLMCCGRGYNTHQYARVWQCNCKFHWCCYVKCNTCSERTEMYTCK

FIG. 24

```
> NM_008057 | Mus musculus Fzd7 cDNA sequence
GGCGGGCGGTGCTGGACGCGGAGAGTCGCGGGCCGGGAGGACTCTCATGCGCCGGGCGCGGCGGCGCCTC
CCTGTATCCAAGCCTCTCCCCAGCGCCTCGTCTTTTTCCTCCAGCTGAGAACGCCGCTGCACTCGCGACC
GGCGATGCGGGCCCCGGCACGGCGGCGTCGCACTCGCCCCTGGGCCTCTGCGCCCTGGTGCTTGCTCTT
CTGTGCGCGCTGCCCACGGACACCCGGGCTCAGCCATATCACGGCGAGAAAGGCATCTCGGTACCGGACC
ACGGCTTCTGCCAGCCCATCTCCATCCCGTTGTGCACGGATATCGCCTACAACCAGACCATCCTGCCCAA
CCTGCTGGGCCACACGAACCAAGAGGACGCGGGCCTCGAGGTGCACCAGTTCTACCCTCTGGTAAAGGTG
CAGTGTTCTCCTGAGCTACGCTTCTTCTTATGCTCTATGTACGCACCCGTGTGCACCGTGCTCGACCAAG
CCATTCCTCCGTGCCGTTCCTTGTGCGAGCGCGCCCGACAGGGCTGCGAGGCGCTCATGAACAAGTTCGG
CTTCCAGTGGCCAGAGCGGTTGCGCTGCGAGAACTTCCCAGTGCACGGTGCCGGCGAGATCTGCGTGGGG
CAGAACACGTCCGACGGCTCCGGGGGCGCGGGCGGCAGTCCCACCGCCTACCCTACTGCTCCCTACCTGC
CAGACCCACCTTTCACTGCGATGTCCCCCTCAGATGGCAGAGGCCGCTTGTCTTTCCCCTTCTCGTGTCC
GCGCCAGCTCAAGGTGCCCCCCTACCTGGGCTACCGCTTCCTAGGTGAGCGTGACTGCGGTGCCCCGTGT
GAGCCGGGCCGTGCTAACGGCCTCATGTACTTTAAAGAAGAGGAGAGACGGTTCGCCCGCCTCTGGGTGG
GTGTGTGGTCAGTGCTGTGCTGCGCCTCGACGCTCTTCACGGTGCTCACCTACCTAGTGGACATGCGTCG
CTTCAGCTATCCAGAGCGACCCATCATCTTCCTGTCGGGTTGCTACTTCATGGTGGCAGTGGCGCACGTG
GCAGGCTTCCTGCTAGAGGACCGTGCCGTGTGCGTGGAGCGCTTCTCGGACGATGGCTACCGCACGGTGG
CGCAGGGCACCAAGAAGGAGGGCTGCACCATCCTCTTCATGGTGCTTTACTTCTTCGGTATGGCCAGCTC
CATCTGGTGGGTCATTCTGTCCCTCACTTGGTTCCTGGCAGCTGGCATGAAGTGGGGCCACGAGGCCATC
GAGGCCAACTCGCAGTACTTTCATCTGGCCGCGTGGGCTGTGCCAGCGGTCAAGACAATCACCATTTTGG
CCATGGGCCAGGTGGATGGTGACCTACTCAGTGGAGTGTGCTACGTGGGCCTGTCTAGTGTGGATGCATT
GCGGGGCTTCGTGCTGGCGCCCTTGTTCGTCTACCTCTTCATCGGGACGTCCTTCCTGTTGGCCGGCTTT
GTGTCTCTCTTTCGCATCCGCACCATCATGAAGCACGACGGCACCAAGACAGAGAAGCTGGAGAAGCTGA
TGGTGCGCATCGGCGTCTTCAGCGTGCTCTACACGGTGCCGGCCACCATCGTGTTGGCCTGCTACTTTTA
TGAGCAGGCCTTCCGAGAGCACTGGGAACGCACCTGGCTCCTGCAGACTTGCAAGAGCTACGCTGTGCCC
TGCCCTCCGGGCCACTTCTCTCCCATGAGCCCCGACTTTACAGTCTTCATGATCAAGTACCTGATGACCA
TGATCGTGGGCATCACTACGGGCTTCTGGATCTGGTCGGGCAAGACCCTGCAGTCATGGCGTCGCTTCTA
CCACAGACTCAGCCACAGCAGCAAGGGGGAAACTGCGGTATGAGCCCCGGTCCTTACCCACCCTTGCCTC
TTCTACCCTTTTACAGGAGGAGAGGCATGGTAGGGAGAGAACTGCTGGGTGGGGCTTGTTTCCGTAAGC
TACCTGCCCCCTCCACTGAGCTTTAACCTGGAAGTGAGAAGTTATTTGGAGGTGAGAAGAGATTTGGGGC
GAGAGATGGTTTTGAGAGGAGGCCCAGATGAAAAAAGGCAAAGGCAGTGGCCGAAAAGACTTCTGGCTAA
GACTTGCAGGACGATGCTAACTGTGAAAGATATGGACCGGCTAGGGCCTAAGGGAAAGGTTGAGACCAGC
AGAGAGAGAGACTGGTGAGGTTTTCAGGCGCCAGAGATGAGCCAGGGCTGTGAGTCCAATCCCCTGCTGC
AAGGCAAGTGGTTGTTCTCACTCTAGTGAAGGGGGCTGGGAGGGAGGGTGATACCGCTCTGTCTGTAG
CCTAGGCTTTGTGGCCAAGATGGGGGGGACCTCCTGCGGTGCCCTTGTCAAGTGGTGGTCAAACCATAAT
CTCTTTTCACTGGGGCCAAACTGGAGCCCAGATGGGTTAATTTCCAGGGTCAGACCTTACAGTCCTCCTC
CCGGGCCCCCTCCCGCCTGCTTTTCCTTCCCTACTCCTTTCAAGTCTAGTAAAATAAGCATTTGGAAGGC
CGGGCCCTGCCTGCTAGAGTCCTAGCGTGAAGTTGGTTTTCAAGAGGAGGCCAAGAAGGCGAGTGGGAGA
TACAGTCTGCTACTTTTAATTTGTTGCTACTTTTTCATTTTCTAGGGAAGGCAGAGAGAAAAAGAATGT
TTTATTTGGTTTCATACCCTGAAAAAAGTCATGACTTGTTGCTTTTCAAAACAGGAACGCATTCACACA
CACACACACCCCATCCCACCCCCCTTGTCTTTGTTGTAAGAGACAAAGCGGGAAACAAAAGTGTCTCCCT
GAGGAAAGGCCTAACTGTGAAGCCAGCAGCTTTTACAGGCAAAGCCACAGAAATCCGAGGTTTTCCTTTG
GTTGTTAATTTGGTTGAGATAAACATTCCTTTTTAAGGAAGAGTGAAGAGCAGCTTTCATACCCATTCAG
GCACACGTTCTGACTTGGATAAAGGAAATGCTAGGAGTTTTGTTATTTGTTTTAAACAGATTTAATTCAG
AACACATGATCTAATAGACTCTTTTGCTTAATGAAATCTCCTCCCATTCTACGCCCCATAACCCAAATT
TTGATTTTTCTGCCCCCTTCCTTCCGTCCAATTTGGGATTTTTGCTGTTTTTGTTTTGTTGTTTTGTT
TTTCCTCCAGACAGGGTATCTCTGTGTAGCCCTGACTATCCAGGAACTGGCTCTGTAGAGCAGGCTGGCT
TTGAACTCACAGACATCCACCTGCCTCTGCCTCTCAATTGCTGGGATTAAAGGCATGGTCCACCAGGCCT
GGCTCCCCTTCCTAATTTGTATCTTTCAAGACATAACGCTCACATTAGTAAAGATAAAAGACAAAATTT
```

FIG. 25

```
TAACTTAAAGGTTTAAAAGCATTTTGCCCTCATTTTCTTGTTCTAGAGATGTAAACATCTATCTATCAGA
CACATGAGCTGACCCTTTCTCTCTCTGGTTGCATGAGGCGAGGGCAAGAGGAATGATAGCGAAGGAAGAG
GAGAGTTTGAGTCAGGTTTCAAGAAAGTCATTAAGGGAAGGTGAACTTCAAAGTGATTCTGGAGTTCTTT
GAAATGTGCTAGAAGACTTACATTTATTAATCTTAAATCGTGTACTTCTCTTTTTTTCCCTGCAATAGAA
GTCTGGTTCTTTGGCATAATGTAAAGCTGAGCAGAGCATCATGGGAGTTGACCTTTACCCTACCTTTGAC
ACTGACTGTCCTCCAATTTTGCAATGTTCTTCAGTTTCTCAGAGCAGTTTTTAATGCCAGCCAGGGGGGG
ATTGTCGGGAGGACAGATTACTTCATATGTGTCCTGTTCAGTTGAATGGAGCTGCTTTTACAATTAAAGT
GATCTTGTATTTTTTAAACTTTCAAAGTGATCTCACCTGTCAGAATTTTTTTAAGCTGCCACTACACAGG
TTTGGCATCTTTTGTGTTTTATCTCTTTAAGTGCATGTGAAATTTGTAAAATAGAGACAGTGCAGTATGT
ATATTTTGTAAATCTCCCATTTTTGTAAGAAAATATATATTGTATTTATACATTTTTACTTTGGATTTTT
GTTTGTTTACCTTTAAAGATCTACAATGAAGCCCCACTTTATCACATGTACAGATCACGAATAAATTTT
TTAAAAAATAAAAAAAAAAAAAAAAAAAAAAAAAAAAAAAA
```

FIG. 25 cont'd.

> NP_032083 | Mus musculus Fzd7 protein (amino acid sequence)
MRGPGTAASHSPLGLCALVLALLCALPTDTRAQPYHGEKGISVPDHGFCQPISIPLCTDIAYNQTILPNL
LGHTNQEDAGLEVHQFYPLVKVQCSPELRFFLCSMYAPVCTVLDQAIPPCRSLCERARQGCEALMNKFGF
QWPERLRCENFPVHGAGEICVGQNTSDGSGGAGGSPTAYPTAPYLPDPPFTAMSPSDGRGRLSFPFSCPR
QLKVPPYLGYRFLGERDCGAPCEPGRANGLMYFKEEERRFARLWVGVWSVLCCASTLFTVLTYLVDMRRF
SYPERPIIFLSGCYFMVAVAHVAGFLLEDRAVCVERFSDDGYRTVAQGTKKEGCTILFMVLYFFGMASSI
WWVILSLTWFLAAGMKWGHEAIEANSQYFHLAAWAVPAVKTITILAMGQVDGDLLSGVCYVGLSSVDALR
GFVLAPLFVYLFIGTSFLLAGFVSLFRIRTIMKHDGTKTEKLEKLMVRIGVFSVLYTVPATIVLACYFYE
QAFREHWERTWLLQTCKSYAVPCPPGHFSPMSPDFTVFMIKYLMTMIVGITTGFWIWSGKTLQSWRRFYH
RLSHSSKGETAV

FIG. 26

> NM_003507 | Homo sapiens Fzd7 cDNA
CTCTCCCAACCGCCTCGTCGCACTCCTCAGGCTGAGAGCACCGCTGCACTCGCGGCCGGCGATGCGGGAC
CCCGGCGCGGCCGCTCCGCTTTCGTCCCTGGGCCTCTGTGCCCTGGTGCTGGCGCTGCTGGGCGCACTGT
CCGCGGGCGCCGGGGCGCAGCCGTACCACGGAGAGAAGGGCATCTCCGTGCCGGACCACGGCTTCTGCCA
GCCCATCTCCATCCCGCTGTGCACGGACATCGCCTACAACCAGACCATCCTGCCCAACCTGCTGGGCCAC
ACGAACCAAGAGGACGCGGGCCTCGAGGTGCACCAGTTCTACCCGCTGGTGAAGGTGCAGTGTTCTCCCG
AACTCCGCTTTTTCTTATGCTCCATGTATGCGCCCGTGTGCACCGTGCTCGATCAGGCCATCCCGCCGTG
TCGTTCTCTGTGCGAGCGCGCCCGCCAGGGCTGCGAGGCGCTCATGAACAAGTTCGGCTTCCAGTGGCCC
GAGCGGCTGCGCTGCGAGAACTTCCCGGTGCACGGTGCGGGCGAGATCTGCGTGGGCCAGAACACGTCGG
ACGGCTCCGGGGCCCAGGCGGCGGCCCCACTGCCTACCCTACCGCGCCCTACCTGCCGGACCTGCCCTT
CACCGCGCTGCCCCGGGGGCCTCAGATGGCAGGGGGCGTCCCGCCTTCCCCTTCTCATGCCCCCGTCAG
CTCAAGGTGCCCCCGTACCTGGGCTACCGCTTCCTGGGTGAGCGCGATTGTGGCGCCCCGTGCGAACCGG
GCCGTGCCAACGGCCTGATGTACTTTAAGGAGGAGGAGAGGCGCTTCGCCCGCCTCTGGGTGGGCGTGTG
GTCCGTGCTGTGCTGCGCCTCGACGCTCTTTACCGTTCTCACCTACCTGGTGGACATGCGGCGCTTCAGC
TACCCAGAGCGGCCCATCATCTTCCTGTCGGGCTGCTACTTCATGGTGGCCGTGGCGCACGTGGCCGGCT
TCCTTCTAGAGGACCGCGCCGTGTGCGTGGAGCGCTTCTCGGACGATGGCTACCGCACGGTGGCGCAGGG
CACCAAGAAGGAGGGCTGCACCATCCTCTTCATGGTGCTCTACTTCTTCGGCATGGCCAGCTCCATCTGG
TGGGTCATTCTGTCTCTCACTTGGTTCCTGGCGGCCGGCATGAAGTGGGGCCACGAGGCCATCGAGGCCA
ACTCGCAGTACTTCCACCTGGCCGCGTGGGCCGTGCCCGCCGTCAAGACCATCACTATCCTGGCCATGGG
CCAGGTAGACGGGGACCTGCTGAGCGGGGTGTGCTACGTTGGCCTCTCCAGTGTGGACGCGCTGCGGGGC
TTCGTGCTGGCGCCTCTGTTCGTCTACCTCTTCATAGGCACGTCCTTCTTGCTGGCCGGCTTCGTGTCCC
TCTTCCGTATCCGCACCATCATGAAACACGACGGCACCAAGACCGAGAAGCTGGAGAAGCTCATGGTGCG
CATCGGCGTCTTCAGCGTGCTCTACACAGTGCCCGCCACCATCGTCCTGGCCTGCTACTTCTACGAGCAG
GCCTTCCGCGAGCACTGGGAGCGCACCTGGCTCCTGCAGACGTGCAAGAGCTATGCCGTGCCCTGCCCGC
CCGGCCACTTCCCGCCCATGAGCCCCGACTTCACCGTCTTCATGATCAAGTACCTGATGACCATGATCGT
CGGCATCACCACTGGCTTCTGGATCTGGTCGGGCAAGACCCTGCAGTCGTGGCGCCGCTTCTACCACAGA
CTTAGCCACAGCAGCAAGGGGGAGACTGCGGTATGAGCCCCGGCCCCTCCCCACCTTTCCCACCCCAGCC
CTCTTGCAAGAGGAGAGGCACGGTAGGGAAAAGAACTGCTGGGTGGGGGCCTGTTTCTGTAACTTTCTCC
CCCTCTACTGAGAAGTGACCTGGAAGTGAGAAGTTCTTTGCAGATTTGGGGCGAGGGGTGATTTGGAAAA
GAAGACCTGGGTGGAAAGCGGTTTGGATGAAAAGATTTCAGGCAAAGACTTGCAGGAAGATGATGATAAC
GGCGATGTGAATCGTCAAAGGTACGGGCCAGCTTGTGCCTAATAGAAGGTTGAGACCAGCAGAGACTGCT
GTGAGTTTCTCCCGGCTCCGAGGCTGAACGGGGACTGTGAGCGATCCCCCTGCTGCAGGGCGAGTGGCCT
GTCCAGACCCCTGTGAGGCCCCGGGAAAGGTACAGCCCTGTCTGCGGTGGCTGCTTTGTTGGAAAGAGGG
AGGGCCTCCTGCGGTGTGCTTGTCAAGCAGTGGTCAAACCATAATCTCTTTTCACTGGGGCCAAACTGGA
GCCCAGATGGGTTAATTTCCAGGGTCAGACATTACGGTCTCTCCTCCCCTGCCCCCTCCCGCCTGTTTTT
CCTCCCGTACTGCTTTCAGGTCTTGTAAAATAAGCATTTGGAAGTCTTGGGAGGCCTGCCTGCTAGAATC
CTAATGTGAGGATGCAAAAGAAATGATGATAACATTTTGAGATAAGGCCAAGGAGACGTGGAGTAGGTAT
TTTTGCTACTTTTTCATTTCTGGGGAAGGCAGGAGGCAGAAAGACGGGTGTTTTATTTGGTCTAATACC
CTGAAAAGAAGTGATGACTTGTTGCTTTTCAAAACAGGAATGCATTTTTCCCCTTGTCTTTGTTGTAAGA
GACAAAAGAGGAAACAAAAGTGTCTCCCTGTGGAAAGGCATAACTGTGACGAAAGCAACTTTTATAGGCA
AAGCAGCGCAAATCTGAGGTTTCCCGTTGGTTGTTAATTTGGTTGAGATAAACATTCCTTTTTAAGGAAA
AGTGAAGAGCAGTGTGCTGTCACACACCGTTAAGCCAGAGGTTCTGACTTCGCTAAAGGAAATGTAAGAG
GTTTTGTTGTCTGTTTTAAATAAATTTAATTCGGAACACATGATCCAACAGACTATGTTAAAATATTCAG
GGAAATCTCTCCCTTCATTTACTTTTTCTTGCTATAAGCCTATATTTAGGTTTCTTTTCTATTTTTTCT
CCCATTTGGATCCTTTGAGGTAAAAAAACATAATGTCTTCAGCCTCATAATAAAGGAAAGTTAATTAAAA
AAAAAAGCAAAGAGCCATTTTGTCCTGTTTTCTTGGTTCCATCAATCTGTTTATTAAACATCATCCATA
TGCTGACCCTGTCTCTGTGTGGTTGGGTTGGGAGGCGATCAGCAGATACCATAGTGAACGAAGAGGAAGG
TTTGAACCATGGGCCCCATCTTTAAAGAAAGTCATTAAAAGAAGGTAAACTTCAAAGTGATTCTGGAGTT

FIG. 27

```
CTTTGAAATGTGCTGGAAGACTTAAATTTATTAATCTTAAATCATGTACTTTTTTTCTGTAATAGAACTC
GGATTCTTTTGCATGATGGGGTAAAGCTTAGCAGAGAATCATGGGAGCTAACCTTTATCCCACCTTTGAC
ACTACCCTCCAATCTTGCAACACTATCCTGTTTCTCAGAACAGTTTTTAAATGCCAATCATAGAGGGTAC
TGTAAAGTGTACAAGTTACTTTATATATGTAATGTTCACTTGAGTGGAACTGCTTTTTACATTAAAGTTA
AAATCGATCTTGTGTTTCTTCAACCTTCAAAACTATCTCATCTGTCAGATTTTTAAAACTCCAACACAGG
TTTTGGCATCTTTTGTGCTGTATCTTTTAAGTGCATGTGAAATTTGTAAAATAGAGATAAGTACAGTATG
TATATTTTGTAAATCTCCCATTTTTGTAAGAAAATATATATTGTATTTATACATTTTTACTTTGGATTTT
TGTTTTGTTGGCTTTAAAGGTCTACCCCACTTTATCACATGTACAGATCACAAATAAATTTTTTAAATA
C
```

FIG. 27 cont'd.

```
>NP_003498 | Homo sapiens Fzd7 protein (amino acid sequence)
MRDPGAAAPLSSLGLCALVLALLGALSAGAGAQPYHGEKGISVPDHGFCQPISIPLCTDIAYNQTILPNL
LGHTNQEDAGLEVHQFYPLVKVQCSPELRFFLCSMYAPVCTVLDQAIPPCRSLCERARQGCEALMNKFGF
QWPERLRCENFPVHGAGEICVGQNTSDGSGGPGGGPTAYPTAPYLPDLPFTALPPGASDGRGRPAFPFSC
PRQLKVPPYLGYRFLGERDCGAPCEPGRANGLMYFKEEERRFARLWVGVWSVLCCASTLFTVLTYLVDMR
RFSYPERPIIFLSGCYFMVAVAHVAGFLLEDRAVCVERFSDDGYRTVAQGTKKEGCTILFMVLYFFGMAS
SIWWVILSLTWFLAAGMKWGHEAIEANSQYFHLAAWAVPAVKTITILAMGQVDGDLLSGVCYVGLSSVDA
LRGFVLAPLFVYLFIGTSFLLAGFVSLFRIRTIMKHDGTKTEKLEKLMVRIGVFSVLYTVPATIVLACYF
YEQAFREHWERTWLLQTCKSYAVPCPPGHFPPMSPDFTVFMIKYLMTMIVGITTGFWIWSGKTLQSWRRF
YHRLSHSSKGETAV
```

FIG. 28

> NM_033509 | Mus musculus Vangl2 cDNA sequence
CCGATTGCTTGGTTCTGGGTCCCGCCATGGGAGCCTGAGTGCCCTGCAGTCCCCTCCGGCCCCCTGCCCC
CGGGGCCTCGAGGGGGAAACAGGCGAGTGGTCTGGGACGGAGCCGGGGTGAGCGACCTCAGGAGCCCCCC
TCGTCAACCCCCATCGCCCGCGCTGCCGGTTCTGGAGCGCGGAGTTCGGAAAGACCGGGTGCGCTGCGGA
TACAAAGGCGCGGAGCGGAGTGGGGCGTGCGCCCAGTCCACCGGGCTGTTCGCAGTGGCGGGGAGCTGCC
GCTTGAATTTCTCTGAGATAAGCCCACTTGTCCAGCAAAATAGAGTCCCTCAGGGTGACGGTTGACTTCC
TAAAGGTGCCTCTTGGCCTGAAGAAGCCTGTGCTGAAGGAGGTGGCTGTGGGACCCCCAAGAGGTCCCA
GCCCGCGGCCCTGGAGCGCTACAAGGCACGGCGTTCGGACGCCATGGACACCGAGTCCCAGTACTCGGGC
TATTCCTACAAGTCGGGCCACTCCCGCAGCTCCCGGAAGCACAGGGACCGCCGGGACCGACACCGCTCTA
AGAGCCGGGATGGAGTCGTGGAGATAAATCAGTGACGATCCAGGCTCCGGGAGAACCCCTGCTGGACAA
TGAGTCCACGAGGGGGATGAGCGGGATGACAACTGGGGAGAAACAACAACGGTGGTCACGGGCACTTCT
GAGCACAGTATCTCCCATGATGACCTCACGCGCATCGCCAAGGACATGGAGGACAGTGTCCCGTTGGATT
GTTCCGCCACCTGGGCGTGGCGGCAGGGGCCATTCTGGCGCTGCTCTCGTTCCTCACCCCGCTGGCTTT
CCTGCTGCTGCCTCCACTGCTGTGGCGGGAGGAGCTGGAGCCGTGTGGGACGGCCTGTGAGGGCCTCTTC
ATCTCCGTGGCCTTCAAGCTGCTCATCCTGCTGTTGGGCAGCTGGGCTCTGTTCTTCCGCCGGCCCAAGG
CCTCACTGCCCCGAGTCTTCGTGTTACGAGCTCTGCTCATGGTGCTTGTCTTCCTGCTGGTTATTTCCTA
TTGGCTCTTCTACGGTGTGCGCATCTTGGACGCCCGGGAGCGGAGCTACCAGGGCGTGGTTCAGTTTGCC
GTTTCTCTAGTGGATGCTTTACTCTTCGTGCACTATCGGCCGTAGTTCTGCTGGAGCTCCGTCAGCTCC
AGCCCCAGTTCACACTCAAGGTCGTGCGATCCACAGATGGGGCAGCCGCTTCTACAATGTCGGCCATCT
CAGCATCCAGCGAGTGGCAGTGTGGATCCTGGAGAAGTATTACCATGACTTCCCTGTCTACAACCCCGCC
CTCCTCAACCTGCCCAAGTCCGTCCTGGCCAAGAAAGTGTCTGGCTTCAAGGTGTATTCTCTCGGAGAGG
AAAATAGCACCAATAACTCCACGGGCCAATCAAGGGCTGTGATCGCGGCTGCGGCACGGAGGCGCGACAA
CAGCCACAATGAGTACTACTACGAGGAAGCCGAGCATGAGCGCAGAGTGCGCAAGCGCAGGGCCAGGCTC
GTGGTGGCTGTGGAGGAGGCCTTCACGCACATTAAGCGGCTGCAGGAAGAGGAGCAGAAGAACCCCAGGG
AGGTGATGGACCCCCGGGAAGCAGCCCAAGCGATCTTTGCATCCATGGCTCGTGCCATGCAGAAGTACCT
TCGCACCACCAAACAGCAGCCTTACCATACCATGGAGAGCATCCTTCAGCACCTGGAGTTCTGCATTACC
CACGACATGACGCCCAAGGCCTTCCTGGAGCGATATTTGGCTGCTGGACCCACCATCCAGTACCACAAGG
AACGTTGGCTGGCCAAACAGTGGACCTTGGTGAGCGAGGAGCCGGTGACCAATGGGCTTAAGGATGGCAT
CGTGTTCCTCTTGAAGCGCCAGGACTTCAGCTTGGTAGTGAGCACCAAGAAGGTGCCCTTCTTCAAACTC
TCTGAGGAATTTGTGGATCCCAAGTCACATAAGTTCGTCATGCGGCTGCAGTCGGAGACCTCTGTGTGAC
TTTTGCAGCAGCCGCGGAGGAGGGATGTGGGGGGTTCCTGCGGAGTGGGAGGGGCTTGGTTCTCTGGCCC
TGACACATTTCTGCCAGTCCTACTTCCTCTTGCTCTTGTTTGTTTTTGTTTTTGTTTTTGTTTTTTT
TTTACTTGAATTAACTTATCCTGTACCCAGTCTCCCCTCTTCCTCAGTTTTTCCCATCTGGAAATCTGGA
GATAAATCTTGTTAACAATA

FIG. 29

> NP_277044 | Mus musculus Vangl2 protein (amino acid sequence)
MDTESQYSGYSYKSGHSRSSRKHRDRRDRHRSKSRDGSRGDKSVTIQAPGEPLLDNESTRGDERDDNWGE
TTTVVTGTSEHSISHDDLTRIAKDMEDSVPLDCSRHLGVAAGAILALLSFLTPLAFLLLPPLLWREELEP
CGTACEGLFISVAFKLLILLLGSWALFFRRPKASLPRVFVLRALLMVLVFLLVISYWLFYGVRILDARER
SYQGVVQFAVSLVDALLFVHYLAVVLLELRQLQPQFTLKVVRSTDGASRFYNVGHLSIQRVAVWILEKYY
HDFPVYNPALLNLPKSVLAKKVSGFKVYSLGEENSTNNSTGQSRAVIAAAARRRDNSHNEYYYEEAEHER
RVRKRRARLVVAVEEAFTHIKRLQEEEQKNPREVMDPREAAQAIFASMARAMQKYLRTTKQQPYHTMESI
LQHLEFCITHDMTPKAFLERYLAAGPTIQYHKERWLAKQWTLVSEEPVTNGLKDGIVFLLKRQDFSLVVS
TKKVPFFKLSEEFVDPKSHKFVMRLQSETSV

FIG. 30

> NM_020335 | Homo sapiens Vangl2 cDNA sequence
GGATCCCGATCTGATTCCTGATCCTTGATTCCTTGATCCTTGGTCCCGCCATGGGAGCCTGAGCGCCCCC
TATTCCCCCCTGGCCCCAGCCCCGGGGCCTTGAGGGGGAAGAGGCAGCGGTCTGGGACGGAGCAGGGG
GTGACCAGACTCAAGAACCCCCCCCTCAACATCCCCCATCGCGCGCGCTGCCTGTCCAGGAGCGCCGAGT
TCGGAGCGACCCGGAGCGCTGCGGATACAAAGGCGACGGGCCGAGCGGGGCGCCCGCGGAGCCCACCCGG
CAGTTCGCAGCGGCGGGAGCGTCGCTGGATTTTCTCTGAGACAAGCCCACCCGTCCAGCAAAATAGAGTC
CCTCAGGGTGACAGTTGACTTCCTGAAGGTGCCTCTTGGCCTAAAGAAGCCGGTGCTGAAGGAGGTGGCT
GTGGGGCCCCCAAGAGGCCCCAGCCTGCGGCCCTGGAGCGCTACAAGGCGCGGCGTTCAGACGCCATGG
ACACCGAGTCCAGTACTCGGGCTATTCCTACAAGTCGGGCCACTCCCGCAGCTCCCGCAAGCACAGGGA
CCGCCGGGACCGACACCGCTCTAAGAGTCGAGATGGGGCCGAGGGGACAAGTCGGTGACAATCCAGGCT
CCCGGGGAGCCCCTGCTGGACAATGAGTCCACACGAGGGGATGAGCGGGATGACAACTGGGGGGAAACGA
CGACAGTAGTAACGGGCACCTCAGAGCACAGCATCTCCCATGATGACCTCACACGCATCGCCAAGGACAT
GGAGGACAGTGTCCCTCTGGACTGCTCCCGTCACCTGGGTGTGGCAGCGGGGGCCACCCTGGCACTGCTG
TCTTTCCTCACGCCTCTGGCCTTCCTGCTGCTGCCCCACTGCTGTGGCGGGAGGAGCTGGAGCCTTGCG
GGACGGCCTGCGAGGGCCTCTTCATCTCTGTCGCCTTCAAGCTGCTCATCCTGCTACTGGGCAGCTGGGC
TCTGTTCTTCCGCCGGCCCAAGGCCTCGCTGCCCCGCGTCTTTGTGCTGCGTGCCCTGCTTATGGTGCTG
GTTTTCCTGCTCGTGGTCTCCTACTGGCTCTTCTATGGTGTGCGCATCCTGGATGCTCGGGAGCGCAGCT
ACCAGGGCGTGGTGCAGTTCGCCGTGTCGCTGGTGGACGCCCTTCTTTTCGTGCACTACCTGGCCGTGGT
CCTGCTGGAGCTGCGCCAGCTCCAGCCTCAGTTCACGCTCAAGGTCGTGCGCTCCACCGACGGCGCCAGC
CGCTTCTACAACGTTGGCCATCTCAGCATCCAGCGCGTGGCAGTGTGGATCCTGGAGAAGTATTACCATG
ACTTCCCTGTCTACAACCCTGCCCTCCTCAACCTGCCCAAGTCCGTCCTGGCCAAGAAAGTGTCTGGCTT
CAAGGTGTATTCCCTCGGAGAGGAAAACAGCACCAACAACTCCACTGGCCAGTCTCGGGCTGTGATTGCA
GCGGCAGCTCGGAGGCGGGACAACAGTCACAATGAGTACTACTATGAGGAGGCTGAGCATGAGCGAAGGG
TGCGCAAGAGGAGGCCAGGCTTGTAGTGGCGGTGGAGGAGGCCTTCACTCACATTAAGCGGCTGCAGGA
AGAGGAGCAGAAAAACCCCAGGGAGGTGATGGACCCCGGGAGGCAGCCCAAGCCATCTTTGCATCCATG
GCCCGTGCCATGCAGAAGTACCTTCGGACCACCAAGCAGCAGCCCTACCACACCATGGAGAGCATCCTGC
AGCACCTTGAATTCTGCATCACGCATGACATGACGCCCAAGGCCTTCTTGGAGCGATACTTGGCGGCTGG
ACCTACCATCCAGTACCACAAGGAACGCTGGCTGGCCAAACAGTGGACATTGGTGAGCGAGGAGCCGGTG
ACCAACGGCCTCAAGGATGGCATCGTTTTCCTCTTAAAACGCCAGGACTTCAGCCTGGTGGTCAGCACCA
AGAAGGTCCCATTCTTCAAACTCTCCGAGGAATTTGTGGATCCCAAGTCACACAAGTTTGTCATGAGGCT
GCAGTCTGAGACCTCAGTGTGACTGTGCAACAGCAGGGGAGTGGGAAACTCTGGGGGGTCCTGAGGGGG
TGGGAGGGGCTTGGTTCTCAGGCCCAGCCACATTCCTGCCACCCTTCTTCTTCTTGCTCTTTTTTTTTT
ACTTGAATTAACGCACCCCCACCTTCTCTCCTCGCTTCTTCCTTATTTTACCCCATGTGAACCTGGAGAG
ACCATCCTGCTGTCAACAGTACCTGGGAAGGACTCCCACCTCACCAACAACTTTGTATTACTCTAGGCC
CTGCAGGAATCAGTGCCTCTCTCCCTCTTCTTTCCCTAGTCTTTTCCCAGATTACAGTCTCTCCTGAAAG
GGCACAGGGCCCTGCTGATTGTACTTTCCCCTCCTGAGCCCCGACTCACAAATCCAAGTTCTTAAAACAT
TTCTCTTCAGTGGCCCAACAGGGTTTCTCTGGGGCACATGGACATGACTCCAGAGAGCCACAGTGCCAAA
CTCCTCCAGGGCAGCAACTGGCCCTCCTGTCCCTCACCCCAGCCACAACAAACCCTGGGTTCTAGGGCAG
GGATACTCCTGCCACACAGCCCGAGTTAGAAATCTCCTTGCTAGGAGCATTTGCTTCCACATATATTTAG
AGCAAAGAAGGATCCCATCCTTTTCCCAGAAATCTCCACCTAATGTTTTTGGTTTGTATGGTCACGTGAC
CATAGGCAACCACGTGGAAACCCTCTGTGACCACTTTTCCAGGGACTTAGGGGAAGGTACCTTTCTTCCA
ATGTGTCTTCCTAGGCAGCCCCTGAGGAGGAGGGCTGAATAGATCCCTGAGGTTTTGGAGAGACCCCCAT
CACTGACTCCTGCTCCCTAACCCTACCCTCACTTTCGTCCCCGCTCTTCCCAGTGAAGGATGGTATGTAG
ACTCCTGTACAGACATAGTGGCTTGCAGACCCTGACCCAGCCCTGTGGTCTTAGACAAATGTTTTTATT
TTTGTCACCAGCCACCCCTGTCCTGCCGCCTTCTCTCGACTCCAGAGACCTGTTGCCTCATCTCTTTTGG
GGAAGAGCCGGCAGCTCCTCCTCATCCCCTGCCTTAAGTCCAGTTCTTTGCCTCAGGGGTCTCGTTTCCT
TGGCCTTCCAGGGTCCCCACCCCTTTTCTCCCTGCCTGATTCTCTGAGCTCTGGGCTCCGTCTGTATTGG
GTTGAGGGGCAAGGATTACTGCCTTTTGTAGGTACTTCACCCCTCACCCCATTTTAGCTTCCATAGTCTT
TGCACCAAATCCAAATTCTTGATAATTTAGATCTCATTTTGAGCAAAATTTGCTGGCCCTCTAATAAATA

FIG. 31

```
TTTTCAATATAAATCTGAGCCTTTGACTCAGACATTTTTGCCAAGGAGAGTAGAATTAGGAAGTACCCAT
ATACATCCAGCCAGGATCCACATGGAGGACCTTTCTGATGGCTGCAATGACTAGGCCATTCCTCTGAGTA
ACTCACAGTGTCCTTTTGTAGGCCCTTCTTTTCCCTGAAAGACTGGTTGGTACTTACCTTGCAGAGCACA
TCCTGGGATAAGATCCCCAGTGTCTCCCCTGGGAGGCTCCCCCTCTGTGTAGCACCAGCCCTGGGAATGA
TGGAGCCTAGTGATCGGGGTTTCTCCTGCTGTCCTTTCTGCAAAAGTTCACTTGTTTACCCACCGCATGC
TAGAGAGGAGCTCATTGGCCAATGCTTACCTTGTCCCCAAAGGGGTGGGTTGTGGAGCTCACTTAGGCAG
GGCCTCTGGCTGGGGCCAGGGTTATGAGATAGGCCTGTATGAAATATGTCCTGTTCTGGGGGTCTGTCTC
TTTTCTTCTCTTCAAAAACTTTGTGTCAGAGAGTCCCTTCTGAGTCACATAAATACCTCACTATCCTGGA
AAACAGGGCCTGGATGGTGACTGGGGTCATTGCCTTTGTGGACAGGATGGAGTGTGGTGTGGTCTGAGGA
GCAGGTTGGGGTGGGGGAGAGGGAAAGGATTTGGGATCTTAGTTGCTGCCCTAGGTTAGGGGCTGGGGAG
TGTTTATTTTAAGATCCTGCCATGTTTTAATCACTGTGATTTTTTTTTCATTCCCCTTTCCTAAAAAAA
ATTTTTTTCCTCCAACTCTCTAAGCACTAAGGGCTGTGCCTGAGAATGGTAGCATTTTGGTCTTTTGCTT
CAGAACTGTGGTATCTTTGTCTTTTTTCATTATTATTATTATTATTATTATTATTATTACTATTGTTTTT
TAAAATGTCAGGATGAATTGTCAGACATATGGCCATGTGTTTGTCCTCTGCTTCTCCCCTGTGGGAAGTT
GTCTCCATGCTGTGAACTGCTGTGGGGTGTGCAGCTGACTCAGTCCCTCTGAGCAGTTTCCCCACTGTGT
CTGTCCCATCATGCGCTGGATCTGCTCATTCTCCTGCTGTGGGGGTATGCCCACCTCTTACCCCCTTGAC
ACCATAGGGCTGCTGTGGCTGGGCCTCACCAGCACTGTCTTTTGTGTGACTCATGGCATCCTCGTTCATC
CCCACCGTGCCTAGCAGGCCTTCCTTTTCACCACCTCGGAACGCTTGCCTTTCCTCCCTCCACAACAGGA
CGCTGTGCCTCAGTCCTTCACCTACCTCGCCACTCTGCCACTGTCCCCATTGGTCCTTTCTCCTAAACTG
GTCTTTGTGCTCTCTTTGTTTTTTCTTATTTCCCTCTTGTCTCTCATTTTTTCTTCCCATTCCCCTCCCA
TTTCAGCCCTTAACTTTTCTCTTTCCCATCTCCACTCAGTATTCCAATGGCAAACCCTGATGATGTAACA
CCTGCGATGAGACATCGGACTCTCCGGAACTTTCTCATCTGACACGTCTTTTTCCCAGGGTTCGTACTTC
TCCTCCATTGGTCCCAGGCTAACTCCCCTGTTCCTCTGTGGTGTCTGTCAGTCCGTCTGTCTTCTCTTTC
CTCTGCCCTTCCCACAGGGCAGTATCTGCTGATGGATTCAGTCCTGGTGTGTGATTGTTGTGATTTGTTC
TTCCGTGCGCAAAAGGAAGAGGGCTTTTGAGTCCCTTCCAAGTGAGATTGTAAATGTAGAATTTTCCAC
TGTTGGATCTAGATTTTTTTCCTTTTTTTGGGGGGGTGGGGTTACAGAGCTGAGACCTTGTGCATGCA
TGTAGAAAATTGTAAATGTAAATTTTTTTAATATATAAAAGCTTGTTTCTACAGTTTGCAGTGGATC
TAAACATTACGGCAATTTTAGGATTTTTTTCTTAAACATAGGAACTAAAACTGTACAAATTTTTTTATA
TAAAATAAAGACATTTGACTTTTGTGGGAAAAAAAAAAAAAAAAAAAAAAAAAAAAAAAAAAAAAAAAAA
AAAAAAAAAAAAAAAAAAAAAAAAA
```

FIG. 31 cont'd

```
> NP_065068 | Homo sapiens Vangl2 protein (amino acid sequence)
MDTESQYSGYSYKSGHSRSSRKHRDRRDRHRSKSRDGGRGDKSVTIQAPGEPLLDNESTRGDERDDNWGE
TTTVVTGTSEHSISHDDLTRIAKDMEDSVPLDCSRHLGVAAGATLALLSFLTPLAFLLLPPLLWREELEP
CGTACEGLFISVAFKLLILLLGSWALFFRRPKASLPRVFVLRALLMVLVFLLVVSYWLFYGVRILDARER
SYQGVVQFAVSLVDALLFVHYLAVVLLELRQLQPQFTLKVVRSTDGASRFYNVGHLSIQRVAVWILEKYY
HDFPVYNPALLNLPKSVLAKKVSGFKVYSLGEENSTNNSTGQSRAVIAAAARRRDNSHNEYYYEEAEHER
RVRKRRARLVVAVEEAFTHIKRLQEEEQKNPREVMDPREAAQAIFASMARAMQKYLRTTKQQPYHTMESI
LQHLEFCITHDMTPKAFLERYLAAGPTIQYHKERWLAKQWTLVSEEPVTNGLKDGIVFLLKRQDFSLVVS
TKKVPFFKLSEEFVDPKSHKFVMRLQSETSV
```

FIG. 32

SEQUENCE LISTING

```
<160> NUMBER OF SEQ ID NOS: 56

<210> SEQ ID NO 1
<211> LENGTH: 3177
<212> TYPE: DNA
<213> ORGANISM: Mus musculus
<220> FEATURE:
<221> NAME/KEY: misc_feature
<222> LOCATION: (1)..(3177)
<223> OTHER INFORMATION: Mouse Wnt7a cDNA

<400> SEQUENCE: 1
ggcagtcccc gcgcctcaaa cacttgccgc gatcgctggc gcgcagcggc gccccttgtt      60
gcgcttgttc tcccctcctc tggctccgcg gctcccgcgc tctgggacag tctccagtgc     120
ctagcgcgga ccgacgcacc gacggaccgc ccagggagcc tcggcccgcg ccccctgcgc     180
aggctatgtg gattgccccg ccgggccggg ctggcgggat cagcacagcc cggcccgtgg     240
cacccgccac cagcggggac tatgaccgg aaagcgcggc gctgcctggg ccacctcttt      300
ctcagcctgg gcatagtcta cctccggatc ggtggcttct cttcggtggt agctctgggt     360
gcgagcatca tctgtaacaa gatcccaggc ctggctccca gacagcgggc aatctgccag     420
agccggccgg acgccatcat cgtcatagga gaaggctccc aaatgggcct ggacgagtgt     480
cagtttcagt tccgaaatgg ccgttggaac tgctcagcgc tgggagagcg tactgtcttc     540
gggaaggagc tcaaagtggg gagtcgggag gctgccttca cctatgcgat tatcgctgcg     600
ggcgtggccc atgccatcac tgctgcctgc acccagggca acctgagcga ctgtggctgc     660
gacaaggaga agcaaggcca gtaccaccgg gacgagggct ggaagtgggg tggctgctct     720
gccgacatcc gctacggcat cggcttcgcc aaggtcttcg tggatgcccg ggagatcaag     780
cagaatgccc ggacgctcat gaacttacac aataacgagg cgggtcggaa gatcctggag     840
gagaacatga agctggagtg taagtgccat ggtgtgtcag gctcctgtac cactaagacg     900
tgctggacca cactgccaca gttccgagag ctaggctacg tgctcaagga caaatacaac     960
gaggccgtcc acgtggagcc tgtgcgtgcc agtcgaaaca agcggcccac ctttctgaag     1020
atcaagaagc ccctgtccta ccgcaagccc atggacactg acctggtgta tatcgagaag     1080
```

| | | | |
|---|---|---|---|
| tcacccaatt | actgtgaaga | ggacccagtg acaggcagcg tgggtaccca gggccgagcc | 1140 |
| tgcaataaga | cagcccctca | ggccagtggc tgtgacctca tgtgctgtgg ccgtggctac | 1200 |
| aacacacacc | agtacgcccg | ggtgtggcag tgcaactgca aattccactg gtgctgctac | 1260 |
| gtcaagtgta | acacgtgcag | cgagcgcacg gagatgtata cgtgcaagtg aatgcggtca | 1320 |
| caggtcagat | cacaggcagg | atacagtttc cctgcaggcc actgcctgga tgctcacagg | 1380 |
| gaaagaacca | cagaagcact | gtccttgtct tttctgctga ggggggaggg gtattctggg | 1440 |
| tttcctgcag | actcccgtgg | gaagcatctc tcagaggccc gcccattctt ctccacatgg | 1500 |
| atgctgctca | gccacccctcc | cccagacacc gcccgagcct ctccagggct ggaacaaagt | 1560 |
| tttctacggc | aggagctctg | gagcctcggg cctcgtcata gcaatattta acagtttatt | 1620 |
| ctgatatgag | ataatattaa | tttatttaat taaagagaat tcttccactt cgtcgggatc | 1680 |
| cgtcttctgc | aatcaaagtg | gactgcttga ggtcctggtg ggatgacttg ctaggactgg | 1740 |
| gagctgagaa | cagctgtaca | taattattct ttatgcagat gtttctacta gttgatttca | 1800 |
| caagtaccct | tctgcagcgc | taggtgttaa gtacaaagag aagacggtct ttatacacat | 1860 |
| atagatatat | atatgcatac | acatttgtaa cttttgtttg ttttgttttt gctgtttgct | 1920 |
| gctacctatc | cagactctaa | gctggtccag atctggaatt gttttctcc aggacgtgct | 1980 |
| cctatccttt | tgcccttttac | agttcaaacc tctccgttag aaaagttcca ttgggaatgg | 2040 |
| cgtgtgtgtg | atggggacga | ggatcacaaa ttcccagcag tttccatcct gaaacgtgaa | 2100 |
| ccactggata | agaggctttc | taagagacta ttttttctatg gatattttat ttatatggag | 2160 |
| tctgcctgcg | gtgccccatg | gcccatgcct cttcttaaca ctggtactca ctcagggca | 2220 |
| gaaggacaag | gccaggtgtg | tgggcaggtc ccccggggac cctcacacag ctggagcctg | 2280 |
| gagttctatt | tgccaagggg | gccatagcag ttaccagatg cctgggttgg gtatcttctg | 2340 |
| tgttaaacaa | gagggaacca | tccctggct ttagcctgct aagctcaggg cttggaatgg | 2400 |
| ggtcactgga | tggttatctt | gggagatgac ctctggatga gcctcagcgg tgggtcagtc | 2460 |
| agtgtctcac | acactttgag | aagcatggga cctggcattc atcatcaggc agaggccagc | 2520 |
| tcagggatgc | cgctatccca | tcaggacagc ccaggcactc cctctaggtg aggtgtagtc | 2580 |
| ctaagagaag | gggtcaagga | gggggaagga ggaagccaag gagtgttggc catcctcagt | 2640 |
| gaaagcgatg | ggagcgttct | ctcagcagca gagacacagc tgtacctgta tctctccaat | 2700 |
| gggaaacccc | tccagaaggc | tggggatatt ttttatgtgt ttccacatgc atttccacct | 2760 |
| gtgtgcatgt | aagcacatgc | gcacactcct gtgccagcac tctgcggcac ctccaggggt | 2820 |
| ctcacgggta | catgtgctta | catgtatctc tctgtgcttg ggagatcaga ccatgtgcat | 2880 |
| ggagctgtat | gcctgagcac | ttgtggtctc aggggttatt tccaggtatc tgcatttgtg | 2940 |
| ggtggggtgc | aaggtagaca | gcagggaact gatttgattg tgttgagcca cagtgagact | 3000 |
| gcaactctga | actctgtctc | cacagctgct ggtgaaactc agatgcctgt gagacaacag | 3060 |
| ccctgagcct | catggcccac | atgctgggag cccctcagtg tctaggtcat gtccagtccc | 3120 |
| ccacctgggt | tacatcacga | ccaataaaca tggctgtatg gctgatttct tcccttg | 3177 |

<210> SEQ ID NO 2
<211> LENGTH: 349
<212> TYPE: PRT
<213> ORGANISM: Mus musculus
<220> FEATURE:
<221> NAME/KEY: MISC_FEATURE
<222> LOCATION: (1)..(349)

<223> OTHER INFORMATION: Mouse Wnt7a Protein

<400> SEQUENCE: 2

```
Met Thr Arg Lys Ala Arg Arg Cys Leu Gly His Leu Phe Leu Ser Leu
1               5                   10                  15

Gly Ile Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345
```

<210> SEQ ID NO 3
<211> LENGTH: 1732
<212> TYPE: DNA
<213> ORGANISM: Homo sapiens
<220> FEATURE:
<221> NAME/KEY: misc_feature
<222> LOCATION: (1)..(1732)
<223> OTHER INFORMATION: Human Wnt7a cDNA

<400> SEQUENCE: 3

```
gaggggcggg ggctggaggc agcagcgccc ccgcactccc cgcgtctcgc acacttgcac      60
cggtcgctcg cgcgcagccc ggcgtcgccc cacgccgcgc tcgctcctcc ctccctcctc     120
ccgctccgtg gctcccgtgc tcctggcgag gctcaggcgc ggagcgcgcg gacgggcgca     180
ccgacagacg gccccgggga cgcctcggct cgcgcctccc gggcgggcta tgttgattgc     240
cccgccgggg ccggccgcgc ggatcagcac agcccggccc gcggcccgg cggccaatcg     300
ggactatgaa ccggaaagcg cggcgctgcc tgggccacct ctttctcagc ctgggcatgg     360
tctacctccg gatcggtggc ttctcctcag tggtagctct gggcgcaagc atcatctgta     420
acaagatccc aggcctggct cccagacagc gggcgatctg ccagagccgg ccgacgcca      480
tcatcgtcat aggagaaggc tcacaaatgg cctggacga gtgtcagttt cagttccgca      540
atggccgctg gaactgctct gcactgggag agcgcaccgt cttcgggaag gagctcaaag     600
tggggagccg ggaggctgcg ttcacctacg ccatcattgc cgccggcgtg cccacgcca      660
tcacagctgc ctgtacccag gcaacctga gcgactgtgg ctgcgacaaa gagaagcaag     720
gccagtacca ccgggacgag ggctggaagt ggggtggctg ctctgccgac atccgctacg     780
gcatcggctt cgccaaggtc tttgtggatg cccgggagat caagcagaat gcccggactc     840
tcatgaactt gcacaacaac gaggcaggcc gaaagatcct ggaggagaac atgaagctgg     900
aatgtaagtg ccacggcgtg tcaggctcgt gcaccaccaa gacgtgctgg accacactgc     960
cacagtttcg ggagctgggc tacgtgctca aggacaagta caacgaggcc gttcacgtgg    1020
agcctgtgcg tgccagccgc aacaagcggc ccaccttcct gaagatcaag aagccactgt    1080
cgtaccgcaa gcccatggac acggacctgg tgtacatcga agtcgccc aactactgcg     1140
aggaggaccc ggtgaccggc agtgtgggca cccagggccg cgcctgcaac aagacggctc    1200
cccaggccag cggctgtgac ctcatgtgct gtgggcgtgg ctacaacacc caccagtacg    1260
cccgcgtgtg gcagtgcaac tgtaagttcc actggtgctg ctatgtcaag tgcaacacgt    1320
gcagcgagcg cacggagatg tacacgtgca agtgagcccc gtgtgcacac caccctcccg    1380
ctgcaagtca gattgctggg aggactggac cgtttccaag ctgcgggctc cctggcagga    1440
tgctgagctt gtctttctg ctgaggaggg tacttttcct gggtttcctg caggcatccg    1500
tgggggaaaa aaaatctctc agagccctca actattctgt tccacaccca atgctgctcc    1560
accctccccc agacacagcc caggtccctc cgcggctgga gcgaagcctt ctgcagcagg    1620
aactctggac ccctgggcct catcacagca atatttaaca atttattctg ataaaaataa    1680
tattaattta tttaattaaa aagaattctt ccacaaaaaa aaaaaaaaa aa              1732
```

<210> SEQ ID NO 4
<211> LENGTH: 349
<212> TYPE: PRT
<213> ORGANISM: Homo sapiens
<220> FEATURE:
<221> NAME/KEY: MISC_FEATURE
<222> LOCATION: (1)..(349)
<223> OTHER INFORMATION: Human Wnt7a Protein

<400> SEQUENCE: 4

```
Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30
```

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Val Ile Gly Glu
 50                  55                  60

Gly Ser Gln Met Gly Leu Asp Glu Cys Gln Phe Gln Phe Arg Asn Gly
 65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
                115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
                180                 185                 190

Glu Glu Asn Met Lys Leu Glu Cys Lys Cys His Gly Val Ser Gly Ser
                195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
                275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
                340                 345

<210> SEQ ID NO 5
<211> LENGTH: 4171
<212> TYPE: DNA
<213> ORGANISM: Mus musculus
<220> FEATURE:
<221> NAME/KEY: misc_feature
<222> LOCATION: (1)..(4171)
<223> OTHER INFORMATION: Mouse Fzd7 cDNA

<400> SEQUENCE: 5
ggcgggcggt gctggacgcg gagagtcgcg ggccgggagg actctcatgc gccgggcgcg      60
gcggcgcctc cctgtatcca agcctctccc cagcgcctcg tctttttcct ccagctgaga     120
acgccgctgc actcgcgacc ggcgatgcgg ggccccggca cggcggcgtc gcactcgccc     180
ctgggcctct gcgccctggt gcttgctctt ctgtgcgcgc tgcccacgga cacccgggct     240

```
cagccatatc acggcgagaa aggcatctcg gtaccggacc acggcttctg ccagcccatc      300
tccatcccgt tgtgcacgga tatcgcctac aaccagacca tcctgcccaa cctgctgggc      360
cacacgaacc aagaggacgc gggcctcgag gtgcaccagt tctaccctct ggtaaaggtg      420
cagtgttctc ctgagctacg cttcttctta tgctctatgt acgcacccgt gtgcaccgtg      480
ctcgaccaag ccattcctcc gtgccgttcc ttgtgcgagc gcgcccgaca gggctgcgag      540
gcgctcatga acaagttcgg cttccagtgg ccagagcggt tgcgctgcga gaacttccca      600
gtgcacggtg ccggcgagat ctgcgtgggg cagaacacgt ccgacggctc cggggcgcg      660 ggcggcagtc ccaccgccta ccctactgct ccctacctgc cagacccacc tttcactgcg      720
atgtccccct cagatggcag aggccgcttg tcttccccct tctcgtgtcc gcgccagctc      780
aaggtgcccc cctacctggg ctaccgcttc ctaggtgagc gtgactgcgg tgccccgtgt      840
gagccgggcc gtgctaacgg cctcatgtac tttaaagaag aggagagacg gttcgcccgc      900
ctctgggtgg gtgtgtggtc agtgctgtgc tgcgcctcga cgctcttcac ggtgctcacc      960
tacctagtgg acatgcgtcg cttcagctat ccagagcgac ccatcatctt cctgtcgggt     1020
tgctacttca tggtggcagt ggcgcacgtg gcaggcttcc tgctagagga ccgtgccgtg     1080
tgcgtggagc gcttctcgga cgatggctac cgcacggtgg cgcagggcac caagaaggag     1140
ggctgcacca tcctcttcat ggtgctttac ttcttcggta tggccagctc catctggtgg     1200
gtcattctgt ccctcacttg gttcctggca gctggcatga agtggggcca cgaggccatc     1260
gaggccaact cgcagtactt tcatctggcc gcgtgggctg tgccagcggt caagacaatc     1320 accatttttgg ccatgggcca ggtggatggt gacctactca gtggagtgtg ctacgtgggc     1380
ctgtctagtg tggatgcatt gcggggcttc gtgctggcgc ccttgttcgt ctacctcttc     1440
atcgggacgt ccttcctgtt ggccggcttt gtgtctctct ttcgcatccg caccatcatg     1500
aagcacgacg gcaccaagac agagaagctg gagaagctga tggtgcgcat cggcgtcttc     1560
agcgtgctct acacggtgcc ggccaccatc gtgttggcct gctacttta tgagcaggcc     1620 ttccagagag actgggaacg cacctggctc ctgcagactt gcaagagcta cgctgtgccc     1680
tgccctccgg gccacttctc tcccatgagc cccgacttta cagtcttcat gatcaagtac     1740
ctgatgacca tgatcgtggg catcactacg ggcttctgga tctggtcggg caagaccctg     1800
cagtcatggc gtcgcttcta ccacagactc agccacagca gcaggggga aactgcggta     1860 tgagccccgg tccttaccca cccttgcctc ttctaccctt ttacaggagg agaggcatgg     1920
tagggagaga actgctgggt gggggcttgt ttccgtaagc tacctgcccc ctccactgag     1980
ctttaacctg gaagtgagaa gttatttgga ggtgagaaga gatttggggc gagagatggt     2040
tttgagagga ggcccagatg aaaaaaggca aaggcagtgg ccgaaaagac ttctggctaa     2100
gacttgcagg acgatgctaa ctgtgaaaga tatggaccgg ctagggccta agggaaaggt     2160
tgagaccagc agagagagag actggtgagg ttttcaggcg ccagagatga gccagggctg     2220
tgagtccaat cccctgctgc aaggcaagtg gttgttctca ctctagtgaa ggggggctgg     2280
gaggggaggg tgataccgct ctgtctgtag cctaggcttt gtggccaaga tgggggggac     2340
ctcctgcggt gcccttgtca agtggtggtc aaaccataat ctcttttcac tggggccaaa     2400
ctggagccca gatgggttaa tttccagggt cagaccttac agtcctcctc ccgggccccc     2460
tcccgcctgc ttttccttcc ctactccttt caagtctagt aaaataagca tttgaaggc      2520 cgggccctgc ctgctagagt cctagcgtga agttggtttt caagaggagg ccaagaaggc      2580
```

-continued

```
gagtgggaga tacagtctgc tactttttaa tttgttgcta cttttttcatt ttctagggaa   2640 ggcagagaga aaaagaatgt tttatttggt ttcatacccct gaaaaaaagt catgacttgt   2700
tgcttttcaa aacaggaacg cattcacaca cacacacacc ccatcccacc cccttgtct    2760 ttgttgtaag agacaaagcg ggaaacaaaa gtgtctccct gaggaaaggc ctaactgtga   2820
agccagcagc ttttacaggc aaagccacag aaatccgagg ttttcctttg gttgttaatt   2880
tggttgagat aaacattcct ttttaaggaa gagtgaagag cagctttcat acccattcag   2940
gcacacgttc tgacttggat aaaggaaatg ctaggagttt tgttatttgt tttaaacaga   3000
tttaattcag aacacatgat ctaatagact cttttgctta atgaaatctc ctcccattct   3060
acgcccccat aacccaaatt tgatttttc tgccccttc cttccgtcca atttgggatt     3120
tttgctgttt ttgttttgtt gtgttttgtt tttcctccag acagggtatc tctgtgtagc    3180
cctgactatc caggaactgg ctctgtagag caggctggct tgaactcac agacatccac    3240 ctgcctctgc ctctcaattg ctgggattaa aggcatggtc caccaggcct ggctcccctt    3300
cctaatttgt atctttcaag acataacgct cacattagta aagataaaag acaaaaattt    3360
taacttaaag gtttaaaagc attttgccct cattttcttg ttctagagat gtaaacatct    3420
atctatcaga cacatgagct gacccttct ctctctggtt gcatgaggcg agggcaagag    3480
gaatgatagc gaaggaagag gagagtttga gtcaggtttc aagaaagtca ttaagggaag    3540
gtgaacttca aagtgattct ggagttcttt gaaatgtgct agaagactta catttattaa    3600
tcttaaatcg tgtacttctc ttttttttccc tgcaatagaa gtctggttct ttggcataat    3660
gtaaagctga gcagagcatc atgggagttg acctttaccc taccctttgac actgactgtc   3720 ctccaatttt gcaatgttct tcagtttctc agagcagttt ttaatgccag ccaggggggg    3780
attgtcggga ggacagatta cttcatatgt gtcctgttca gttgaatgga gctgctttta    3840
caattaaagt gatcttgtat ttttttaaact ttcaaagtga tctcacctgt cagaattttt    3900
ttaagctgcc actacacagg tttggcatct tttgtgtttt atctctttaa gtgcatgtga    3960
aatttgtaaa atagagacag tgcagtatgt atattttgta aatctcccat ttttgtaaga    4020
aaatatatat tgtatttata cattttact ttggatttt gttttgttta cctttaaga     4080 tctacaatga agccccactt tatcacatgt acagatcacg aataaatttt ttaaaaaata    4140
aaaaaaaaaa aaaaaaaaaa aaaaaaaaaa a                                   4171
```

<210> SEQ ID NO 6
<211> LENGTH: 572
<212> TYPE: PRT
<213> ORGANISM: Mus musculus
<220> FEATURE:
<221> NAME/KEY: MISC_FEATURE
<222> LOCATION: (1)..(572)
<223> OTHER INFORMATION: Mouse Fzd7 Protein

<400> SEQUENCE: 6

Met Arg Gly Pro Gly Thr Ala Ala Ser His Ser Pro Leu Gly Leu Cys
1               5                   10                  15

Ala Leu Val Leu Ala Leu Leu Cys Ala Leu Pro Thr Asp Thr Arg Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly

```
            65                  70                  75                  80
Leu Glu Val His Gln Phe Tyr Pro Leu Val Lys Val Gln Cys Ser Pro
                        85                  90                  95
Glu Leu Arg Phe Phe Leu Cys Ser Met Tyr Ala Pro Val Cys Thr Val
                100                 105                 110
Leu Asp Gln Ala Ile Pro Pro Cys Arg Ser Leu Cys Glu Arg Ala Arg
                115                 120                 125
Gln Gly Cys Glu Ala Leu Met Asn Lys Phe Gly Phe Gln Trp Pro Glu
        130                 135                 140
Arg Leu Arg Cys Glu Asn Phe Pro Val His Gly Ala Gly Glu Ile Cys
145                 150                 155                 160
Val Gly Gln Asn Thr Ser Asp Gly Ser Gly Gly Ala Gly Gly Ser Pro
                    165                 170                 175
Thr Ala Tyr Pro Thr Ala Pro Tyr Leu Pro Asp Pro Pro Phe Thr Ala
                180                 185                 190
Met Ser Pro Ser Asp Gly Arg Gly Arg Leu Ser Phe Pro Phe Ser Cys
            195                 200                 205
Pro Arg Gln Leu Lys Val Pro Pro Tyr Leu Gly Tyr Arg Phe Leu Gly
        210                 215                 220
Glu Arg Asp Cys Gly Ala Pro Cys Glu Pro Gly Arg Ala Asn Gly Leu
225                 230                 235                 240
Met Tyr Phe Lys Glu Glu Glu Arg Arg Phe Ala Arg Leu Trp Val Gly
                    245                 250                 255
Val Trp Ser Val Leu Cys Cys Ala Ser Thr Leu Phe Thr Val Leu Thr
                260                 265                 270
Tyr Leu Val Asp Met Arg Arg Phe Ser Tyr Pro Glu Arg Pro Ile Ile
            275                 280                 285
Phe Leu Ser Gly Cys Tyr Phe Met Val Ala Val Ala His Val Ala Gly
        290                 295                 300
Phe Leu Leu Glu Asp Arg Ala Val Cys Val Glu Arg Phe Ser Asp Asp
305                 310                 315                 320
Gly Tyr Arg Thr Val Ala Gln Gly Thr Lys Lys Glu Gly Cys Thr Ile
                    325                 330                 335
Leu Phe Met Val Leu Tyr Phe Phe Gly Met Ala Ser Ser Ile Trp Trp
                340                 345                 350
Val Ile Leu Ser Leu Thr Trp Phe Leu Ala Ala Gly Met Lys Trp Gly
            355                 360                 365
His Glu Ala Ile Glu Ala Asn Ser Gln Tyr Phe His Leu Ala Ala Trp
        370                 375                 380
Ala Val Pro Ala Val Lys Thr Ile Thr Ile Leu Ala Met Gly Gln Val
385                 390                 395                 400
Asp Gly Asp Leu Leu Ser Gly Val Cys Tyr Val Gly Leu Ser Ser Val
                    405                 410                 415
Asp Ala Leu Arg Gly Phe Val Leu Ala Pro Leu Phe Val Tyr Leu Phe
                420                 425                 430
Ile Gly Thr Ser Phe Leu Leu Ala Gly Phe Val Ser Leu Phe Arg Ile
            435                 440                 445
Arg Thr Ile Met Lys His Asp Gly Thr Lys Thr Glu Lys Leu Glu Lys
        450                 455                 460
Leu Met Val Arg Ile Gly Val Phe Ser Val Leu Tyr Thr Val Pro Ala
465                 470                 475                 480
Thr Ile Val Leu Ala Cys Tyr Phe Tyr Glu Gln Ala Phe Arg Glu His
                    485                 490                 495
```

```
Trp Glu Arg Thr Trp Leu Leu Gln Thr Cys Lys Ser Tyr Ala Val Pro
                500                 505                 510

Cys Pro Pro Gly His Phe Ser Pro Met Ser Pro Asp Phe Thr Val Phe
            515                 520                 525

Met Ile Lys Tyr Leu Met Thr Met Ile Val Gly Ile Thr Thr Gly Phe
        530                 535                 540

Trp Ile Trp Ser Gly Lys Thr Leu Gln Ser Trp Arg Arg Phe Tyr His
545                 550                 555                 560

Arg Leu Ser His Ser Ser Lys Gly Glu Thr Ala Val
                565                 570

<210> SEQ ID NO 7
<211> LENGTH: 3851
<212> TYPE: DNA
<213> ORGANISM: Homo sapiens
<220> FEATURE:
<221> NAME/KEY: misc_feature
<222> LOCATION: (1)..(3851)
<223> OTHER INFORMATION: Human Fzd7 cDNA

<400> SEQUENCE: 7
ctctcccaac cgcctcgtcg cactcctcag gctgagagca ccgctgcact cgcggccggc      60
gatgcgggac cccggcgcgg ccgctccgct ttcgtccctg ggcctctgtg ccctggtgct     120
ggcgctgctg ggcgcactgt ccgcgggcgc cggggcgcag ccgtaccacg agagaagggg     180
catctccgtg ccggaccacg gcttctgcca gcccatctcc atcccgctgt gcacggacat     240
cgcctacaac cagaccatcc tgcccaacct gctgggccac acgaaccaag aggacgcggg     300
cctcgaggtg caccagttct acccgctggt gaaggtgcag tgttctcccg aactccgctt     360
tttcttatgc tccatgtatg cgcccgtgtg caccgtgctc gatcaggcca tcccgccgtg     420
tcgttctctg tgcgagcgcg cccgccaggg ctgcgaggcg ctcatgaaca agttcggctt     480
ccagtggccc gagcggctgc gctgcgagaa cttcccggtg cacggtgcgg gcgagatctg     540
cgtgggccag aacacgtcgg acggctccgg gggcccaggc ggcggcccca ctgcctaccc     600
taccgcgccc tacctgccgg acctgccctt caccgcgctg cccccggggg cctcagatgg     660 caggggggcgt cccgccttcc ccttctcatg cccccgtcag ctcaaggtgc cccgtacct     720 gggctaccgc ttcctgggtg agcgcgattg tggcgcccg tgcgaaccgg gccgtgccaa     780
cggcctgatg tactttaagg aggaggagag gcgcttcgcc cgcctctggg tgggcgtgtg     840
gtccgtgctg tgctgcgcct cgacgctctt taccgttctc acctacctgg tggacatgcg     900
gcgcttcagc tacccagagc ggcccatcat cttcctgtcg ggctgctact tcatggtggc     960
cgtggcgcac gtggccggct ccttctctaga ggaccgcgcc gtgtgcgtgg agcgcttctc    1020
ggacgatggc taccgcacgg tggcgcaggg caccaagaag gagggctgca ccatcctctt    1080
catggtgctc tacttcttcg gcatggccag ctccatctgg tgggtcattc tgtctctcac    1140
ttggttcctg gcggccggca tgaagtgggg ccacgaggcc atcgaggcca actcgcagta    1200
cttccacctg gccgcgtggg ccgtgcccgc cgtcaagacc atcactatcc tggccatggg    1260
ccaggtagac ggggacctgc tgagcggggt gtgctacgtt ggcctctcca gtgtggacgc    1320 gctgcgggc ttcgtgctgg cgcctctgtt cgtctaccct tcataggca cgtccttctt    1380 gctggccggc ttcgtgtccc tcttccgtat ccgcaccatc atgaaacacg acggcaccaa    1440
gaccgagaag ctgagaaagc tcatggtgcg catcggcgtc ttcagcgtgc tctacacagt    1500 gccccgccacc atcgtcctgg cctgctactt ctacgagcag gccttccgcg agcactggga    1560
```

-continued

```
gcgcacctgg ctcctgcaga cgtgcaagag ctatgccgtg ccctgcccgc ccggccactt    1620
cccgcccatg agccccgact tcaccgtctt catgatcaag tacctgatga ccatgatcgt    1680
cggcatcacc actggcttct ggatctggtc gggcaagacc ctgcagtcgt ggcgccgctt    1740
ctaccacaga cttagccaca gcagcaaggg ggagactgcg gtatgagccc cggcccctcc    1800
ccacctttcc caccccagcc ctcttgcaag aggagaggca cggtagggaa aagaactgct    1860 gggtggggc ctgtttctgt aactttctcc ccctctactg agaagtgacc tggaagtgag    1920
aagttctttg cagatttggg gcgaggggtg atttggaaaa aagacctgg gtggaaagcg     1980 gtttggatga aaagatttca ggcaaagact tgcaggaaga tgatgataac ggcgatgtga    2040
atcgtcaaag gtacgggcca gcttgtgcct aatagaaggt tgagaccagc agagactgct    2100
gtgagtttct cccggctccg aggctgaacg gggactgtga gcgatccccc tgctgcaggg    2160
cgagtggcct gtccagaccc ctgtgaggcc ccgggaaagg tacagccctg tctgcggtgg    2220
ctgctttgtt ggaaagaggg agggcctcct gcggtgtgct tgtcaagcag tggtcaaacc    2280
ataatctctt ttcactgggg ccaaactgga gcccagatgg gttaatttcc agggtcagac    2340
attacggtct ctcctcccct gccccctccc gcctgttttt cctcccgtac tgcttttagg    2400
tcttgtaaaa taagcatttg gaagtcttgg gaggcctgcc tgctagaatc ctaatgtgag    2460
gatgcaaaag aaatgatgat aacatttga gataaggcca aggagacgtg gagtaggtat    2520
ttttgctact ttttcattttt ctggggaagg caggaggcag aaagacgggt gttttatttg    2580
gtctaatacc ctgaaaagaa gtgatgactt gttgcttttc aaaacaggaa tgcattttc     2640 cccttgtctt tgttgtaaga gacaaagag gaaacaaaag tgtctccctg tggaaaggca    2700
taactgtgac gaaagcaact tttataggca aagcagcgca atctgaggt ttcccgttgg     2760 ttgttaattt ggttgagata acattcctt tttaaggaaa agtgaagagc agtgtgctgt     2820
cacacaccgt taagccagag gttctgactt cgctaaagga aatgtaagag gttttgttgt    2880 ctgtttaaa taaatttaat tcggaacaca tgatccaaca gactatgtta aaatattcag     2940
ggaaatctct cccttcattt acttttctt gctataagcc tatatttagg ttttcttttct    3000 attttttct cccatttgga tcctttgagg taaaaaaaca taatgtcttc agcctcataa     3060
taaaggaaag ttaattaaaa aaaaaaagca aagagccatt ttgtcctgtt ttcttggttc    3120
catcaatctg tttattaaac atcatccata tgctgaccct gtctctgtgt ggttgggttg    3180
ggaggcgatc agcagatacc atagtgaacg aagaggaagg tttgaaccat gggcccatc    3240 tttaaagaaa gtcattaaaa gaaggtaaac ttcaaagtga ttctggagtt ctttgaaatg    3300
tgctggaaga cttaaattta ttaatcttaa atcatgtact ttttttctgt aatagaactc    3360
ggattctttt gcatgatggg gtaaagctta gcagagaatc atgggagcta acctttatcc    3420
cacctttgac actaccctcc aatcttgcaa cactatcctg tttctcagaa cagtttttaa    3480
atgccaatca tagagggtac tgtaaagtgt acaagttact ttatatatgt aatgttcact    3540
tgagtggaac tgcttttac attaaagtta aaatcgatct tgtgtttctt caaccttcaa     3600
aactatctca tctgtcagat ttttaaaact ccaacacagg ttttggcatc ttttgtgctg    3660 tatctttaa gtgcatgtga aatttgtaaa atagagataa gtacagtatg tatatttgt     3720 aaatctccca tttttgtaag aaaatatata ttgtatttat acattttac tttggatttt     3780 tgttttgttg gctttaaagg tctaccccac tttatcacat gtacagatca caaataaatt    3840
tttttaaata c                                                         3851
```

<210> SEQ ID NO 8
<211> LENGTH: 574
<212> TYPE: PRT
<213> ORGANISM: Homo sapiens
<220> FEATURE:
<221> NAME/KEY: MISC_FEATURE
<222> LOCATION: (1)..(574)
<223> OTHER INFORMATION: Human Fzd7 Protein

<400> SEQUENCE: 8

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
        50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
            85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
            115                 120                 125

Gln Gly Cys Glu Ala Leu Met Asn Lys Phe Gly Phe Gln Trp Pro Glu
        130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
            165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
            195                 200                 205

Ser Cys Pro Arg Gln Leu Lys Val Pro Pro Tyr Leu Gly Tyr Arg Phe
        210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
            245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
            275                 280                 285

Ile Ile Phe Leu Ser Gly Cys Tyr Phe Met Val Ala Val Ala His Val
            290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
            325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys

```
                355                 360                 365
Trp Gly His Glu Ala Ile Glu Ala Asn Ser Gln Tyr Phe His Leu Ala
        370                 375                 380
Ala Trp Ala Val Pro Ala Val Lys Thr Ile Thr Ile Leu Ala Met Gly
385                 390                 395                 400
Gln Val Asp Gly Asp Leu Leu Ser Gly Val Cys Tyr Val Gly Leu Ser
                405                 410                 415
Ser Val Asp Ala Leu Arg Gly Phe Val Leu Ala Pro Leu Phe Val Tyr
            420                 425                 430
Leu Phe Ile Gly Thr Ser Phe Leu Leu Ala Gly Phe Val Ser Leu Phe
                435                 440                 445
Arg Ile Arg Thr Ile Met Lys His Asp Gly Thr Lys Thr Glu Lys Leu
        450                 455                 460
Glu Lys Leu Met Val Arg Ile Gly Val Phe Ser Val Leu Tyr Thr Val
465                 470                 475                 480
Pro Ala Thr Ile Val Leu Ala Cys Tyr Phe Tyr Glu Gln Ala Phe Arg
                485                 490                 495
Glu His Trp Glu Arg Thr Trp Leu Leu Gln Thr Cys Lys Ser Tyr Ala
            500                 505                 510
Val Pro Cys Pro Pro Gly His Phe Pro Pro Met Ser Pro Asp Phe Thr
        515                 520                 525
Val Phe Met Ile Lys Tyr Leu Met Thr Met Ile Val Gly Ile Thr Thr
    530                 535                 540
Gly Phe Trp Ile Trp Ser Gly Lys Thr Leu Gln Ser Trp Arg Arg Phe
545                 550                 555                 560
Tyr His Arg Leu Ser His Ser Ser Lys Gly Glu Thr Ala Val
                565                 570
```

<210> SEQ ID NO 9
<211> LENGTH: 2260
<212> TYPE: DNA
<213> ORGANISM: Mus musculus
<220> FEATURE:
<221> NAME/KEY: misc_feature
<222> LOCATION: (1)..(2260)
<223> OTHER INFORMATION: Mouse Vangl2 cDNA

<400> SEQUENCE: 9

```
ccgattgctt ggttctgggt cccgccatgg gagcctgagt gccctgcagt cccctccggc      60
cccctgcccc cggggcctcg aggggggaaac aggcgagtgg tctgggacgg agccggggtg    120
agcgacctca ggagcccccc tcgtcaaccc ccatcgcccg cgctgccggt tctggagcgc    180
ggagttcgga agaccgggt gcgctgcgga tacaaaggcg cggagcggag tggggcgtgc    240
gcccagtcca ccgggctgtt cgcagtggcg ggagctgcc gcttgaattt ctctgagata    300
agcccacttg tccagcaaaa tagagtccct cagggtgacg gttgacttcc taaaggtgcc    360
tcttggcctg aagaagcctg tgctgaagga ggtggctgtg gacccccca agaggtccca    420 gcccgcggcc ctggagcgct acaaggcacg gcgttcggac gccatggaca ccgagtccca    480
gtactcgggc tattcctaca agtcgggcca ctcccgcagc tcccggaagc acagggaccg    540
ccgggaccga caccgctcta agagccggga tgggagtcgt ggagataaat cagtgacgat    600
ccaggctccg ggagaacccc tgctggacaa tgagtccacg agggggggatg agcgggatga    660 caactgggga gaaacaacaa cggtggtcac gggcacttct gagcacagta tctcccatga    720
tgacctcacg cgcatcgcca aggacatgga ggacagtgtc ccgttggatt gttcccgcca    780
```

```
cctgggcgtg gcggcagggg ccattctggc gctgctctcg ttcctcaccc cgctggcttt      840
cctgctgctg cctccactgc tgtggcggga ggagctggag ccgtgtggga cggcctgtga      900
gggcctcttc atctccgtgg ccttcaagct gctcatcctg ctgttgggca gctgggctct      960
gttcttccgc cggcccaagg cctcactgcc ccgagtcttc gtgttacgag ctctgctcat     1020
ggtgcttgtc ttcctgctgg ttatttccta ttggctcttc tacggtgtgc gcatcttgga     1080
cgcccgggag cggagctacc agggcgtggt tcagtttgcc gtttctctag tggatgcttt     1140
actcttcgtg cactatctgg ccgtagttct gctggagctc cgtcagctcc agccccagtt     1200
cacactcaag gtcgtgcgat ccacagatgg ggccagccgc ttctacaatg tcggccatct     1260
cagcatccag cgagtggcag tgtggatcct ggagaagtat accatgact  ccctgtcta     1320
caaccccgcc ctcctcaacc tgcccaagtc cgtcctggcc aagaaagtgt ctggcttcaa     1380
ggtgtattct ctcggagagg aaaatagcac caataactcc acgggccaat caagggctgt     1440
gatcgcggct gcggcacgga ggcgcgacaa cagccacaat gagtactact acgaggaagc     1500
cgagcatgag cgcagagtgc gcaagcgcag ggccaggctc gtggtggctg tggaggaggc     1560
cttcacgcac attaagcggc tgcaggaaga ggagcagaag aaccccaggg aggtgatgga     1620
cccccgggaa gcagcccaag cgatctttgc atccatggct cgtgccatgc agaagtacct     1680
tcgcaccacc aaacagcagc cttaccatac catggagagc atccttcagc acctggagtt     1740
ctgcattacc cacgacatga cgcccaaggc cttcctggag cgatatttgg ctgctggacc     1800
caccatccag taccacaagg aacgttggct ggccaaacag tggaccttgg tgagcgagga     1860
gccggtgacc aatgggctta aggatggcat cgtgttcctc ttgaagcgcc aggacttcag     1920
cttggtagtg agcaccaaga aggtgcccct tctcaaactc tctgaggaat tgtggatcc       1980
caagtcacat aagttcgtca tgcggctgca gtcggagacc tctgtgtgac ttttgcagca     2040
gccgcggagg agggatgtgg gggttcctg  cggagtggga ggggcttggt tctctggccc     2100
tgacacattt ctgccagtcc tacttcctct tgctcttgtt tgttttgtt  ttttgttttt     2160
tgtttttttt tttacttgaa ttaacttatc ctgtacccag tctcccctct tcctcagttt     2220
ttcccatctg gaaatctgga gataaatctt gttaacaata                           2260
```

<210> SEQ ID NO 10
<211> LENGTH: 521
<212> TYPE: PRT
<213> ORGANISM: Mus musculus
<220> FEATURE:
<221> NAME/KEY: MISC_FEATURE
<222> LOCATION: (1)..(521)
<223> OTHER INFORMATION: Mouse Vangl2 Protein

<400> SEQUENCE: 10

```
Met Asp Thr Glu Ser Gln Tyr Ser Gly Tyr Ser Tyr Lys Ser Gly His
  1               5                  10                  15

Ser Arg Ser Ser Arg Lys His Arg Asp Arg Arg Asp Arg His Arg Ser
                 20                  25                  30

Lys Ser Arg Asp Gly Ser Arg Gly Asp Lys Ser Val Thr Ile Gln Ala
             35                  40                  45

Pro Gly Glu Pro Leu Leu Asp Asn Glu Ser Thr Arg Gly Asp Glu Arg
         50                  55                  60

Asp Asp Asn Trp Gly Glu Thr Thr Val Val Thr Gly Thr Ser Glu
 65                  70                  75                  80

His Ser Ile Ser His Asp Asp Leu Thr Arg Ile Ala Lys Asp Met Glu
                 85                  90                  95
```

-continued

```
Asp Ser Val Pro Leu Asp Cys Ser Arg His Leu Gly Val Ala Ala Gly
            100                 105                 110

Ala Ile Leu Ala Leu Leu Ser Phe Leu Thr Pro Leu Ala Phe Leu Leu
            115                 120                 125

Leu Pro Pro Leu Leu Trp Arg Glu Leu Glu Pro Cys Gly Thr Ala
130                 135                 140

Cys Glu Gly Leu Phe Ile Ser Val Ala Phe Lys Leu Leu Ile Leu Leu
145                 150                 155                 160

Leu Gly Ser Trp Ala Leu Phe Phe Arg Arg Pro Lys Ala Ser Leu Pro
                165                 170                 175

Arg Val Phe Val Leu Arg Ala Leu Leu Met Val Leu Val Phe Leu Leu
            180                 185                 190

Val Ile Ser Tyr Trp Leu Phe Tyr Gly Val Arg Ile Leu Asp Ala Arg
            195                 200                 205

Glu Arg Ser Tyr Gln Gly Val Val Gln Phe Ala Val Ser Leu Val Asp
        210                 215                 220

Ala Leu Leu Phe Val His Tyr Leu Ala Val Val Leu Leu Glu Leu Arg
225                 230                 235                 240

Gln Leu Gln Pro Gln Phe Thr Leu Lys Val Val Arg Ser Thr Asp Gly
                245                 250                 255

Ala Ser Arg Phe Tyr Asn Val Gly His Leu Ser Ile Gln Arg Val Ala
            260                 265                 270

Val Trp Ile Leu Glu Lys Tyr Tyr His Asp Phe Pro Val Tyr Asn Pro
            275                 280                 285

Ala Leu Leu Asn Leu Pro Lys Ser Val Leu Ala Lys Lys Val Ser Gly
            290                 295                 300

Phe Lys Val Tyr Ser Leu Gly Glu Glu Asn Ser Thr Asn Asn Ser Thr
305                 310                 315                 320

Gly Gln Ser Arg Ala Val Ile Ala Ala Ala Arg Arg Arg Asp Asn
                325                 330                 335

Ser His Asn Glu Tyr Tyr Tyr Glu Glu Ala Glu His Glu Arg Arg Val
            340                 345                 350

Arg Lys Arg Arg Ala Arg Leu Val Val Ala Val Glu Glu Ala Phe Thr
            355                 360                 365

His Ile Lys Arg Leu Gln Glu Glu Gln Lys Asn Pro Arg Glu Val
370                 375                 380

Met Asp Pro Arg Glu Ala Ala Gln Ala Ile Phe Ala Ser Met Ala Arg
385                 390                 395                 400

Ala Met Gln Lys Tyr Leu Arg Thr Thr Lys Gln Pro Tyr His Thr
                405                 410                 415

Met Glu Ser Ile Leu Gln His Leu Glu Phe Cys Ile Thr His Asp Met
            420                 425                 430

Thr Pro Lys Ala Phe Leu Glu Arg Tyr Leu Ala Ala Gly Pro Thr Ile
            435                 440                 445

Gln Tyr His Lys Glu Arg Trp Leu Ala Lys Gln Trp Thr Leu Val Ser
        450                 455                 460

Glu Glu Pro Val Thr Asn Gly Leu Lys Asp Gly Ile Val Phe Leu Leu
465                 470                 475                 480

Lys Arg Gln Asp Phe Ser Leu Val Val Ser Thr Lys Lys Val Pro Phe
                485                 490                 495

Phe Lys Leu Ser Glu Glu Phe Val Asp Pro Lys Ser His Lys Phe Val
            500                 505                 510
```

```
Met Arg Leu Gln Ser Glu Thr Ser Val
        515                 520
```

<210> SEQ ID NO 11
<211> LENGTH: 5415
<212> TYPE: DNA
<213> ORGANISM: Homo sapiens
<220> FEATURE:
<221> NAME/KEY: misc_feature
<222> LOCATION: (1)..(5415)
<223> OTHER INFORMATION: Human Vangl2 cDNA

<400> SEQUENCE: 11

| | | | | | |
|---|---|---|---|---|---|
| ggatcccgat | ctgattcctg | atccttgatt | ccttgatcct | tggtcccgcc | atgggagcct | 60 |
| gagcgcccc | tattccccc | tggccccag | ccccggggc | cttgagggg | aagaggcagc | 120 |
| ggtctgggac | ggagcagggg | gtgaccagac | tcaagaaccc | ccccctcaac | atccccatc | 180 |
| gcgcgcgctg | cctgtccagg | agcgccgagt | tcggagcgac | ccggagcgct | gcggatacaa | 240 |
| aggcgacggg | ccgagcgggg | cgcccgcgga | gcccacccgg | cagttcgcag | cggcgggagc | 300 |
| gtcgctggat | tttctctgag | acaagcccac | ccgtccagca | aaatagagtc | cctcagggtg | 360 |
| acagttgact | tcctgaaggt | gcctcttggc | ctaaagaagc | cggtgctgaa | ggaggtggct | 420 |
| gtggggcccc | ccaagaggcc | ccagcctgcg | gccctggagc | gctacaaggc | gcggcgttca | 480 |
| gacgccatgg | acaccgagtc | ccagtactcg | ggctattcct | acaagtcggg | ccactcccgc | 540 |
| agctcccgca | agcacaggga | ccgccgggac | cgacaccgct | ctaagagtcg | agatggggc | 600 |
| cgaggggaca | agtcggtgac | aatccaggct | cccggggagc | ccctgctgga | caatgagtcc | 660 |
| acacgagggg | atgagcggga | tgacaactgg | ggggaaacga | cgacagtagt | aacgggcacc | 720 |
| tcagagcaca | gcatctccca | tgatgacctc | acacgcatcg | ccaaggacat | ggaggacagt | 780 |
| gtccctctgg | actgctcccg | tcacctgggt | gtggcagcgg | gggccaccct | ggcactgctg | 840 |
| tctttcctca | cgcctctggc | cttcctgctg | ctgcccccac | tgctgtggcg | ggaggagctg | 900 |
| gagccttgcg | ggacggcctg | cgagggcctc | ttcatctctg | tcgccttcaa | gctgctcatc | 960 |
| ctgctactgg | gcagctgggc | tctgttcttc | cgccggccca | aggcctcgct | gccccgcgtc | 1020 |
| tttgtgctgc | gtgccctgct | tatggtgctg | gttttcctgc | tcgtggtctc | ctactggctc | 1080 |
| ttctatggtg | tgcgcatcct | ggatgctcgg | gagcgcagct | accagggcgt | ggtgcagttc | 1140 |
| gccgtgtcg | tggtggacgc | ccttcttttc | gtgcactacc | tggccgtggt | cctgctggag | 1200 |
| ctgcgccagc | tccagcctca | gttcacgctc | aaggtcgtgc | gctccaccga | cggcgccagc | 1260 |
| cgcttctaca | cgttggcca | tctcagcatc | cagcgcgtgg | cagtgtggat | cctggagaag | 1320 |
| tattaccatg | acttccctgt | ctacaaccct | gccctcctca | acctgccaa | gtccgtcctg | 1380 |
| gccaagaaag | tgtctggctt | caaggtgtat | tccctcggag | aggaaaacag | caccaacaac | 1440 |
| tccactggcc | agtctcgggc | tgtgattgca | gcggcagctc | ggaggcggga | caacagtcac | 1500 |
| aatgagtact | actatgagga | ggctgagcat | gagcgaaggg | tgcgcaagag | gagggccagg | 1560 |
| cttgtagtgg | cggtggagga | ggccttcact | cacattaagc | ggctgcagga | agaggagcag | 1620 |
| aaaaacccca | gggaggtgat | ggaccccgg | gaggcagccc | aagccatctt | tgcatccatg | 1680 |
| gcccgtgcca | tgcagaagta | ccttcggacc | accaagcag | agcccctacca | caccatggag | 1740 |
| agcatcctgc | agcaccttga | attctgcatc | acgcatgaca | tgacgcccaa | ggccttcttg | 1800 |
| gagcgatact | tggcggctgg | acctaccatc | cagtaccaca | aggaacgctg | gctgccaaa | 1860 |
| cagtggacat | tggtgagcga | ggagccggtg | accaacggcc | tcaaggatgg | catcgttttc | 1920 |

```
ctcttaaaac gccaggactt cagcctggtg gtcagcacca agaaggtccc attcttcaaa    1980
ctctccgagg aatttgtgga tcccaagtca cacaagtttg tcatgaggct gcagtctgag    2040
acctcagtgt gactgtgcaa cagcaggggg agtgggaaac tctgggggt cctgagggg     2100 tgggagggg cttggttctc aggcccagcc acattcctgc cacccttctt cttcttgctc    2160 ttttttttt acttgaatta acgcacccc accttctctc ctcgcttctt ccttatttta     2220
ccccatgtga acctggagag accatcctgc tgtcaacagt acctgggaag gactcccacc    2280
tcaccaacaa cttttgtatt actctaggcc ctgcaggaat cagtgcctct ctccctcttc    2340 tttcctagt ctttccccag attacagtct ctcctgaaag ggcacagggc cctgctgatt     2400
gtactttccc ctcctgagcc ccgactcaca aatccaagtt cttaaaacat ttctcttcag    2460
tggcccaaca gggtttctct ggggcacatg gacatgactc cagagagcca cagtgccaaa    2520
ctcctccagg gcagcaactg gccctcctgt ccctcacccc agccacaaca aaccctgggt    2580
tctagggcag ggatactcct gccacacagc ccgagttaga aatctccttg ctaggagcat    2640
ttgcttccac atatatttag agcaaagaag gatcccatcc ttttcccaga aatctccacc    2700
taatgttttt ggtttgtatg gtcacgtgac cataggcaac cacgtggaaa ccctctgtga    2760
ccacttttcc agggacttag gggaaggtac cttttcttcca atgtgtcttc ctaggcagcc    2820
cctgaggagg agggctgaat agatccctga ggttttggag agaccccat cactgactcc     2880 tgctccctaa ccctacccctc acttttcgtcc ccgctcttcc cagtgaagga tggtatgtag   2940
actcctgtac agacatagtg gcttgcagac cctgacccag cccctgtggt cttagacaaa    3000
tgtttttatt tttgtcacca gccacccctg tcctgccgcc ttctctcgac tccagagacc    3060
tgttgcctca tctcttttgg ggaagagccg gcagctcctc ctcatcccct gccttaagtc    3120
cagttctttg cctcagggt ctcgtttcct tggccttcca gggtccccac cccttttctc     3180
cctgcctgat tctctgagct ctgggctccg tctgtattgg gttgaggggc aaggattact    3240
gccttttgta ggtacttcac ccctcacccc attttagctt ccatagtctt tgcaccaaat    3300
ccaaattctt gataatttag atctcatttt gagcaaaatt tgctggccct ctaataaata    3360
ttttcaatat aaatctgagc ctttgactca gacattttg ccaaggagag tagaattagg     3420
aagtacccat atacatccag ccaggatcca catggaggac cttctgatg gctgcaatga     3480 ctaggccatt cctctgagta actcacagtg tccttttgta ggcccttctt ttccctgaaa    3540
gactggttgg tacttacctt gcagagcaca tcctgggata agatccccag tgtctcccct    3600
gggaggctcc ccctctgtgt agcaccagcc ctgggaatga tggagcctag tgatcggggt    3660
ttctcctgct gtccttttctg caaaagttca cttgtttacc caccgcatgc tagagaggag    3720
ctcattggcc aatgcttacc ttgtccccaa aggggtgggt tgtggagctc acttaggcag    3780
ggcctctggc tggggccagg gttatgagat aggcctgtat gaaatatgtc ctgttctggg    3840
ggtctgtctc ttttcttctc ttcaaaaact ttgtgtcaga gagtcccttc tgagtcacat    3900
aaatacctca ctatcctgga aaacagggcc tggatgtga ctgggtcat tgcctttgtg      3960 gacaggatgg agtgtggtgt ggtctgagga gcaggttggg gtgggggaga gggaaaggat    4020
ttgggatctt agttgctgcc ctaggttagg ggctggggag tgtttatttt aagatcctgc    4080
catgttttta atcactgtga tttttttttc attcccctttt cctaaaaaaa attttttcc    4140 tccaactctc taagcactaa gggctgtgcc tgagaatggt agcatttggg tcttttgctt    4200
cagaactgtg gtatctttgt cttttttcat tattattatt attattatta ttattattac   4260
tattgttttt taaaatgtca ggatgaattg tcagacatat ggccatgtgt ttgtcctctg    4320
```

-continued

```
cttctcccct gtgggaagtt gtctccatgc tgtgaactgc tgtggggtgt gcagctgact    4380
cagtccctct gagcagtttc cccactgtgt ctgtcccatc atgcgctgga tctgctcatt    4440
ctcctgctgt gggggtatgc ccacctctta ccccttgac accatagggc tgctgtggct    4500
gggcctcacc agcactgtct tttgtgtgac tcatggcatc ctcgttcatc cccaccgtgc    4560
ctagcaggcc ttccttttca ccacctcgga acgcttgcct ttcctccctc cacaacagga    4620
cgctgtgcct cagtccttca cctacctcgc cactctgcca ctgtcccat ggtcctttc     4680 tcctaaactg gtctttgtgc tctctttgtt ttttcttatt tccctcttgt ctctcatttt    4740
ttcttcccat tcccctccca tttcagccct taacttttct cttcccatc tccactcagt    4800 attccaatgg caaaccctga tgatgtaaca cctgcgatga cacatcggac tctccggaac   4860
tttctcatct gacacgtctt tttcccaggg ttcgtacttc tcctccattg gtcccaggct    4920
aactcccctg ttcctctgtg gtgtctgtca gtccgtctgt cttctctttc ctctgcctt    4980 cccacagggc agtatctgct gatggattca gtcctggtgt gtgattgttg tgatttgttc    5040
ttccgtgcgc aaaaggaaga gggcttttg agtcccttcc aagtgagatt gtaaatgtag    5100
aattttccac tgttggatct agattttttt tcctttttt tgggggggtg gggttacaga    5160
gctgagacct tgtgcatgca tgtagaaaat tgtaaaatgt aaattttttt taatatataa    5220
aaagcttgtt tctacagttt gcagtggatc taaacattac ggcaattta ggatttttt    5280 cttaaacata ggaactaaaa ctgtacaaat ttttttata taaaataaag acatttgact    5340
tttgtgggaa aaaaaaaa aaaaaaaaa aaaaaaaaa aaaaaaaaa aaaaaaaaa         5400 aaaaaaaaa aaaa                                                    5415
```

<210> SEQ ID NO 12
<211> LENGTH: 521
<212> TYPE: PRT
<213> ORGANISM: Homo sapiens
<220> FEATURE:
<221> NAME/KEY: MISC_FEATURE
<222> LOCATION: (1)..(521)
<223> OTHER INFORMATION: Human Vangl2 Protein

<400> SEQUENCE: 12

```
Met Asp Thr Glu Ser Gln Tyr Ser Gly Tyr Ser Tyr Lys Ser Gly His
1               5                   10                  15

Ser Arg Ser Ser Arg Lys His Arg Asp Arg Arg Asp Arg His Arg Ser
                20                  25                  30

Lys Ser Arg Asp Gly Gly Arg Gly Asp Lys Ser Val Thr Ile Gln Ala
            35                  40                  45

Pro Gly Glu Pro Leu Leu Asp Asn Glu Ser Thr Arg Gly Asp Glu Arg
        50                  55                  60

Asp Asp Asn Trp Gly Glu Thr Thr Thr Val Val Thr Gly Thr Ser Glu
65                  70                  75                  80

His Ser Ile Ser His Asp Asp Leu Thr Arg Ile Ala Lys Asp Met Glu
                85                  90                  95

Asp Ser Val Pro Leu Asp Cys Ser Arg His Leu Gly Val Ala Ala Gly
            100                 105                 110

Ala Thr Leu Ala Leu Leu Ser Phe Leu Thr Pro Leu Ala Phe Leu Leu
        115                 120                 125

Leu Pro Pro Leu Leu Trp Arg Glu Gly Leu Glu Pro Cys Gly Thr Ala
    130                 135                 140

Cys Glu Gly Leu Phe Ile Ser Val Ala Phe Lys Leu Leu Ile Leu Leu
```

Leu Gly Ser Trp Ala Leu Phe Phe Arg Arg Pro Lys Ala Ser Leu Pro
145                 150                 155                 160

Arg Val Phe Val Leu Arg Ala Leu Leu Met Val Leu Val Phe Leu Leu
            165                 170                 175

Val Val Ser Tyr Trp Leu Phe Tyr Gly Val Arg Ile Leu Asp Ala Arg
        180                 185                 190

Glu Arg Ser Tyr Gln Gly Val Val Gln Phe Ala Val Ser Leu Val Asp
    195                 200                 205

Ala Leu Leu Phe Val His Tyr Leu Ala Val Leu Leu Glu Leu Arg
210                 215                 220

Gln Leu Gln Pro Gln Phe Thr Leu Lys Val Val Arg Ser Thr Asp Gly
225                 230                 235                 240

Ala Ser Arg Phe Tyr Asn Val Gly His Leu Ser Ile Gln Arg Val Ala
    245                 250                 255

Val Trp Ile Leu Glu Lys Tyr Tyr His Asp Phe Pro Val Tyr Asn Pro
        260                 265                 270

Ala Leu Leu Asn Leu Pro Lys Ser Val Leu Ala Lys Lys Val Ser Gly
    275                 280                 285

Phe Lys Val Tyr Ser Leu Gly Glu Glu Asn Ser Thr Asn Asn Ser Thr
290                 295                 300

Gly Gln Ser Arg Ala Val Ile Ala Ala Ala Arg Arg Arg Asp Asn
305                 310                 315                 320

Ser His Asn Glu Tyr Tyr Tyr Glu Glu Ala Glu His Glu Arg Arg Val
    325                 330                 335

Arg Lys Arg Arg Ala Arg Leu Val Val Ala Val Glu Glu Ala Phe Thr
        340                 345                 350

His Ile Lys Arg Leu Gln Glu Glu Glu Gln Lys Asn Pro Arg Glu Val
    355                 360                 365

Met Asp Pro Arg Glu Ala Ala Gln Ala Ile Phe Ala Ser Met Ala Arg
370                 375                 380

Ala Met Gln Lys Tyr Leu Arg Thr Thr Lys Gln Gln Pro Tyr His Thr
385                 390                 395                 400

Met Glu Ser Ile Leu Gln His Leu Glu Phe Cys Ile Thr His Asp Met
    405                 410                 415

Thr Pro Lys Ala Phe Leu Glu Arg Tyr Leu Ala Ala Gly Pro Thr Ile
        420                 425                 430

Gln Tyr His Lys Glu Arg Trp Leu Ala Lys Gln Trp Thr Leu Val Ser
    435                 440                 445

Glu Glu Pro Val Thr Asn Gly Leu Lys Asp Gly Ile Val Phe Leu Leu
450                 455                 460

Lys Arg Gln Asp Phe Ser Leu Val Val Ser Thr Lys Lys Val Pro Phe
465                 470                 475                 480

Phe Lys Leu Ser Glu Glu Phe Val Asp Pro Lys Ser His Lys Phe Val
    485                 490                 495

Met Arg Leu Gln Ser Glu Thr Ser Val
        500                 505                 510

515                 520

<210> SEQ ID NO 13
<211> LENGTH: 20
<212> TYPE: DNA
<213> ORGANISM: Artificial Sequence
<220> FEATURE:
<223> OTHER INFORMATION: PCR Primer Axin2_F

<400> SEQUENCE: 13
aagagaagcg acccagtcaa				20

<210> SEQ ID NO 14
<211> LENGTH: 20
<212> TYPE: DNA
<213> ORGANISM: Artificial Sequence
<220> FEATURE:
<223> OTHER INFORMATION: PCR Primer Axin2_R

<400> SEQUENCE: 14
ctgcgatgca tctctctctg				20

<210> SEQ ID NO 15
<211> LENGTH: 20
<212> TYPE: DNA
<213> ORGANISM: Artificial Sequence
<220> FEATURE:
<223> OTHER INFORMATION: PCR Primer Celsr1_F

<400> SEQUENCE: 15
ggggactact gcgagactga				20

<210> SEQ ID NO 16
<211> LENGTH: 20
<212> TYPE: DNA
<213> ORGANISM: Artificial Sequence
<220> FEATURE:
<223> OTHER INFORMATION: PCR Primer Celsr1_R

<400> SEQUENCE: 16
cccgtttttg catactccac				20

<210> SEQ ID NO 17
<211> LENGTH: 20
<212> TYPE: DNA
<213> ORGANISM: Artificial Sequence
<220> FEATURE:
<223> OTHER INFORMATION: PCR Primer Celsr2_F

<400> SEQUENCE: 17
ccgaggtgga cctctgttac				20

<210> SEQ ID NO 18
<211> LENGTH: 20
<212> TYPE: DNA
<213> ORGANISM: Artificial Sequence
<220> FEATURE:
<223> OTHER INFORMATION: PCR Primer Celsr2_R

<400> SEQUENCE: 18
ccaccaacag gttgacacag				20

<210> SEQ ID NO 19
<211> LENGTH: 20
<212> TYPE: DNA
<213> ORGANISM: Artificial Sequence
<220> FEATURE:
<223> OTHER INFORMATION: PCR Primer Celsr3_F

<400> SEQUENCE: 19
atgacccgga tgtctctgac				20

<210> SEQ ID NO 20
<211> LENGTH: 20

```
<212> TYPE: DNA
<213> ORGANISM: Artificial Sequence
<220> FEATURE:
<223> OTHER INFORMATION: PCR Primer Celsr3_R

<400> SEQUENCE: 20
actcctccgt gatgatgacc                                              20

<210> SEQ ID NO 21
<211> LENGTH: 20
<212> TYPE: DNA
<213> ORGANISM: Artificial Sequence
<220> FEATURE:
<223> OTHER INFORMATION: PCR Primer Dvl1_F

<400> SEQUENCE: 21
cttaccagga ccctggcttc                                              20

<210> SEQ ID NO 22
<211> LENGTH: 20
<212> TYPE: DNA
<213> ORGANISM: Artificial Sequence
<220> FEATURE:
<223> OTHER INFORMATION: PCR Primer Dvl1_R

<400> SEQUENCE: 22
cctgacttcg agggctactg                                              20

<210> SEQ ID NO 23
<211> LENGTH: 20
<212> TYPE: DNA
<213> ORGANISM: Artificial Sequence
<220> FEATURE:
<223> OTHER INFORMATION: PCR Primer Dvl1_F

<400> SEQUENCE: 23
tatgtcttcg gggacctcag                                              20

<210> SEQ ID NO 24
<211> LENGTH: 20
<212> TYPE: DNA
<213> ORGANISM: Artificial Sequence
<220> FEATURE:
<223> OTHER INFORMATION: PCR Primer Dvl2_R

<400> SEQUENCE: 24
cgaagaaagc tcgtggtagg                                              20

<210> SEQ ID NO 25
<211> LENGTH: 20
<212> TYPE: DNA
<213> ORGANISM: Artificial Sequence
<220> FEATURE:
<223> OTHER INFORMATION: PCR Primer Dvl3_F

<400> SEQUENCE: 25
gcctatggct ttcccttacc                                              20

<210> SEQ ID NO 26
<211> LENGTH: 20
<212> TYPE: DNA
<213> ORGANISM: Artificial Sequence
<220> FEATURE:
<223> OTHER INFORMATION: PCR Primer Dvl3_R

<400> SEQUENCE: 26
```
acttggagtc cccagctttt                                               20

<210> SEQ ID NO 27
<211> LENGTH: 20
<212> TYPE: DNA
<213> ORGANISM: Artificial Sequence
<220> FEATURE:
<223> OTHER INFORMATION: PCR Primer Fzd1_F

<400> SEQUENCE: 27
caaggtttac gggctcatgt                                               20

<210> SEQ ID NO 28
<211> LENGTH: 20
<212> TYPE: DNA
<213> ORGANISM: Artificial Sequence
<220> FEATURE:
<223> OTHER INFORMATION: PCR Primer Fzd1_R

<400> SEQUENCE: 28
gtaacagccg gacaggaaaa                                               20

<210> SEQ ID NO 29
<211> LENGTH: 20
<212> TYPE: DNA
<213> ORGANISM: Artificial Sequence
<220> FEATURE:
<223> OTHER INFORMATION: PCR Primer Fzd3_F

<400> SEQUENCE: 29
ccttgaggat gtgccaagat                                               20

<210> SEQ ID NO 30
<211> LENGTH: 20
<212> TYPE: DNA
<213> ORGANISM: Artificial Sequence
<220> FEATURE:
<223> OTHER INFORMATION: PCR Primer Fzd3_R

<400> SEQUENCE: 30
gctataggca cgctgacaca                                               20

<210> SEQ ID NO 31
<211> LENGTH: 20
<212> TYPE: DNA
<213> ORGANISM: Artificial Sequence
<220> FEATURE:
<223> OTHER INFORMATION: PCR Primer Fzd4_F

<400> SEQUENCE: 31
aacctcggct acaacgtgac                                               20

<210> SEQ ID NO 32
<211> LENGTH: 20
<212> TYPE: DNA
<213> ORGANISM: Artificial Sequence
<220> FEATURE:
<223> OTHER INFORMATION: PCR Primer Fzd4_R

<400> SEQUENCE: 32
tggcacataa accgaacaaa                                               20

<210> SEQ ID NO 33
<211> LENGTH: 20
<212> TYPE: DNA
<213> ORGANISM: Artificial Sequence
<220> FEATURE:
<223> OTHER INFORMATION: PCR Primer Fzd6_F

<400> SEQUENCE: 33
aatggacact tttggcatcc                                                20

<210> SEQ ID NO 34
<211> LENGTH: 20
<212> TYPE: DNA
<213> ORGANISM: Artificial Sequence
<220> FEATURE:
<223> OTHER INFORMATION: PCR Primer Fzdr6_R

<400> SEQUENCE: 34
aggggcacac tgttcaattc                                                20

<210> SEQ ID NO 35
<211> LENGTH: 20
<212> TYPE: DNA
<213> ORGANISM: Artificial Sequence
<220> FEATURE:
<223> OTHER INFORMATION: PCR Primer Fzdr7_F

<400> SEQUENCE: 35
gcttcctagg tgagcgtgac                                                20

<210> SEQ ID NO 36
<211> LENGTH: 20
<212> TYPE: DNA
<213> ORGANISM: Artificial Sequence
<220> FEATURE:
<223> OTHER INFORMATION: PCR Primer Fzd7_R

<400> SEQUENCE: 36
aacccgacag gaagatgatg                                                20

<210> SEQ ID NO 37
<211> LENGTH: 20
<212> TYPE: DNA
<213> ORGANISM: Artificial Sequence
<220> FEATURE:
<223> OTHER INFORMATION: PCR Primer Gapdh_F

<400> SEQUENCE: 37
atgccagtga gcttcccgtc                                                20

<210> SEQ ID NO 38
<211> LENGTH: 20
<212> TYPE: DNA
<213> ORGANISM: Artificial Sequence
<220> FEATURE:
<223> OTHER INFORMATION: PCR Primer Gapdh_R

<400> SEQUENCE: 38
catcaccatc ttccaggagc                                                20

<210> SEQ ID NO 39
<211> LENGTH: 22
<212> TYPE: DNA
<213> ORGANISM: Artificial Sequence
<220> FEATURE:
<223> OTHER INFORMATION: PCR Primer Myf5_F

<400> SEQUENCE: 39
tgaaggatgg acatgacgga cg                                             22

<210> SEQ ID NO 40
<211> LENGTH: 22
<212> TYPE: DNA
<213> ORGANISM: Artificial Sequence
<220> FEATURE:
<223> OTHER INFORMATION: PCR Primer Myf5_R

<400> SEQUENCE: 40
ttgtgtgctc cgaaggctgc ta                                           22

<210> SEQ ID NO 41
<211> LENGTH: 20
<212> TYPE: DNA
<213> ORGANISM: Artificial Sequence
<220> FEATURE:
<223> OTHER INFORMATION: PCR Primer MyoD_F

<400> SEQUENCE: 41
tacccaaggt ggagatcctg                                              20

<210> SEQ ID NO 42
<211> LENGTH: 20
<212> TYPE: DNA
<213> ORGANISM: Artificial Sequence
<220> FEATURE:
<223> OTHER INFORMATION: PCR Primer MyoD_R

<400> SEQUENCE: 42
catcatgcca tcagagcagt                                              20

<210> SEQ ID NO 43
<211> LENGTH: 20
<212> TYPE: DNA
<213> ORGANISM: Artificial Sequence
<220> FEATURE:
<223> OTHER INFORMATION: PCR Primer Myogenin_F

<400> SEQUENCE: 43
gaaagtgaat gaggccttcg                                              20

<210> SEQ ID NO 44
<211> LENGTH: 20
<212> TYPE: DNA
<213> ORGANISM: Artificial Sequence
<220> FEATURE:
<223> OTHER INFORMATION: PCR Primer Myogenin_R

<400> SEQUENCE: 44
acgatggacg taagggagtg                                              20

<210> SEQ ID NO 45
<211> LENGTH: 20
<212> TYPE: DNA
<213> ORGANISM: Artificial Sequence
<220> FEATURE:
<223> OTHER INFORMATION: PCR Primer Notch3_F

<400> SEQUENCE: 45
gatgacacat cagccagcat                                              20

<210> SEQ ID NO 46
<211> LENGTH: 20
<212> TYPE: DNA
<213> ORGANISM: Artificial Sequence
<220> FEATURE:
<223> OTHER INFORMATION: PCR Primer Notch3_R

```
<400> SEQUENCE: 46
gagcggttcc tgatgagaat                                                20

<210> SEQ ID NO 47
<211> LENGTH: 20
<212> TYPE: DNA
<213> ORGANISM: Artificial Sequence
<220> FEATURE:
<223> OTHER INFORMATION: PCR Primer Pax7_F

<400> SEQUENCE: 47
ctggatgagg gctcagatgt                                                20

<210> SEQ ID NO 48
<211> LENGTH: 20
<212> TYPE: DNA
<213> ORGANISM: Artificial Sequence
<220> FEATURE:
<223> OTHER INFORMATION: PCR Primer Pax7_R

<400> SEQUENCE: 48
ggttagctcc tgcctgctta                                                20

<210> SEQ ID NO 49
<211> LENGTH: 20
<212> TYPE: DNA
<213> ORGANISM: Artificial Sequence
<220> FEATURE:
<223> OTHER INFORMATION: PCR Primer Tcf7_F

<400> SEQUENCE: 49
ccccagcttt ctccactcta                                                20

<210> SEQ ID NO 50
<211> LENGTH: 20
<212> TYPE: DNA
<213> ORGANISM: Artificial Sequence
<220> FEATURE:
<223> OTHER INFORMATION: PCR Primer Tcf7_R

<400> SEQUENCE: 50
tcacagtatg ggggagctgt                                                20

<210> SEQ ID NO 51
<211> LENGTH: 20
<212> TYPE: DNA
<213> ORGANISM: Artificial Sequence
<220> FEATURE:
<223> OTHER INFORMATION: PCR Primer Vangl1_F

<400> SEQUENCE: 51
gcactaccac agcatggaga                                                20

<210> SEQ ID NO 52
<211> LENGTH: 20
<212> TYPE: DNA
<213> ORGANISM: Artificial Sequence
<220> FEATURE:
<223> OTHER INFORMATION: PCR Primer Vangl1_R

<400> SEQUENCE: 52
attgaccacg aggctgaagt                                                20

<210> SEQ ID NO 53
```

-continued

```
<211> LENGTH: 20
<212> TYPE: DNA
<213> ORGANISM: Artificial Sequence
<220> FEATURE:
<223> OTHER INFORMATION: PCR Primer Vangl2_F

<400> SEQUENCE: 53
ccccagttca cactcaaggt                                               20

<210> SEQ ID NO 54
<211> LENGTH: 19
<212> TYPE: DNA
<213> ORGANISM: Artificial Sequence
<220> FEATURE:
<223> OTHER INFORMATION: PCR Primer Vangl2_R

<400> SEQUENCE: 54
acttgggcag gttgaggag                                                19

<210> SEQ ID NO 55
<211> LENGTH: 27
<212> TYPE: DNA
<213> ORGANISM: Artificial Sequence
<220> FEATURE:
<223> OTHER INFORMATION: PCR Pimer Yfp_F

<400> SEQUENCE: 55
gcacgacttc ttcaagtccg ccatgcc                                       27

<210> SEQ ID NO 56
<211> LENGTH: 27
<212> TYPE: DNA
<213> ORGANISM: Artificial Sequence
<220> FEATURE:
<223> OTHER INFORMATION: PCR Primer Yfp_R

<400> SEQUENCE: 56
gcggatcttg aagttcacct tgatgcc                                       27
```

COMPOSITIONS AND METHODS FOR MODULATING STEM CELLS AND USES THEREOF

CROSS REFERENCE TO RELATED APPLICATIONS

This application is a continuation of U.S. patent application Ser. No. 13/266,428, filed Apr. 30, 2012, which is a U.S. National Entry of PCT Patent Application No. PCT/CA2010/000601, filed Apr. 27, 2010, which claims the benefit of priority of U.S. Patent Application Ser. No. 61/172,832, filed Apr. 27, 2009, the contents of which are incorporated herein by reference in their entirety.

FIELD OF THE INVENTION

The present invention relates generally to compositions and methods for modulating stem cells, in particular, stem cell division symmetry, and uses thereof.

BACKGROUND OF THE INVENTION

Stem cells are undifferentiated, or immature, cells that are capable of giving rise to multiple specialized cell types and, ultimately, to terminally differentiated cells. Most adult stem cells are lineage-restricted and are generally referred to by their tissue origin. Unlike any other cells, stem cells are able to renew themselves such that a virtually endless supply of mature cell types can be generated when needed over the lifetime of an organism. Due to this capacity for self-renewal, stem cells are therapeutically useful for the formation, regeneration, repair and maintenance of tissues. To ensure self-renewal, stem cells undergo two types of cell division. Symmetric division gives rise to two identical daughter cells, both endowed with stem cell properties, and leads to expansion of the stem cell population. Asymmetric division, on the other hand, produces one stem cell and one progenitor cell with limited self-renewal potential. Progenitors are transient amplifying cells that can go through several rounds of cell division, i.e. proliferation, before terminally differentiating into a mature cell. In adult organisms, stem cells and progenitor cells act as a repair system for the tissues of the body, replenish specialized cells, and maintain the normal turnover of regenerative organs, such as blood, skin or intestinal tissues.

It has recently been determined that satellite cells represent a heterogeneous population composed of stem cells and small mononuclear progenitor cells found in mature muscle tissue (Kuang et al., 2007). Satellite cells in adult skeletal muscle are located in small depressions between the sarcolemma of their host myofibers and the basal lamina. Satellite cells are involved in the normal growth of muscle, as well as the regeneration of injured or diseased tissue. In undamaged muscle, the majority of satellite cells are quiescent, meaning they neither differentiate nor undergo cell division. Satellite cells express a number of distinctive genetic markers, including the paired-box transcription factor Pax7, which plays a central regulatory role in satellite cell function and survival (Kuang et al., 2006; Seale et al., 2000). Pax7 can thus be used as a marker of satellite cells.

Upon damage, such as physical trauma or strain, repeated exercise, or in disease, satellite cells become activated, proliferate and give rise to a population of transient amplifying progenitors, which are myogenic precursors cells (myoblasts) expressing myogenic regulatory factors (MRF), such as MyoD and Myf5. In the course of the regeneration process, myoblasts undergo multiple rounds of division before committing to terminal differentiation, fusing with the host fibers or generating new myofibers to reconstruct damaged tissue (Charge and Rudnicki, 2004). In several diseases and conditions affecting muscle, a reduction in muscle mass is seen that is associated with reduced numbers of satellite cells and a reduced ability of the satellite cells to repair, regenerate and grow skeletal muscle. A few exemplary diseases and conditions affecting muscle include wasting diseases, such as cachexia, muscular attenuation or atrophy, including sarcopenia, ICU-induced weakness, surgery-induced weakness (e.g. following knee or hip replacement), and muscle degenerative diseases, such as muscular dystrophies. The process of muscle regeneration involves considerable remodeling of extracellular matrix and, where extensive damage occurs, is incomplete. Fibroblasts within the muscle deposit scar tissue, which can impair muscle function, and is a significant part of the pathology of muscular dystrophies.

Muscular dystrophies are genetic diseases characterized by progressive weakness and degeneration of the skeletal or voluntary muscles which control movement. The muscles of the heart and some other involuntary muscles are also affected in some forms of muscular dystrophy. In many cases, the histological picture shows variation in fiber size, muscle cell necrosis and regeneration, and often proliferation of connective and adipose tissue. The progressive muscular dystrophies include at least Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

Currently there is no cure for these diseases, but certain medications and therapies have been shown to be effective. For instance, corticosteroids have been shown to slow muscle destruction in Duchene muscular dystrophy patients. While corticosteroids can be effective in delaying progression of the disease in many patients, long-term corticosteroid use is undesirable due to unwanted side effects.

Researchers are also investigating the potential of certain muscle-building medicines. One such approach is to block the protein myostatin, a growth factor known to play a role in the growth and development of muscle. For instance, monoclonal antibodies specific to myostatin have been shown to improve the condition of mice with muscular dystrophy, presumably by blocking the action of myostatin. The myostatin-blocking approach presents concerns however. For instance, blocking myostatin could interfere with the satellite cells that help replace injured or dead muscle cells. It is believed that myostatin helps keep satellite cells at rest until they are needed and, without myostatin, the satellite cells could become depleted. In addition, it has been proposed that myostatin blockers may be too targeted to boost muscle growth, as there are a variety of proteins similar to myostatin that also limit muscle growth PCT Application No. WO 2007/059612 (Rudnicki et al.) describes a novel population of Pax7+/Myf5− satellite stem cells. This group was the first to confirm that satellite stem cells are a heterogeneous population containing stem cells (Pax7+/Myf5−) and progenitor cells (Pax7+/Myf5+). Prior to this disclosure, it was unclear whether satellite cells were stem cells, committed progenitors or de-differentiated myoblasts, and whether the niche was homogenous or heterogeneous. Using Cre/LoxP lineage-tracing, the group identified a sub-population of satellite cells which had never expressed Myf5 and functioned as a stem cell reservoir (see also Kuang et al., 2007). The group successfully isolated the Pax7+/Myf5− satellite stem cells, which were found to represent about 10% of the adult satellite cell pool and give rise to daughter satellite myogenic cells (Pax7$^+$/Myf5$^+$) through asymmetric apical-basal cell divisions. Transplantation of both Myf5$^-$ and Myf5$^+$ FACS-sorted satellite cells demonstrated that satellite stem cells are capable of repopulating the adult satellite cell niche as well as self-renewal (Kuang et al., 2007). It has recently been demonstrated that, during skeletal muscle regeneration, the satellite cell population is maintained by the stem cell subpopulation, thus allowing tissue homeostasis and multiple rounds of regeneration during the lifespan of an individual (Kuang et al., 2007). Knowledge of the molecular networks regulating satellite stem cell fate decisions has remained unclear.

PCT Application No. WO 2004/113513 (Rudnicki et al.) discloses methods and compositions for modulating proliferation or lineage commitment of an atypical population of CD45$^+$Sca1$^+$ stem cells, located outside the satellite stem cell compartment, by modulating myogenic determination of Wnt proteins.

The Wnt family of genes encode over twenty cysteine-rich, secreted Wnt glycoproteins that act by binding to Frizzled (Fzd) receptors on target cells. Frizzled receptors are a family of G-protein coupled receptor proteins. Binding of different members of the Wnt-family to certain members of the Fzd family can initiate signaling by one of several distinct pathways. In the termed canonical pathway, activation of the signaling molecule, Disheveled, leads to the inactivation of glycogen synthase kinase-3 (GSK-3β), a cytoplasmic serine-threonine kinase. The GSK-3β target, β-catenin, is thereby stabilized and translocates to the nucleus where it activates TCF (T-cell-factor)-dependant transcription of specific promoters (Wodarz, 1998, Dierick, 1999). In the non-canonical, or planar cell polarity (PCP) pathway, binding of Wnt to Fzd also activates Disheveled, which in this case activates RhoA, a small g protein. Activation of the PCP pathway does not result in nuclear translocation of β-catenin.

Wnt signaling plays a key role in regulating developmental programs through embryonic development, and in regulating stem cell function in adult tissues (Clevers, 2006). Wnts have been demonstrated to be necessary for embryonic myogenic induction in the paraxial mesoderm (Borello et al., 2006; Chen et al., 2005; Tajbakhsh et al., 1998), as well in the control of differentiation during muscle fiber development (Anakwe et al., 2003). Recently, the Wnt planar cell polarity (PCP) pathway has been implicated in regulating elongation of differentiating myocytes in the developing myotome (Gros et al., 2009). In the adult, Wnt signaling is necessary for the myogenic commitment of adult CD45+/Sca1+ stem cells in muscle tissue following acute damage (Polesskaya et al., 2003; Torrente et al., 2004). Other studies suggest that canonical Wnt/β-catenin signaling regulates myogenic differentiation through activation and recruitment of reserve myoblasts. In addition, Wnt/β-catenin signaling in satellite cells within adult muscle appears to control myogenic lineage progression by limiting Notch signaling and thus promoting differentiation. Thus, traditionally, it has been assumed that Wnt proteins act as stem cell growth factors, promoting the proliferation and differentiation of stem cells and/or progenitor cells.

Stem cells, and therapies targeting stem cells, have the potential for providing benefit in a variety of clinical settings. A limitation to many potential therapeutic applications has been obtaining a sufficient number of undifferentiated stem cells, and stimulating terminal differentiation into mature tissue-specific cells without depleting the stem cell reservoir. Much current stem cell research focuses on directing the proliferation and differentiation of stem cells, in particular, transient amplifying progenitors, to repair or regenerate damaged tissue. In addition to concerns about stem cell depletion, another concern with stimulating proliferation and differentiation of stem cells is abnormal or poorly-formed tissue. Accordingly, there is a need in the art for continued research and development in the area of stem cells and for new and improved methods and compositions for modulating stem cell function in a physiological manner.

SUMMARY OF THE INVENTION

Generally, the present invention provides compositions and methods for modulating stem cells and uses thereof. More particularly, the present invention provides compositions and methods for modulating stem cell division symmetry.

Various non-limiting aspects and embodiments of the invention are described below.

In one aspect, there is provided a composition for modulating the division symmetry of a stem cell comprising as an active agent a modulator of planar cell polarity (PCP) signaling in the stem cell.

In another aspect, there is provided a method for modulating division symmetry of stem cells comprising contacting the stem cells with a composition comprising as an active agent a modulator of planar cell polarity (PCP) signaling in the stem cell.

In some embodiments, the active agent is an activator of PCP signaling capable of promoting symmetrical division of the stem cell. The active agent may, for example, comprise or be derived from a small molecule, a polynucleotide, a peptide, a polypeptide, or a combination thereof.

In some embodiments, the active agent comprises one or more of the following:

(a) a peptide or polypeptide capable of binding to and/or activating Fzd7;

(b) a polynucleotide encoding a peptide or polypeptide capable of binding to and/or activating Fzd7;

(c) a small molecule capable of binding to and/or activating Fzd7;

(d) a polynucleotide or polypeptide capable of upregulating expression of Fzd7 on the stem cell; or (e) an polynucleotide or polypeptide capable of activating or inducing expression of an effector molecule in the PCP pathway to thereby promote symmetrical division.

In certain embodiments, the active agent comprises (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In certain selected embodiments, the active agent comprises a Wnt7a polypeptide.

In other embodiments, the active agent comprises a polynucleotide encoding a Wnt7a polypeptide. The polynucleotide may, for example, be present in an expression vector.

In still other embodiments, the active agent modulates one or more effector molecules in the PCP pathway, e.g. Vangl2, α7-integrin, Prickle 1 or Celsr2.

In one embodiment, the active agent is capable of inducing expression or polarized distribution of Vangl2 in the cell membrane.

In some embodiments, the composition may comprise stem cells.

In some embodiments, the composition may comprise an inhibitor of canonical Wnt/β-catenin signaling in the stem cell.

In some embodiments, the composition may comprise one or more stem cell modulators, such as, a modulator that increases the rate of stem cell division or stem cell survival.

In some embodiments, the stem cell is an adult stem cell. In certain embodiments, the adult stem cell is a satellite stem cell.

In some embodiments, the compositions and methods of the invention are used for promoting tissue formation, regeneration, maintenance or repair. In some embodiments, the tissue is muscle. In some embodiments, the muscle is skeletal muscle.

In one aspect, there is provided a composition for enhancing tissue formation, regeneration, maintenance or repair in a mammal comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In one aspect, there is provided a method for enhancing tissue formation, regeneration, maintenance or repair in a mammal comprising administering to a subject in need thereof a composition comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In some embodiments, the composition may be admixed with a physiologically acceptable vehicle, carrier or diluent. In some embodiments, the composition is formulated for injection. For instance, the composition may be formulated for one or more of intravenous injection, intramuscular injection, intracardiac injection, subcutaneous injection, or intraperitoneal injection.

In some aspects, the compositions and methods described herein are useful for promoting formation, maintenance, repair or regeneration of skeletal muscle in a human subject in need thereof. For instance, the subject in need thereof may suffer from a disease or condition affecting muscle.

In some embodiments, the subject may have, or be suspected of having, a degenerative disease. In some embodiments, the degenerative disease is a muscular dystrophy, examples of which include, Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

In some embodiments, the muscular dystrophy is Duchenne muscular dystrophy (DMD).

In some embodiments, the subject suffers from muscle wasting or atrophy associated with injury or illness.

In some embodiments, the disease or condition affecting muscle may include a wasting disease (e.g. cachexia, which may be associated with an illness such as cancer or AIDS), muscular attenuation or atrophy (e.g. sarcopenia, which may be associated with aging), ICU-induced weakness, prolonged disuse (e.g. coma, paralysis), surgery-induced weakness (e.g. following hip or knee replacement), or a muscle degenerative disease (e.g. muscular dystrophies). This list is not exhaustive.

In another aspect, there is provided a method for modulating division symmetry of stem cells in vivo or in vitro comprising contacting the stem cells with a composition comprising an effective amount of an active agent selected from an activator or an inhibitor of planar cell polarity (PCP) signaling in the stem cell.

In some embodiments, the method may comprise contacting stem cells with an inhibitor of canonical Wnt/β-catenin signaling in the stem cell. Such inhibition may further promote symmetrical stem cell division.

In some embodiments, the method may comprise contacting the stem cell with one or more stem cell modulators, for example a modulator that increases the rate of stem cell division or increases cell survival.

In some embodiments, the method is an in vivo method and wherein the composition is administered to a subject in need thereof.

In some embodiments, the method may comprise administering stem cells to the subject. The stem cells, for example, be administered simultaneously or sequentially with the composition.

In some embodiments, the composition comprises stem cells. In some embodiments, the stem cells may comprise an expression vector comprising a polynucleotide encoding Fzd7 or a modulator of PCP signaling capable of promoting symmetrical division.

In some embodiments, the method may comprise administering helper cells to a subject. The helper cells may, for example, be administered simultaneously or sequentially with the composition. In some embodiments, the composition may comprise helper cells. The helper cells may, for example, comprise an expression vector comprising a polynucleotide encoding a Wnt7a protein or an active fragment, variant, analogue or derivative thereof capable of being secreted from the helper cell and binding to and/or activating Fzd7.

In one aspect, there is provided a method for promoting muscle formation, regeneration, maintenance or repair in a mammal comprising administering to the mammal a therapeutically effective amount of a composition as herein.

In one aspect, there is provided a method for promoting muscle formation, regeneration or repair in a subject in need thereof comprising administering to the subject a composition comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In some embodiments, a cell or tissue is transformed to overexpress Wnt7a to thereby induce symmetrical stem cell division. Gene expression may optionally be under the control of an inducible promoter.

In another aspect, there is provided a method for preventing muscle wasting, atrophy or degeneration in a subject in need thereof comprising administering to the subject a therapeutically effective amount of a composition comprising (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In another aspect, there is provided a method for expanding a population of satellite stem cells in vivo or in vitro comprising contacting the stem cells with an effective amount of a composition comprising (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In some embodiments, stem cells, e.g. satellite stem cells, are expanded in vitro. In some embodiments, the in vitro expanded stem cells are subsequently administered to a subject in need thereof.

In another aspect, there is provided a method of promoting satellite stem cell expansion comprising contacting the stem cell with Wnt7a or an active fragment, variant, analogue or derivative thereof capable of activating Fzd7.

In another aspect, there is provided a use of a composition described herein for promoting formation, maintenance, repair, or regeneration of muscle in a subject in need thereof.

In another aspect, there is provided a use of a composition as described herein for the manufacture of a medicament for promoting formation, maintenance, repair, or regeneration of muscle in a subject in need thereof.

In another aspect, there is provided a use of Fxz7 as a marker of quiescent satellite cells, wherein the marker is used in combination with another stem cell marker.

In another aspect, there is provided a method of identifying or isolating a satellite stem cell comprising, selecting for the marker Pax7+ in combination with YFP− or Myf−.

In another aspect, there is provided a composition wherein the active agent is an inhibitor of PCP signaling capable of inhibiting symmetrical division of the stem cell. The inhibitor may, for example, be a peptide, polypeptide, polynucleotide or small molecule capable of directly or indirectly inhibiting PCP signaling via inhibition of Wnt7a, Fzd7, or an effector molecule in the PCP pathway, e.g., Vangl2, α7-integrin, Prickle 1 or Celsr2.

In some embodiments, the inhibitor is a polynucleotide capable of inhibiting expression of Wnt7a, Fzd7, or an effector molecule in the PCP pathway, e.g. siRNA or miRNA. In one embodiment, the inhibitor is Vangl2 siRNA.

In another aspect, there is provided a method of screening for a compound useful in the repair or regeneration of muscle comprising:
(a) providing a population of satellite stem cells;
(b) treating the stem cells with a test compound; and
(c) determining the proportion of symmetrical to asymmetrical divisions of the treated stem cells compared to control, wherein a increase in the proportion of symmetrical divisions compared to control indicates that the compound is useful in the repair or regeneration of muscle.

In another aspect, there is provided a method of screening for a compound useful in the repair or regeneration of muscle comprising:
(a) providing a population of satellite stem cells;
(b) treating the stem cells with a test compound; and
(c) determining whether the compound activates stimulates PCP signaling in the treated stems, wherein a increase in PCP signaling indicates that the compound is useful in the repair or regeneration of muscle.

In some embodiments, the stimulation of PCP signaling occurs via activation of Fzd7.

In some embodiments, the increase is an increase of at least about 10%, 25%, 50%, 75% or greater.

In an aspect of the invention, there is provided a composition for promoting symmetrical stem cell division comprising as active agent one or more activators of the Fzd7 receptor, wherein the one or more activators may include, but are not limited to, one or more small molecules, nucleic acids, polypeptides, peptides, macromolecules or a combination thereof, that activate Fzd7 receptor in adult stem cells. In some embodiments, the adult stem cells are satellite stem cells.

In some embodiments, a stem cell may be transformed to overexpress Fzd7.

In another aspect there is provided, a method for preventing satellite stem cell depletion comprising contacting the stem cell with (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

Embodiments of the present invention will now be described, by way of example only, with reference to the attached Figures, wherein.

Wnt3a expression plasmids, as compared to contralateral leg, 3 weeks after electroporation (n=4, *p≤1.03). Errors bars represent SEM.

Figure 10:
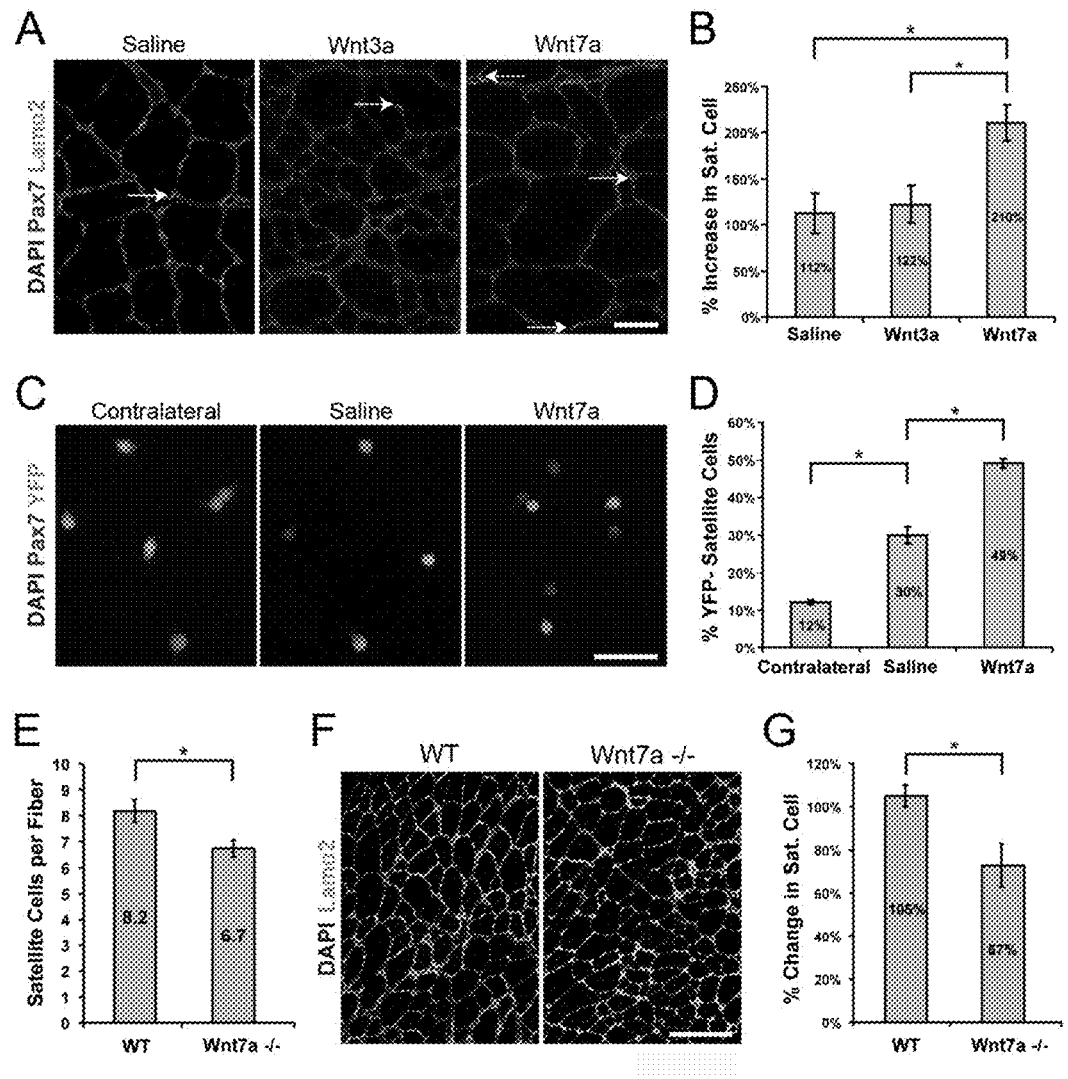

FIG. 10. Wnt7a Drives Satellite Stem Cell Expansion. (A) TA muscles of 3-month old mice were electroporated with either saline or a Wnt7a/Wnt3a expression plasmid, and dissected after 3 weeks. Sublaminar Pax7$^+$ satellite cells were scored on cryosections of electroporated muscles. Note the increased numbers of Pax7$^+$ satellite cells following electroporation with CMV-Wnt7a plasmid. Bar is 25 μm. (B) The satellite cell population was increased by two-fold following electroporation of CMV-Wnt7a plasmid (n=4, *p≤1.03), as compared to Saline– or Wnt3a– electroporated samples. (C) Satellite cells were FACS-sorted from electroporated Myf5-Cre/ROSA26-YFP TA muscles, 3 weeks after electroporation, and plated in culture for 24 hours, fixed and stained for Pax7 and YFP. Bar is 10 μm. (D) The proportion of Pax7$^+$/YFP$^-$ satellite stem cells was significantly increased following over-expression of Wnt7a in electroporated TA muscles (n=5, *p≤0.0001). (E) Wnt7a$^{-/-}$ myofibers showed a reduced population of Pax7+ satellite cells on myofibers were isolated from EDL muscle. (n=4, *p=0.03). (F) Cryosections of freeze-injured TA muscles of 3-month old Wnt7a$^{-/-}$ null mice and their littermate controls analyzed at 3 weeks following injury. No significant difference in terms of structure or cross-sectional area was observed in the regenerated muscle. Bar is 20 μm. (n=3). (G) Decreased numbers of satellite cells were observed in regenerated Wnt7a$^{-/-}$ TA muscles normalized to the number of myofibers in cross-sectional area and to the contralateral leg. (n=3, *p=0.03). Errors bars represent SEM.

Figure 11:
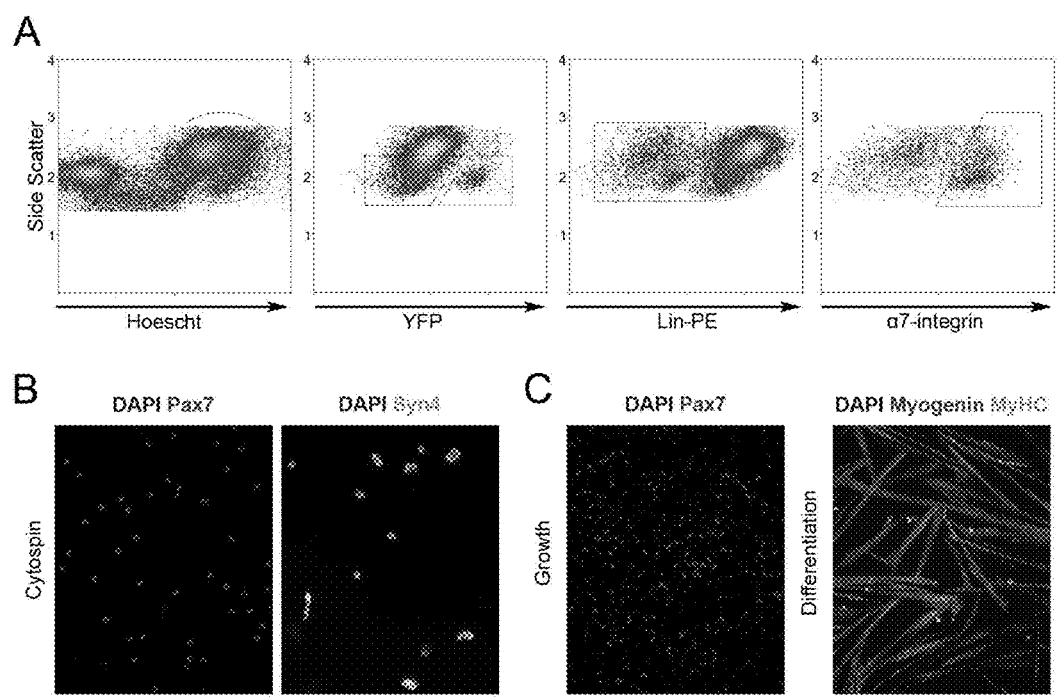

FIG. 11. FACS purification of muscle satellite cells. (A) FACS profiles for selection of live satellite cells from fore- and hindlimb skeletal muscles. Cells were positively selected for CD34 (APC-Cy7) and α7-Integrin (APC) and negatively selected for CD11 b CD31, CD45 and Sca1 (all in PE). Myf5$^+$ and Myf5$^-$ satellite cells were then separated on the basis of YFP fluorescence. (B) Cytospin of freshly isolated {CD34$^+$, α7-Integrin$^+$, Lin$^-$} satellite cells. Sorted cells express the satellite cell markers Pax7 (left) and Syndecan4 (right). (C) In vitro development of sorted {CD34$^+$, α7-Integrin$^+$, Lin$^-$} satellite cells. After one week in culture, 98% of sorted cells express Pax7 (unequal levels of Pax7 staining account for differences in individual myoblasts cell cycle). After 4 days in differentiation medium, sorted cells form multinucleated myotubes expressing Myogenin and myosin heavy chains.

Figure 12:
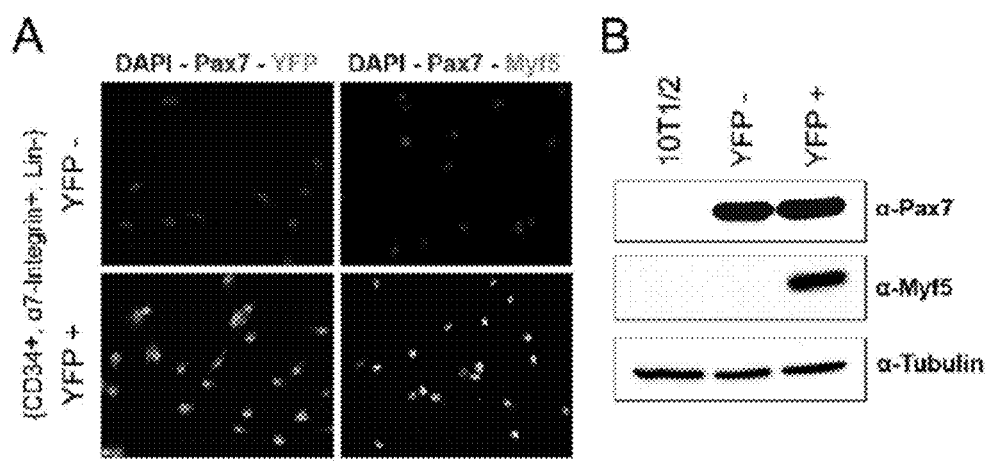

FIG. 12. YFP$^-$ satellite cell-derived myoblasts do not express Myf5 protein. FACS-sorted YFP$^+$ and YFP$^-$ satellite cells were cultured in high mitogenic medium for 2 weeks. Cells were maintained at less than 10% confluence to avoid myogenic commitment of YFP$^-$ cells. Cycling YFP$^+$ myoblasts express high levels of Myf5 protein while YFP$^-$ myoblasts do not exhibit any detectable Myf5 protein expression, as revealed by immunostaining (A) and western (B) analysis. 10T1/2 cells were used as a negative non-myogenic control (n=3).

Figure 13:
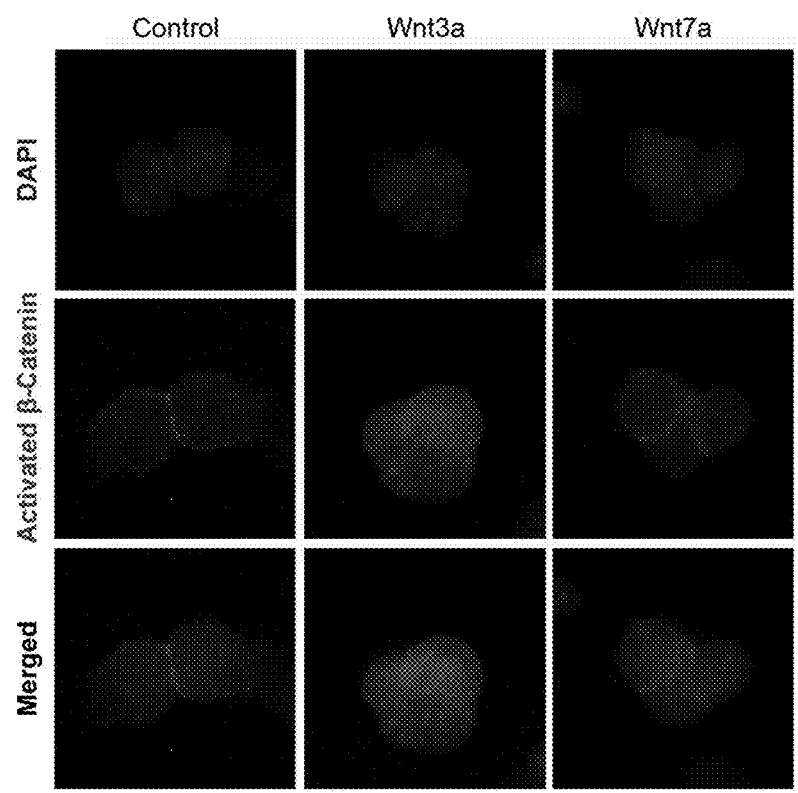

FIG. 13. Wnt7a does not induce stabilization and nuclear localization of β-Catenin in activated muscle satellite cells. Single EDL myofibers were cultured in suspension for 2 days, in control medium or with medium supplemented with Wnt3a or Wnt7a. Myofibers were stained with an antibody recognizing the active form of fl-Catenin. Wnt3a treatment causes fl-Catenin stabilization and translocation into satellite cells' nucleus. Wnt7a do not activate Wnt canonical signaling in dividing satellite cells.

Figure 14:
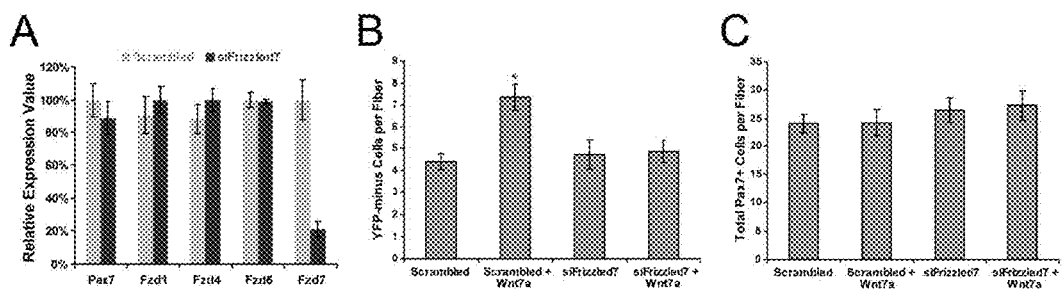

FIG. 14. Wnt7a increase satellite stem cell self-renewal while not modifying satellite cell proliferation kinetics. (A) Real-time PCR analysis of Frizzled transcripts in cultured myogenic cells in control (non-silencing) and Fzd7-silencing conditions. Fzd7 transcription was reduced by 80% (n=3, p=0.01, n=3). Knock-down of Fzd7 is specific and does not effect the expression of other Frizzled transcripts expressed in myogenic cells. (B) EDL single myofibers from Myf5-Cre/ROSA26-YFP mice were cultured in floating conditions for 52 hours. The Wnt7a-induced increase in satellite stem cell number was abrogated following silencing of Fzd7 on myofibers (n=3, *p<0.03). (C) Wnt7a treatment did not have an impact on the total number of Pax7+ cells per myofibers (n=3). Errors bars represent SEM.

Figure 15:
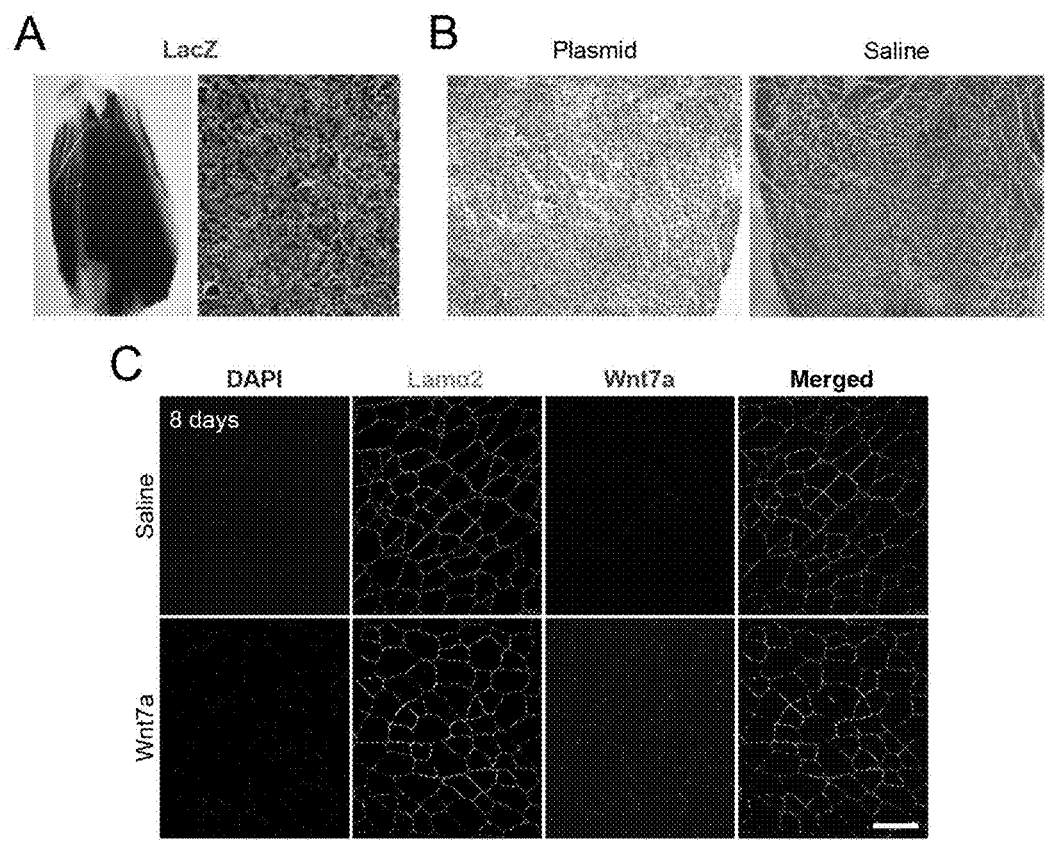

FIG. 15. Efficient electroporation of plasmids in the adult TA muscle. (A) The vast majority of the TA myofibers were transfected with a CMV-LacZ expression plasmid. X-Gal staining revealing β-galactosidase activity in whole-mount view (left), and histology on cryosections (right). (B) Representative histology of transfected muscle 1 week after electroporation. Electroporation with a control plasmid (left) did not yield any significant differences in the regeneration process, as compared to a saline electroporation (right). (C) Ectopic expression of Wnt7a by majority of the fibers 8 days after electroporation of TA muscle with a CMV-Wnt7a expression plasmid. Immunohistochemistry of cryosections stained with specific antibodies reactive with α2-laminin and Wnt7a.

Figure 16:
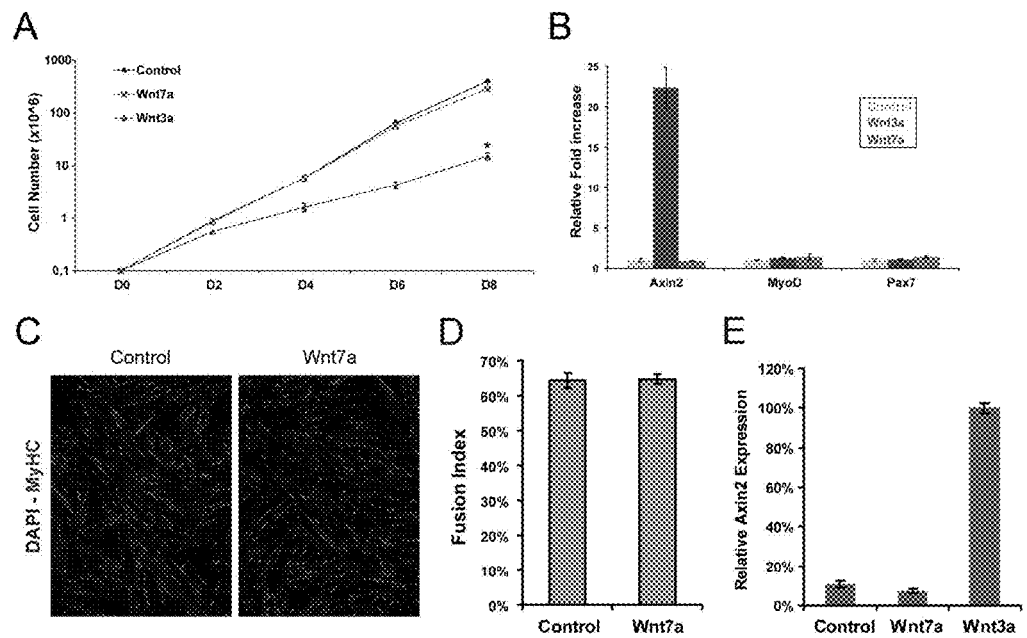

FIG. 16. Wnt7a does not have an effect on myogenic proliferation or differentiation. (A) Satellite cell-derived myoblasts were grown in vitro in control or Wnt supplemented growth media. Wnt7a treatment did not alter the kinetics of committed myogenic progenitors. Wnt3a treatment resulted in a reduced cell proliferation (n=3, p=0.01). (B) Satellite cell-derived myoblasts cultured in differentiation media for 24 hours were treated for 24 hours with either Wnt3a or Wnt7a recombinant proteins. Wnt treatment did not activate MyoD or Pax7 transcription (n=5). Wnt3a treatment activated Axin2 transcription. (C) Satellite cell-derived myoblasts were grown to 60% confluence and shifted to control differentiation media or in differentiation medium supplemented with Wnt7a for 4 days. Differentiated cells were immunostained for myosin heavy chains. No differences in morphology or size of the differentiated myotubes were observed between control and Wnt7a-treated cultures. (D) Fusion index quantification did not show any significant differences between control and Wnt7a-treated cultures (n=3). (E) Myoblasts cultured in differentiation media for 24 hours were treated for 6 hours with either Wnt3a or Wnt7a recombinant proteins. Wnt3a, but not Wnt7a, activated the transcription of Wnt-β-Catenin target genes such as Axin2 (10-fold increase, n=3). Errors bars represent SEM.

Figure 17:
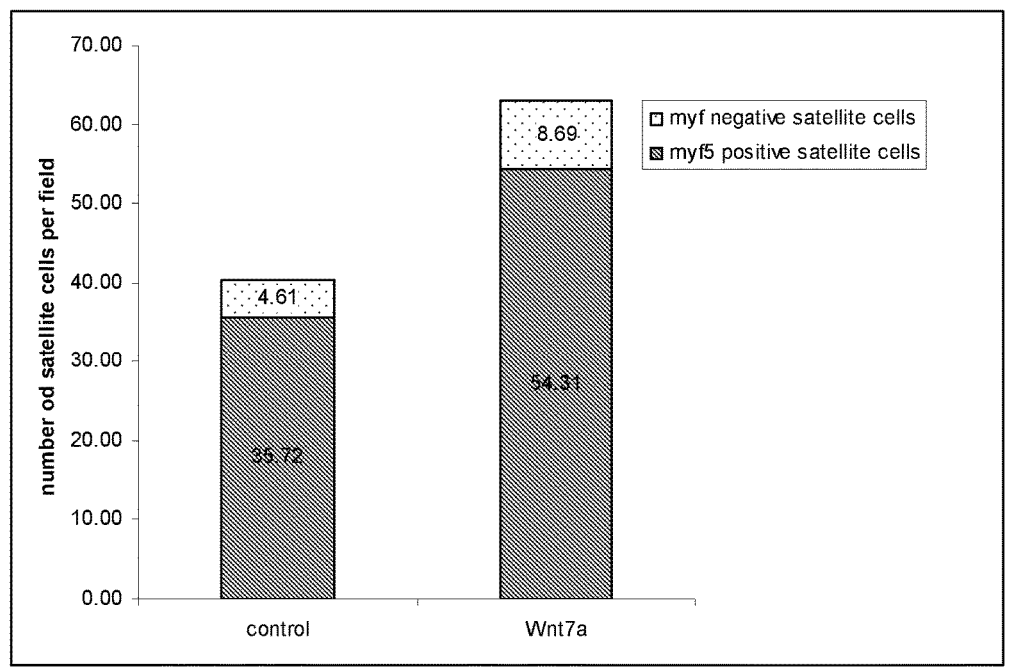

FIG. 17. Electroporation of Wnt7a cDNA into the TA muscle of adult wt mice leads to an increase in satellite cell numbers. Electroporation of Wnt7a cDNA into the TA muscle resulted in an increase in the number of satellite cells as well as in the number of satellite stem cells (myf5 negative, Pax7 positive).

Figure 18:
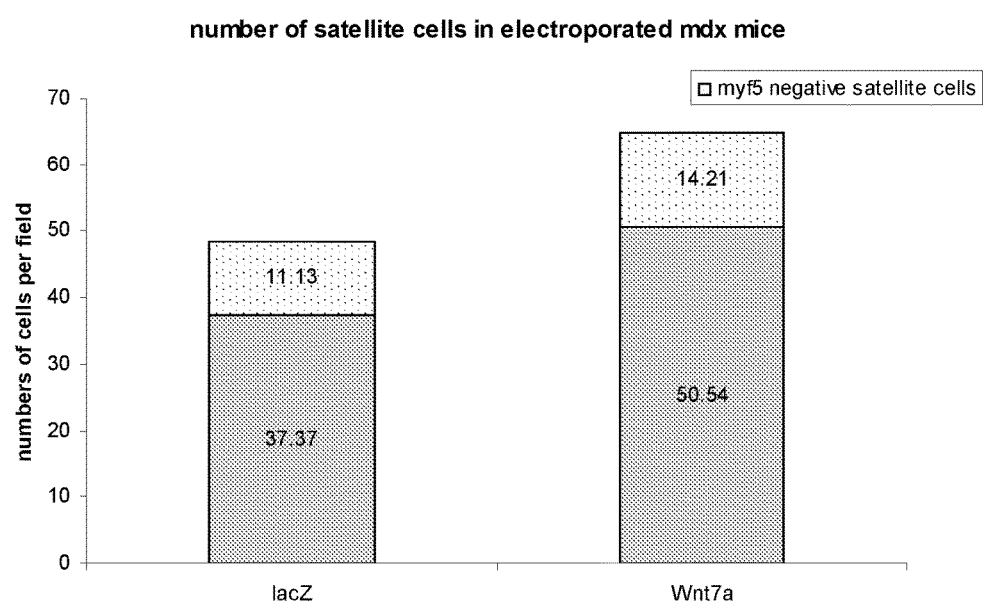

FIG. 18. Number of satellite cells in mdx mice after electroporation with a Wnt7a-containing plasmid. The TA muscle of mdx mice was electroporated after injection of a control (lacZ) plasmid or a plasmid containing the coding region of Wnt7a under control of the CMV promoter. The total number of satellite cells (all Pax7 positive cells) as well as satellite stem cells (myf5 negative satellite cells) was counted. The total number of satellite cells was significantly increased in mdx mice electroporated with a Wnt7a containing plasmid (p=0.005).

Figure 19:
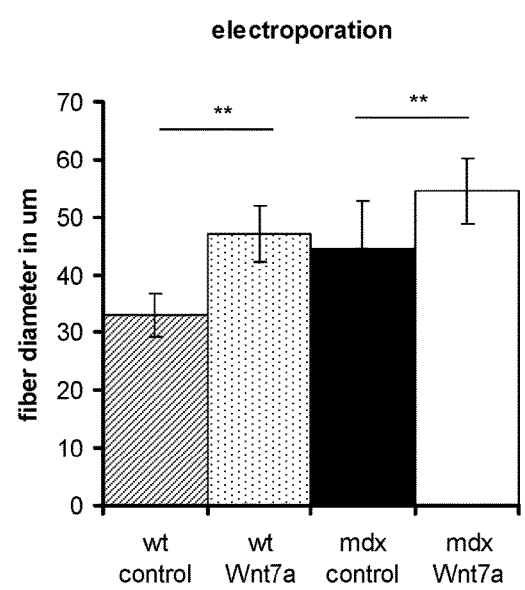

FIG. 19. Electroporation of Wnt7a containing plasmid increases fiber diameters in mdx and wt mice. Mdx mice as well as age-matched wt mice (3 month old, male) were electroporated with either the Wnt7a containing plasmid or the lacZ control plasmid. Electroporation of Wnt7a cDNA lead to a significant increase in muscle fiber diameter in mdx and wt mice (p<0.001).

FIGS. 20A-B. Administration of Wnt7a recombinant protein produces effects similar to electroporation with a Wnt7a plasmid. A. Human Wnt7a protein was injected into the TA muscle and was found to enhance muscle fibre size significantly two weeks after injection (p<0.001). B. The observed effects were similar to those produced by electroporation of CMV-driven mouse Wnt7a plasmid.

FIG. 21. *Mus musculus* Wnt7a cDNA sequence. *Mus musculus* Wnt7a cDNA sequence with coding region underlined (SEQ ID NO: 1).

FIG. 22. *Mus musculus* Wnt7a amino acid sequence. *Mus musculus* Wnt7a amino acid sequence with putative mature peptide underlined (SEQ ID NO: 2).

FIG. 23. *Homo sapiens* Wnt7a cDNA sequence. *Homo sapiens* Wnt7a cDNA sequence with coding region underlined (SEQ ID NO: 3).

FIG. 24. *Homo sapiens* Wnt7a amino acid sequence. *Homo sapiens* Wnt7a amino acid sequence with mature peptide underlined (SEQ ID NO: 4).

FIG. 25. *Mus musculus* Fzd7 cDNA sequence. *Mus musculus* Fzd7 cDNA sequence with coding region underlined (SEQ ID NO: 5).

FIG. 26. *Mus musculus* Fzd7 amino acid sequence. *Mus musculus* Fzd7 amino acid sequence with putative cysteine-rich Wnt-binding domain underlined, residues defining putative Wnt-binding site bolded, and putative PDZ-domain-binding motif double underlined (SEQ ID NO: 6)

FIG. 27. *Homo sapiens* Fzd7 cDNA sequence. *Homo sapiens* Fzd7 cDNA sequence with coding region underlined (SEQ ID NO: 7).

FIG. 28. *Homo sapiens* Fzd7 amino acid sequence. *Homo sapiens* Fzd7 amino acid sequence, with putative cysteine-rich Wnt-binding domain underlined, residues defining putative Wnt-binding site bolded, and putative PDZ-domain-binding motif double-underlined (SEQ ID NO: 8).

FIG. 29. *Mus musculus* Vangl2 cDNA sequence. *Mus musculus* Vangl2 cDNA sequence with coding region underlined (SEQ ID NO: 9).

FIG. 30. *Mus musculus* Vangl2 amino acid sequence. *Mus musculus* Vangl2 amino acid sequence with putative phosphorylation sites underlined and putative PDZ-domain-binding motif bolded (SEQ ID NO: 10).

FIG. 31. *Homo sapiens* Vangl2 cDNA sequence. *Homo sapiens* Vangl2 cDNA sequence with coding region underlined (SEQ ID NO: 11).

FIG. 32. *Homo sapiens* Vangl2 amino acid sequence. *Homo sapiens* Vangl2 amino acid sequence with putative phosphorylation sites underlined and putative PDZ-domain-binding motif bolded (SEQ ID NO: 12).

DETAILED DESCRIPTION

Generally, the present invention provides compositions and methods for modulating stem cells, in particular, adult stem cells. More particularly, the present invention provides compositions and methods for modulating stem cell division decisions.

Various uses of the compositions and methods described herein are also provided, including therapeutic uses, for example, for promoting tissue formation, regeneration, repair or maintenance.

The following description details various aspects and embodiments of the invention as contemplated by the inventors. It is understood that the scope of the invention is not limited to the exemplary embodiments described herein.

It has now been demonstrated that activation of the planar cell polarity (PCP) pathway in stem cells, e.g. adult stem cells, promotes symmetrical stem cell division. Symmetrical division gives rise to two daughter cells and results in expansion of the stem cell pool. Conversely, inhibition of PCP signaling in stem cells inhibits symmetrical division, resulting in an increase in asymmetrical (apical-basal) cell division, which does not expand the stem cell pool. Interestingly, promotion of symmetrical stem cell division via activation the PCP pathway had no effect on the rate of cell division.

It has now been demonstrated that Wnt7a, acting via the Frizzled7 (Fzd7) receptor, activates of PCP signaling in adult stem cells, e.g. satellite stem cells. Satellite stem cells are adult stem cells that give rise to muscle cells. It has further been demonstrated that inhibition of receptor or effector molecules in the PCP pathway, e.g. Fzd7 or Vangl2, abrogated the effects of Wnt7a. It has further been demonstrated administration of Wnt7a polypeptide, or a polynucleotide encoding a Wnt7a polypeptide, significantly increased satellite stem cell numbers in vitro and in vivo, and promoted tissue formation in vivo, leading to enhanced repair and regeneration in injured and diseased muscle tissue.

Thus, Wnt7a, Fzd7 and other components of the PCP signaling pathway are novel targets for modulation of stem cell division decisions, and promotion of tissue formation, regeneration, maintenance and repair.

Definitions

Unless defined otherwise, all technical and scientific terms used herein have the same meaning as commonly understood by one of ordinary skill in the art to which this invention pertains.

The term "stem cell", as used herein, refers to an undifferentiated cell that is capable of differentiating into a number of final, differentiated cell types. Different stem cells may have different potency. While the definitions below reflect current understanding, our knowledge and understanding of stem cells is constantly evolving. Totipotent stem cells typically have the capacity to develop into any cell type and are usually embryonic in origin. Pluripotent stem cells are typically cells in a stem cell line capable of differentiating into several differentiated cell types. Multipotent stem cells can differentiate into a number of cells, but only those of a closely related family. Unipotent stem cells can produce only one cell type, their own, but have the property of self-renewal which distinguishes them from non-stem cells. A muscle stem cell is an example of stem cell that is traditionally thought to be unipotent, giving rise to muscle cells only.

An "adult stem cell" is a stem cell found in a developed organism. Adult stem cells include, but are not limited to, hematopoietic stem cells, mesenchymal stem cells, neural stem cells, endothelial stem cells and muscle stem cells.

A "satellite stem cell" is an example of an adult stem cell that gives rise to muscle cells.

The term "progenitor cell", as used herein, refers to a cell that is committed to a particular cell lineage and which gives rise to cells of this lineage by a limited series of cell divisions. A myoblast is an example of a progenitor cell, which is capable of differentiation to only one type of cell, but is itself not fully mature or fully differentiated.

The term "symmetrical division", as used herein in reference to stem cells, refers to a cell division that increases the number of cells of the same type. The term "planar division" may also be used. Symmetrical stem cell division gives rise to two daughter stem cells, thereby expanding the stem cell pool. The term "expansion" therefore refers to an increase in the number of a cells of a particular type as a result of symmetrical division.

The term "asymmetrical division", as used herein in reference to stem cells, refers to a cell division that gives rise to one daughter stem cell and one progenitor cell, with no increase in stem cell number. The term "apical-basal division" may also be used.

By "promoting", "enhancing" or "increasing" symmetrical stem cell division, it is meant that the ratio of symmetrical to asymmetrical cell division is increased compared to normal or control, e.g. the ratio in the absence of a particular active agent, composition or treatment method. For example, the ratio of symmetrical to asymmetrical cell division may be increased by at least 10%, 20%, 30%, 40%, 50%, 60%, 70%, 80%, 90%, 100%, 125%, 150%, 175%, 200%, or even greater.

The term "differentiation", as used herein, refers to a developmental process whereby cells become specialized for a particular function, for example, where cells acquire one or more morphological characteristics and/or functions different from that of the initial cell type. The term "differentiation" includes both lineage commitment and terminal differentiation processes. States of undifferentiation or differentiation may be assessed, for example, by assessing or monitoring the presence or absence of biomarkers using immunohistochemistry or other procedures known to a person skilled in the art.

The term "lineage commitment", as used herein, refers to the process in which a stem cell becomes committed to forming a particular limited range of differentiated cell types. Lineage commitment arises, for example, when a stem cell gives rise to a progenitor cell during apical-basal division. Committed progenitor cells are often capable of self-renewal or cell division.

The term "terminal differentiation", as used herein, refers to the final differentiation of a cell into a mature, fully differentiated cell. Usually, terminal differentiation is associated with withdrawal from the cell cycle and cessation of proliferation.

The term "Wnt" refers to a family of related genes and proteins. The Wnt genes encode over twenty cysteine-rich, secreted, Wnt proteins (glycoproteins) that act by binding to Frizzled (Fzd) receptors on target cells. A number of Wnt polypeptides are known in the art, including the human Wnts: Wnt 1, Wnt 2, Wnt 3, Wnt 4, Wnt 5a, Wnt 5b, Wnt 7a and Wnt 7b, and the mouse Wnts: Wnt 1, Wnt 2, Wnt 3a, Wnt 3b, Wnt 4, Wnt 5a, Wnt 5b, Wnt 6, Wnt 7a, Wnt 7b, Wnt 8a, Wnt 8b, Wnt Iea, Wnt I0b, Wnt 11 and Wnt 12. Homologues from other species are also known and accessible to a person skilled in the art. Members of the Wnt family demonstrate marked evolutionary conversation and thus a high degree of homology is observed between species.

"Frizzled" (Fzd) receptors are a family of G-protein coupled receptor proteins to which Wnt molecules are known to bind. Sequences of various Fzd receptors are available to those skilled in the art. Fzd7 is shown herein to be expressed on satellite stem cells. Other stem cells that express Fzd7 include hESC and NSC.

Binding of different members of the Wnt family to certain members of the Fzd family on specific cells can initiate signaling by one of several distinct pathways, including canonical and non-canonical Wnt signaling pathways.

In the termed "canonical pathway", activation of the signaling molecule, Disheveled leads to the inactivation of glycogen synthase kinase-3 (GSK-3β), a cytoplasmic serine-threonine kinase. The GSK-3β target, β-catenin, is thereby stabilized and translocates to the nucleus where it activates TCF (T-cell-factor)-dependant transcription of specific promoters. This pathway is also described as the "Wnt/β-catenin" pathway herein. Canonical Wnt-signaling plays a well-documented role in regulating myogenic growth and differentiation.

In the termed "non-canonical" Wnt signaling pathway, also referred to as the "planar cell polarity" (PCP) pathway, binding of Wnt to Fzd also activates Disheveled (Dvl), which in this case activates RhoA, a small g protein, triggering a cascade that is unique from the canonical pathway. For example, in contrast to the canonical pathway, activation or stimulation of the PCP pathway does not result in nuclear translocation of β-catenin.

As used herein, "effector" molecule refers to a post-receptor signaling molecule, also referred to as a "downstream effector" molecule. Effector molecules may include, for example, cytosolic signaling molecules or nuclear signaling molecules and transcription factors, or molecules in a cell membrane, such as receptors or co-receptors. Effectors may include, for example, proteins, polynucleotides and peptides. Exemplary effector molecules in the PCP pathway include Celsr1, Celsr2, Celsr3, Dvl1, Dvl2, Dvl3, Pk1, Pk2, Pk3, Pk4, Rac/RhoA, Vangl1, Vangl2, Syndecan 4 (Syn4) and α7-β1-integrin.

In the context of a signaling pathway, "activation" may include one or more of, e.g. changes in phosphorylation, conformation, polarization, localization or distribution of a molecule within the cell or cell membrane. Activation may occur directly via activation, stimulation or upregulation of an activating component of a signaling pathway, or may occur indirectly by inhibiting an inhibitory component. The converse is also true where "inhibition" may occur directly or indirectly.

The term "modulator", as used herein, refers to both "activators" and "inhibitors" of a signaling event or pathway, for example, modulators of the Wnt7a signaling pathway. A modulator of the Wnt7a signaling pathway may be a compound or molecule that stimulates or inhibits the activity or expression of a Wnt7a polypeptide, or an upstream (activator) or downstream (effector) molecule in the Wnt7a signaling pathway, including modulators of the Frizzled7 (Fzd7) receptor. Candidate modulators of the Wnt7a signaling pathway may stimulate or inhibit the activity of a Wnt7a polypeptide directly or indirectly. Direct modulators may act on a Wnt7a polypeptide, or a gene encoding a Wnt7a polypeptide, whereas indirect modulators may act on one or more proteins, or genes encoding proteins, that act upstream ("activators") or downstream ("effectors") of a Wnt7a polypeptide in the Wnt7a signaling pathway. A modulator can act at a genetic level, for example to upregulate or downregulate the expression of a gene encoding a Wnt7a polypeptide or an activator or effector of Wnt7a signaling, or at the protein level to interfere with the activity of a Wnt7a polypeptide or an activator or effector of Wnt7a signaling. Modulators may themselves be Wnt polypeptides, or active fragments, derivatives or variants thereof. A modulator can be, for example, a polypeptide, peptide, polynucleotide, oligonucleotide, antibody or antibody fragment, or a small molecule activator or inhibitor. Small molecule modulators can be organic or inorganic.

A "stem cell modulator" is a modulator that activates or inhibits a function of a stem cell. For example, a stem cell modulator may modify stem cell division, proliferation, differentiation, or survival. For example, Wnt7a, is a modulator of stem cell division decisions.

The term "Wnt7a signaling pathway," as used herein in reference to stem cells, refers to the Wnt7a-Fzd7 signaling pathway in adult stem cells, e.g. satellite stem cells, which was shown to activate PCP signaling. Wnt7a signaling was shown to induce polarized distribution of Vangl2 and α7-integrin, two known effector molecules in the PCP pathway, thereby promoting symmetrical stem cell division. Thus, the Wnt7a signaling pathway referred to herein is the PCP signaling pathway. In certain other cell types, Wnt7a may activate other Wnt signaling pathway.

Component members of the Wnt7a signaling pathway demonstrate marked evolutionary conservation, e.g. in vertebrates and mammals. Human and mouse Wnt7A proteins share about 98% sequence identity, while corresponding Fzd7 homologues are about 96% identical and Vangl2 homologues are about 99% identical. Such high degree of homology often results in cross-species activity. For instance, it has been demonstrated herein that human Wnt7a is active in the mouse system (Example 2). Therefore, experimental findings can often be extrapolated across species.

The terms "protein", "polypeptide", and "peptide," as used herein, refer to a sequence of amino acid residues linked together by peptide bonds or modified peptide bonds. Typically, a polypeptide is at least six amino acids long and a peptide is at least 3 amino acids long. The polypeptide or peptide can be naturally occurring, recombinant, synthetic, or a combination of these. The polypeptide or peptide can be a fragment of a naturally occurring protein or polypeptide. The terms polypeptide and peptide also encompass analogues, derivatives and peptidomimetic compounds. Such compounds are well known in the art and may have significant advantages over naturally occurring peptides, including, for example, greater chemical stability, increased resistance to proteolytic degradation, enhanced pharmacological properties (such as, half-life, absorption, potency and efficacy), altered specificity (for example, a broad-spectrum of biological activities) or reduced antigenicity.

Specific proteins or polypeptides (e.g. Wnt7a, Fzd7 or Vangl2, etc.) referred to herein encompass proteins and polypeptides having amino acid sequences corresponding to naturally occurring sequences, as well as variant or homologous polypeptide sequences, fragments and derivatives having an activity at least substantially identical to a wild-type protein. Likewise, specific genes (e.g. Wnt7a, Fzd7 or Vangl2, etc.) encompass nucleic acid sequences or partial sequences encoding proteins having a polypeptide sequence corresponding to naturally occurring sequences as well as variant or homologous polypeptide sequences, fragments, analogies and derivatives having an activity at least substantially identical to a wild-type protein. Polypeptides, including variants, fragments, analogues and derivatives thereof, having an increased activity compared to wild-type polypeptides are also contemplated.

A functional "activity", as used herein in reference to a polypeptide or gene or portion thereof, refers to a polypeptide, gene or portion thereof that displays one or more activities associated with a naturally-occurring protein or gene. Functional activity in regard to a polypeptide or portion thereof may include, for example, the ability to specifically bind to and/or activate a receptor or ligand for the polypeptide.

"Naturally occurring", as used herein in reference to an object, indicates that the object can be found in nature. For example, a naturally occurring polypeptide or polynucleotide sequence would be one that is present in an organism, and can be isolated from the organism, and which has not been intentionally modified by man in the laboratory. The term "wild-type" is often used interchangeably with naturally occurring.

In the context of the present invention, a polypeptide, or fragment, variant, analogue or derivative thereof, is considered to have at least substantially the same activity as the wild-type protein when it exhibits about 50% of the activity of the wild-type protein, preferably at least 60%, 75%, or 80% of the activity of the wild-type protein. In preferred embodiments, the polypeptide, variant, fragment analogue or derivative exhibits at least about 85% of the activity of the wild-type protein, e.g. 88%, 90%, 95%, 99%, 100%. In certain embodiments, an activity greater than wild-type activity may be achieved. Activity of a Wnt7a polypeptide, variant, fragment, analogue or derivative can, for example, be determined by measuring its ability to promote symmetrical stem cell expansion and comparing to a wild-type protein. Methods of measuring and characterizing stem cell division are known in the art.

A "fragment" of a polypeptide includes, but is not limited to, an amino acid sequence wherein one or more amino acids are deleted in comparison to the wild-type sequence or another reference sequence. For example, but not to be considered limiting, a fragment exists when one or more amino acids from the amino terminal, carboxy terminal or both are removed. Further, one or more amino acids internal to the polypeptide may be deleted. Active fragments are fragments that retain functional characteristics, e.g. of the native sequence or other reference sequence. Typically, active fragments are fragments that retain substantially the same activity as the wild-type protein. A fragment may, for example, contain a functionally important domain, such as a domain that is important for receptor or ligand binding.

A "variant" polypeptide or variant fragment is one in which one or more amino acid residues have been deleted, added, or substituted for those that appear in the amino acid sequence of a wild-type sequence or another reference sequence. In the context of the present invention, a variant preferably retains substantially the same activity as the wild-type sequence or other reference sequence, or has better activity than the wild type protein.

A variant may contain one or more amino acid substitutions, which may be "conservative" or "non-conservative" substitutions. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group, while a non-conservative substitution involves the substitution of an amino acid with another amino acid from a different group.

Typically, variant amino acid sequences comprise greater than about 70%, more preferably greater than about 80%, 85%, 90%, 91%, 92%, 93%, 94%, 95%, 96%, 97%, 98% or 99% identity to the wild-type or reference sequence. The degree of identity may also be represented by a range defined by any two of the values listed above or any value therein between. Variants include "mutants", in which the reference sequence is the wild-type sequence.

A "derivative" is a peptide or polynucleotide containing additional chemical or biochemical moieties not normally a part of a naturally occurring molecule. Peptide derivatives include peptides in which one or more amino acid side chain and/or the amino-terminus and/or the carboxy-terminus has been derivatized with a suitable chemical substituent group, as well as cyclic peptides, dual peptides, multimers of the peptides, peptides fused to other proteins or carriers glycosylated peptides, phosphorylated peptides, peptides conjugated to lipophilic moieties (for example, caproyl, lauryl, stearoyl moieties) and peptides conjugated to an antibody or other biological ligand. Examples of chemical substituent groups that may be used to derivatize a peptide include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy(benzyl-CO—), monomethoxysuccinyl naphthyl-NH—CO—, acetylaminocaproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

An "analogue" is a polypeptide or peptide comprising one or more non-naturally occurring amino acids. As is known in the art, substitution of all D-amino acids for all L-amino acids within a peptide can result in an "inverse" peptide, or in a "retro-inverso" peptide (see Goodman et al. "Perspectives in Peptide Chemistry" pp. 283-294 (1981); U.S. Pat. No. 4,544,752), both of which are considered to be analogues in the context of the present invention. An "inverse" peptide is one in which all L-amino acids of a sequence have been replaced with D-amino acids, and a "retro-inverso" peptide is one in which the sequence of the amino acids has been reversed ("retro") and all L-amino acids have been replaced with D-amino acids.

"Peptidomimetics" are compounds that are structurally similar to peptides and contain chemical moieties that mimic the function of the polypeptide or peptide of the invention. For example, if a polypeptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere" refers to a chemical structure that can be substituted for a polypeptide or peptide because the steric conformation of the chemical structure is similar to that of the peptide or polypeptide, for example, the structure fits a binding site specific for the polypeptide or peptide.

One skilled in the art will appreciate that not all amino acids in a peptide or polypeptide need be modified. Similarly not all amino acids need be modified in the same way. Peptide derivatives, analogues and peptidomimetics of the present invention include chimeric molecules which contain two or more chemically distinct regions, each region comprising at least one amino acid or modified version thereof.

A "Wnt7a polypeptide," as used herein, encompasses a Wnt 7a protein having a polypeptide sequence corresponding to a wild-type Wnt7a sequence, or having a sequence that is at least about as 70%, more preferably about 80%, 85%, 90%, 91%, 92%, 93%, 94%, 95%, 96%, 97%, 98%, 99% or about 100%, identical to a naturally occurring Wnt7a sequence. Identity may be assessed over at least about 50, 100, 200, 300, or more contiguous amino acids, or may be assessed over the full length of the sequence. Methods for determining % identity or % homology are known in the art and any suitable method may be employed for this purpose. Wnt7a polypeptides also include variants, fragments, analogues and derivatives having an activity substantially identical to a wild-type Wnt7a polypeptide, e.g. binding to Fzd7. U.S. Pat. No. 6,297,030 describes Wnt7a polypeptides and polynucleotides and methods for producing such polypeptides by recombinant techniques. Exemplary Wnt7A polypeptides include polypeptides comprising the amino acid sequence shown in SEQ ID NO: 2 (mouse) or SEQ ID NO: 4 (human), as well as active fragments, variants or derivatives thereof.

The polypeptides of the present invention can be prepared by methods known in the art, such as purification from cell extracts or the use of recombinant techniques. Polypeptides as described herein will preferably involve purified or isolated polypeptide preparations. In certain embodiments, purification of the polypeptide may utilize recombinant expression methods well known in the art, and may involve the incorporation of an affinity tag into the expression construct to allow for affinity purification of the target polypeptide.

Shorter sequences can also be chemically synthesized by methods known in the art including, but not limited to, exclusive solid phase synthesis, partial solid phase synthesis, fragment condensation or classical solution synthesis (Merrifeld (1963) Am. Chem. Soc. 85:2149; Merrifeld (1986) Science 232:341). The polypeptides of the present invention can be purified using standard techniques such as chromatography (e.g. ion exchange, affinity, and sizing column chromatography or high performance liquid chromatography), centrifugation, differential solubility, or by other techniques familiar to a worker skilled in the art. The polypeptides can also be produced by recombinant techniques. Typically this involves transformation (including transfection, transduction, or infection) of a suitable host cell with an expression vector comprising a polynucleotide encoding the protein or polypeptide. The nucleic acid sequences for human and mouse wnt7a gene and various other components of the PCP signaling pathway are known in the art (see, for example, GenBank Accession Nos O00755, P24383, NP_004616, G36470, PF6706, P28047, H36470, NM_004625, M89801) and may be used as a basis for the polynucleotides of the invention.

The polypeptides and peptides of the present invention can also be produced as fusion proteins. One use of such fusion proteins is to improve the purification or detection of the polypeptide or peptide. For example, a polypeptide or peptide can be fused to an immunoglobulin Fc domain and the resultant fusion protein can be readily purified using a protein A column. Other examples of fusion proteins include polypeptides or peptides fused to histidine tags (allowing for purification on Nie+ resin columns), to glutathione-S-transferase (allowing purification on glutathione columns) or to biotin (allowing purification on streptavidin columns or with streptavidin labelled—19 magnetic beads). Once the fusion protein has been purified, the tag may be removed by site-specific cleavage using chemical or enzymatic methods known in the art.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

As used herein, the term "polynucleotide sequence" or "nucleic acid sequence," refers to any nucleotide sequence (e.g., RNA or DNA), the manipulation of which may be deemed desirable for any reason (e.g., modulate cell function, treat disease, etc.), by one of ordinary skill in the art. Such nucleotide sequences include, but are not limited to, coding sequences of genes (e.g., reporter genes, selection marker genes, oncogenes, disease resistance genes, growth factors, etc.), and non-coding regulatory sequences which may not encode an mRNA (e.g., promoter sequence, polyadenylation sequence, termination sequence, enhancer sequence, etc.).

The term "oligonucleotide" refers to a molecule comprised of two or more deoxyribonucleotides or ribonucleotides, preferably more than three, and usually more than ten. The exact size will depend on many factors, which, in turn, depend on the ultimate function or use of the oligonucleotide. The oligonucleotide may be generated in any manner, including chemical synthesis, DNA replication, reverse transcription, or a combination thereof.

By the terms "regulatory sequence", "regulatory region", "regulatory element" it is meant a portion of nucleic acid typically, but not always, upstream of the protein or polypeptide coding region of a nucleotide sequence, which may be comprised of either DNA or RNA, or both DNA and RNA. When a regulatory region is active, and in operative association with a nucleotide sequence of interest, this may result in expression of the nucleotide sequence of interest. A regulatory element may be capable of mediating organ specificity, or controlling developmental or temporal nucleotide sequence activation. A "regulatory region" includes promoter elements, core promoter elements exhibiting a basal promoter activity, elements that are inducible in response to a stimulus, elements that mediate promoter activity such as negative regulatory elements or transcriptional enhancers. "Regulatory region", as used herein, also includes elements that are active following transcription, for example, regulatory elements that modulate nucleotide sequence expression such as translational and transcriptional enhancers, translational and transcriptional repressors, upstream activating sequences, and mRNA instability determinants. Several of these latter elements may be located proximal to the coding region.

The terms "complementary" and "complementarity" refer to polynucleotides (i.e., a sequence of nucleotides) related by the base-pairing rules. For example, the sequence "A-G-T-" is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The term "isolated" when used in relation to a polynucleotide, refers to a nucleic acid sequence that is identified and separated from at least one contaminant nucleic acid with which it is ordinarily associated in its natural source. Isolated nucleic acid molecule is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid molecule encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid may be present in single-stranded or double-stranded form. When an isolated nucleic acid is to be utilized to express a protein, the polynucleotide will contain at a minimum the sense or coding strand (i.e., the polynucleotide may be single-stranded), but may contain both the sense and anti-sense strands (i.e., the polynucleotide may be double-stranded).

The term "purified" refers to molecules, including nucleic or amino acid sequences that are removed from their natural environment isolated or separated. An "isolated nucleic acid sequence" is therefore a purified nucleic acid sequence. "Substantially purified" molecules are at least 60% free, at least 75% free, or typically at least 90%, 95% or 99% free from other components with which they are naturally associated. As used herein, the terms "purified" and "to purify"

also refer to the removal of contaminants from a sample. The removal of contaminating molecules, including proteins, results in an increase in the percent of polypeptide of interest in the sample. In another example, recombinant polypeptides are expressed in bacteria, yeast, or mammalian host cells and the polypeptides are purified by the removal of host cell proteins; the percent of recombinant polypeptides is thereby increased in the sample.

Nucleic acid sequences corresponding to genes or encoding polypeptides relating to the present invention can be readily purchased or purified from a suitable source by standard techniques, or can be synthesized chemically. The nucleic acids can be genomic DNA, RNA, cDNA prepared from isolated mRNA, or DNA amplified from a naturally occurring nucleic acid sequence by standard techniques. Alternatively, the known sequences may be used to prepare probes to obtain other nucleic acid sequences encoding a Wnt7a polypeptide from various sources using standard techniques. Suitable sources for obtaining the nucleic acids are those cells or tissues which are known to express the proteins of interest, such as skeletal muscle tissue and other tissues with measurable Wnt7a transcripts. An example of suitable cells would be myoblasts which express Wnt7a.

Polynucleotides encoding fragments or variants of the naturally occurring Wnt7a proteins can be constructed by deletion, addition, and/or substitution of one or more nucleotides within the coding sequence using standard techniques, such as site-directed mutagenesis techniques.

Specific initiation signals may be required for efficient translation of cloned polynucleotide. These signals include the ATG initiation codon and adjacent sequences. In cases where an entire wild-type gene or cDNA, including its own initiation codon and adjacent sequences, is inserted into the appropriate expression vector, additional translational control signals may not be needed. In other cases, exogenous translational control signals, including, perhaps, the ATG initiation codon, must be provided. Furthermore, the initiation codon must be in phase with the reading frame of the desired coding sequence to ensure translation of the entire insert. The exogenous translational control signals and initiation codons can be natural or synthetic. The efficiency of expression may be enhanced by the inclusion of appropriate transcription enhancer elements and/or transcription terminators (Bittner et al. (1987) Methods in Enzymol. 153, 516).

In some instances, it may be desirable to link the coding sequence of a particular gene to an amino- or carboxyl-terminal epitope tag to facilitate detection or purification of expressed protein. Suitable epitope tags may include, but are not limited to, haemagluttanin (HA), myc, FLAG, 6×His, V5, glutathione-S-transferase (GST), etc.

An "expression vector", also known as an expression construct, is used to introduce a specific gene into a target cell. Once the expression vector is inside the cell, the protein that is encoded by the gene is produced by the cellular-transcription and translation machinery. The vector is frequently engineered to contain regulatory sequences that act as enhancer and promoter regions and lead to efficient transcription of the gene carried on the expression vector. The goal of a well-designed expression vector is the production of large amounts of stable messenger RNA.

Suitable expression vectors include, but are not limited to, plasmids, phagemids, viral particles and vectors, phages and the like. The entire expression vector, or a part thereof, can be integrated into the host cell genome. In some circumstances, it is desirable to employ an inducible expression vector as are known in the art, e.g. the LACSWITCH Inducible Expression System (Stratagene, LaJolla, Calif.).

Suitable expression vectors may comprise promoters for driving expression in a particular host cell. Some expression vectors may comprise a CMV promoter. The expression vectors may be, for example, pCMV or pCMV-Sport6.

Those skilled in the field of molecular biology will understand that a wide variety of expression systems can be used to provide the recombinant polypeptide or peptide. The polypeptide or peptide can be produced in a prokaryotic host (e.g., E. cold or B. subtilis) or in a eukaryotic host (e.g., Saccharomyces or Pichia; mammalian cells, such as COS, NIH 3T3, CHO, BHK, 293, or HeLa cells, insect cells, or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, e.g. in Cloning Vectors: A Laboratory Manual (Ponwels et al., 1985, Supp. 1987) and by various commercial suppliers.

In addition, a host cell may be chosen which modulates the expression of the inserted sequences, or modifies and processes the gene product in a specific, desired fashion. Such modifications (e.g. glycosylation) and processing (e.g. cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed heterologous protein. The host cells harbouring the expression vehicle can be cultured in conventional nutrient media adapted as needed for activation of a chosen gene, repression of a chosen gene, selection of transformants, or amplification of a chosen gene according to known procedures.

In the context of the present invention, "oligonucleotide modulators" are oligonucleotide-based inhibitors or activators that are targeted to one or more components of the Wnt7a-PCP signaling pathway genes, or genes encoding activators or effectors of the PCP pathway. Oligonucleotide modulators may, for example, include antisense oligonucleotides, short interfering RNA (siRNA) molecules, ribozymes and triple helix-forming oligonucleotides. RNA interference mediated by siRNAs is known in the art to play an important role in post-transcriptional gene silencing [Zamore, Nature Struc. Biol., 8:746-750 (2001)]. In nature, siRNA molecules are typically 21-22 base pairs in length and are generated when long double-stranded RNA molecules are cleaved by the action of an endogenous ribonuclease. Recently, it has been demonstrated that transfection of mammalian cells with synthetic siRNA molecules having a sequence identical to a portion of a target gene leads to a reduction in the mRNA levels of the target gene. For example, Vangl2 expression is inhibited with siRNA, which thereby inhibits symmetric cell division and results in an increase in asymmetric divisions. Oligonucleotide modulators can be prepared by conventional techniques well-known to those skilled in the art. For example, the oligonucleotides can be prepared using solid-phase synthesis using commercially available equipment, such as the equipment available from Applied Biosystems Canada Inc. (Mississauga, Canada). Alternatively, the oligonucleotide modulators can be prepared by enzymatic digestion and/or amplification of the naturally occurring target gene or mRNA, or of cDNA synthesized from the mRNA, using standard techniques known in the art. When the oligonucleotide inhibitors comprise RNA, they can be prepared by in vitro transcription methods also known in the art. As indicated above, siRNA molecules can also be conveniently prepared using commercially available in vitro transcription kits. Oligonucleotides can also be prepared using recombinant DNA techniques.

As used herein, "primer" refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

With reference to the polypeptide and polynucleotide sequences defined herein, the term "substantially identical" in reference to sequence identity means at least 70%, preferably at least 80%, 85%, 90%, 91%, 92%, 93%, 94%, 95%, 96%, 97%, 98% or 99% sequence identity. By "identity" is meant the number of conserved amino acids or nucleotides as determined by standard alignment algorithms or programs known in the art, used with default parameters established by each supplier. It will be understood that the degree of identity may be represented by a range defined by any two of the values listed above or any value therebetween. Identity may be assessed, for example, over at least about 50, 100, 200, 300, or more contiguous amino acids, or at least about 50, 100, 200, 300, 500, 750, 1000 or more nucleotides, or may be assessed over the full length of the sequence. The terms "homology" and "identity" are often used interchangeably. Methods for determining % identity or % homology are known in the art and any suitable method may be employed for this purpose. In general, sequences are aligned so that an optimized match is obtained. Examples of an algorithm that is suitable for determining percent sequence identity is algorithms such as the BLAST algorithm, as is well known to those skilled in the art. Software for performing BLAST analyses is publicly available through the National Center for Biotechnology Information (http://www.ncbi.nlm.nih.gov). Other commercially or publicly available programs include the DNAStar MegAlign program (Madison, Wis.) and the University of Wisconsin Genetics Computer Group (UWG) Gap program (Madison Wis.).

As used herein, the term at "least 90% identical" would refer to percent identities from 90 to 99.99% relative to a reference polynucleotide or polypeptide. Identity at a level of 90% or more is indicative of the fact that, assuming for exemplification purposes a test and reference polynucleotide or polypeptide length of 100 nucleotides or amino acids are compared, no more than 10% of the respective nucleotides or amino acids in the test polypeptide would differ from corresponding aligned positions of the reference nucleotides/polypeptides. Differences may be represented as point mutations randomly distributed over the entire length of an polynucleotide or amino acid sequence or may be clustered in one or more locations of varying length up to the maximum allowable, e.g. 10 of 100 nucleotide/amino acid differences for the above "at least 90% identity" example. Differences may be defined as nucleic acid or amino acid substitutions or deletions.

Substantially identical nucleic acid molecules would hybridize typically at moderate stringency or at high stringency conditions along the length of the nucleic acid or along at least about 70%, 80%, 85%, 90%, 95%, 96%, 97%, 98%, 99% of the full length nucleic acid molecule of interest. In the case of coding sequences, also contemplated are nucleic acid molecules that contain degenerate codons in place of codons in the hybridizing nucleic acid molecule.

As used herein, "domain" refers to a portion of a molecule, e.g., polypeptide or the encoding polynucleotide, that is structurally and/or functionally distinct from other portions of the molecule. For example, Fzd7 comprises a putative cysteine-rich Wnt-binding domain comprising residues 45 to 169 of the polypeptide shown as SEQ ID NO: 6 (mouse) and SEQ ID NO: 8 (human). Based on homology exhibited between human/mouse Fzd7 and mouse Fzd8 and Fzd3 (for which crystal structures of the respective WNT-binding domain have been reported), residues 56, 58-60, and 62-64 of human/mouse Fzd7 may be particularly important for interaction with Wnt7a. As another example, the final four residues of each of SEQ ID NOs: 6 and 8 encode a putative PDZ-binding motif (specifically residues 569-572 of SEQ ID NO: 6 and residues 571-574 of SEQ ID NO: 8) (see, for example, Dann et al. Nature, 412, Jul. 5, 2001, p. 86-90).

As used herein, "gene therapy" includes both ex vivo and in vivo techniques. Thus host cells can be genetically engineered ex vivo with a polynucleotide, with the engineered cells then being provided to a patient to be treated. Delivery of the active agent in vivo may involve a process that effectively introduces a molecule of interest (e.g. Wnt-7A polypeptide or other activator of PCP-signaling) into the cells or tissue being treated. In the case of polypeptide-based active agents, this can be effected directly or, alternatively, by transfecting transcriptionally active DNA into living cells such that the active polypeptide coding sequence is expressed and the polypeptide is produced by cellular machinery. Transcriptionally active DNA may be delivered into the cells or tissue, e.g. muscle, being treated using transfection methods including, but not limited to, electroporation, microinjection, calcium phosphate coprecipitation, DEAE dextran facilitated transfection, cationic liposomes and retroviruses. In certain embodiments, the DNA to be transfected is cloned into a vector. Such vectors may include plasmids effective for delivery and expression of the DNA within a host cell. Such vectors may include but are not limited to plasmids derived from human cytomegalovirus (hCMV) or other suitable promotors such as hPGK-1 or hACT.

Alternatively, cells can be engineered in vivo by administration of the polynucleotide using techniques known in the art. For example, by direct injection of a "naked" polynucleotide (Feigner and Rhodes, (1991) Nature 349: 351-352; U.S. Pat. No. 5,679,647) or a polynucleotide formulated in a composition with one or more other agents which facilitate uptake of the polynucleotide by the cell, such as saponins (see, for example, U.S. Pat. No. 5,739,118) or cationic polyamides (see, for example, U.S. Pat. No. 5,837,533); by microparticle bombardment (for example, through use of a "gene gun", Biolistic, Dupont); by coating the polynucleotide with lipids, cell-surface receptors or transfecting agents; by encapsulation of the polynucleotide in liposomes, microparticles, or microcapsules; by administration of the polynucleotide linked to a peptide which is known to enter the nucleus; or by administration of the polynucleotide linked to a ligand subject to receptor-mediated endocytosis (see, for example, Wu and Wu, (1987) J: Biol. Chem. 262:4429-4432), which can be used to target cell types specifically expressing the receptors.

Alternatively, a polynucleotide-ligand complex can be formed in which the ligand comprises a fusogenic viral peptide to disrupt endosomes, allowing the polynucleotide to avoid lysosomal degradation; or the polynucleotide can be targeted for cell specific uptake and expression in vivo by targeting a specific receptor (see, for example, International Patent Applications WO 92/06180, WO 92/22635, WO92/203167 WO93/14188 and WO 93/20221). The present invention also contemplates the intracellular introduction of the polynucleotide and subsequent incorporation within host cell DNA for expression by homologous recombination (see, for example, Koller and Smithies (1989) Proc. Natl. Acad. Sci. USA 86:8932-8935; Zijlstra et al. (1989) Nature 342:435-438).

The polynucleotide can be incorporated into a suitable expression vector. A number of vectors suitable for gene therapy applications are known in the art (see, for example, Viral Vectors: Basic Science and Gene Therapy, Eaton Publishing Co. (2000)) and may be used. The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia* cold and *Bacillus subtilis*, with many being designed particularly for use in mammalian systems. Examples of plasmids that may be used in the present invention include, but are not limited to, the expression vectors pRc/CMV (Invitrogen), pCR2. 1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or pVAX (Invitrogen).

Alternatively, the expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous genes in vivo, particularly into humans. These vectors provide efficient delivery of genes into cells, and the transferred polynucleotides are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leulcemia Virus, spleen necrosis virus, retroviruses such as Rous Sarcoma Virus, Harvey Sarcoma Virus, avian leulcosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

The polynucleotide is usually incorporated into the vector under the control of a suitable promoter that allows for expression of the encoded polypeptide in viva. Suitable promoters which may be employed include, but are not limited to, adenoviral promoters, such as the adenoviral major late promoter, the E1A promoter, the major late promoter (MLP) and associated leader sequences or the E3 promoter; the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTR, the histone, pot III, and (pectin promoters; B 19 parvovirus promoter; the SV40 promoter; and human growth hormone promoters. The promoter also may be the native promoter for the gene of interest. The selection of a suitable promoter will be dependent on the vector, the host cell and the encoded protein and is considered to be within the ordinary skills of a worker in the art.

The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D.; 1990) Blood 76:271). Thus, recombinant retrovirus can be constructed in which part of the retroviral coding sequence (gag, pot, env) has been replaced by subject polynucleotide and renders the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.), J. Wiley & Sons, (1989), Sections 9.10-9.14 and other standard laboratory manuals. Examples of suitable packaging virus lines for preparing both ecotropic and amphotropic retroviral systems include Crip, Cre, 2 and Am. Other examples of packaging cells include, but are not limited to, the PE501, PA317, I-2, yr-3S AM, PA12, T1 9-14X, VT-1 9-1 7-H2, ACRE, SCRIP, GP+E-86, GP+envAml2, and DAN cell lines as described in Miller, Human Gene Therapy, Vol. 1, pas. 5-14 (1990).

Furthermore, it has been shown that it is possible to limit the infection spectrum of retroviruses and consequently of retroviral-based vectors by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079-9083; Julan et al. (1992) J. Gen Virol 73:3251-3255; and Goud et al. (1983) Virology 163:251-254); or coupling cell surface receptor ligands to the viral env proteins (Neda et al. (1991) J. Biol Chem 266:14143-14146). Coupling can be in the form of the chemical cross-linking with a protein or other variety (for example, lactose to convert the env protein to an asialoglycoprotein), as well as by generating fusion proteins (for example, single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the polynucleotides contained in the vector.

Another viral vector useful in gene therapy techniques is an adenovirus-derived vector. The genome of an adenovirus can be manipulated such that it encodes and expresses a gene product of interest but is inactivated in terms of its ability to replicate in a normal lytic viral life cycle. See for example Beriner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl 324 or other strains of adenovirus (for example, Adz, Ad3, Adz etc.) are well known to those skilled in the art. Recombinant adenoviruses can be advantageous in certain circumstances in that they can be used to infect a wide variety of cell types, including peripheral nerve cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (for example, retroviral DNA). Moreover, the carrying capacity of the adenoviral genome for foreign DNA is large (up to 8 kilobases) relative to other gene delivery vectors (Berliner et al. cited supra; Haj-Ahmand and Graham (1986) J. Virol. 57:267). Most replication-defective adenoviral vectors currently in use and contemplated by the present invention are deleted for all or parts of the viral E2 and E3 genes but retain as much as 80% of the adenoviral genetic material (see, e.g., Jones et al. (1979) Cell 16:683; Berliner et al., supra; and Graham et al. in Methods in Molecular Biology, E. J. Murray, Ed. (Humane, Clifton, N.J., 1991) vol. 7. pp. 109-127). Generation and propagation of replication-defective human adenovirus vectors requires a unique helper cell line. Helper cell lines may be derived from human cells such as human embryonic kidney cells, muscle cells, hematopoetic cells or other human embryonic mesenchymal or epithelial cells. Alternatively, the helper cells may be derived from the cells of other mammalian species that are permissive for human adenovirus, i.e. that provide, in bans, a sequence necessary to allow for replication of a replication-deficient virus. Such cells include, for example, 293 cells, Vero cells or other monkey embryonic mesenchymal or epithelial cells. The use of non-human adenovirus vectors, such as porcine or bovine adenovirus vectors is also contemplated. Selection of an appropriate viral vector and helper cell line is within the ordinary skills of a worker in the art.

As used herein, "subject" may be a mammalian subject, for example, but not limited to mouse, cow, sheep, goat, pig, dog, cat, rat, rabbit, primate, or human.

A "pharmaceutical composition", often used interchangeably with composition, includes at least one active agent for carrying out a desired effect. The pharmaceutical composition further comprises one or more physiologically acceptable diluents, carriers or excipients. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000).

A "cell composition" is a composition that contains cells together with one or more physiologically acceptable diluents, carriers or excipients. The cell composition may further comprise one or more active agents. In some cases, the cells may be transformed to express a gene or protein of interest.

A "stem cell composition" is a composition that contains stem cells together with one or more physiologically acceptable diluents, carriers or excipients. The stem cell composition may comprise one or more active agents, such as a stem cell modulator. In some cases, the stem cells may be transformed to express a gene or protein of interest.

An "effective amount" is an amount sufficient to achieve a beneficial or desired result. An effective amount may be effective amount in vitro or in vivo. In vivo, an effective amount may also be referred to as a "therapeutically effective amount", which can be administered to a patient in one or more doses. In terms of treatment of disease or damage, an effective amount may be an amount that is sufficient to palliate, ameliorate, stabilize, reverse or slow the progression of the disease or damage. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition and the form and effective concentration of the antigen-binding fragment administered.

As used herein, the term "about" refers to a +/−5% variation from the nominal value. It is to be understood that such a variation is always included in any given value provided herein, whether or not it is specifically referred to.

Embodiments of the invention are included within the definitions above, which may be relied upon to define the invention.

In one aspect, there is provided a composition for modulating the division symmetry of a stem cell comprising as an active agent a modulator of planar cell polarity (PCP) signaling in the stem cell. Preferably, the stem cell is an adult stem cell, for example, a satellite stem cell.

In some embodiments, the active agent is an activator of PCP signaling capable of promoting symmetrical division of the stem cell. An activator may comprise one or a combination of molecules. Polypeptide and peptide activators of the PCP signaling pathway include direct activators, as well as activators that exert their activating effect by inhibiting the activity or expression of proteins that inhibit Wnt7a signaling, i.e. indirect activators.

The compositions described herein are useful in vitro or in vivo to promote stem cell expansion. It was demonstrated that activation of the PCP pathway, or components thereof, in satellite stem cells promotes symmetrical stem cell division, largely expanding the stem cell pool without affecting the rate of cell division.

The active agent may, for example, comprise a small molecule, a polynucleotide, a peptide, a polypeptide, a macromolecule, or a combination thereof.

The components of the PCP pathway, including Wnt7a and Fzd7, tend to be highly conserved across species. Therefore, polypeptides and polynucleotides derived from various species are contemplated within the scope of the invention so long as they have the desired characteristics and activity.

In some embodiments, the active agent comprises a peptide or polypeptide capable of binding to and/or activating Fzd7 on the stem cell. Fzd7 comprises a putative cysteine-rich Wnt-binding domain comprising residues 45 to 169 of the polypeptide shown as SEQ ID NO: 6 (mouse) and SEQ ID NO: 8 (human). Based on homology exhibited between human/mouse Fzd7 and mouse Fzd8 and Fzd3 (for which crystal structures o the respective Wnt-binding domain have been reported), residues 56, 58-60, and 62-64 of human/mouse Fzd7 may be particularly important for interaction with Wnt7a. Thus, a polypeptide capable of activating Fzd7 may comprise a polypeptide capable of binding to a Wnt-binding domain of Fzd7.

In some embodiments, the active agent is a Wnt7a polypeptide or an active analogue, variant, fragment, or derivative thereof capable of binding to and activating Fzd7. Exemplary Wnt7a polypeptides are shown in FIG. 22 (SEQ ID NO: 2) and 24 (SEQ ID NO: 4), which are mouse an human sequences, respectively.

In some embodiments, the active agent is a polypeptide having a sequence of a Wnt7a polypeptide, or a sequence that is at least about 70%, 80%, 85%, 90%, 91%, 92%, 93%, 94%, 95%, 96%, 97%, 98% or 99% identical to a Wnt7a polypeptide. In some embodiments the sequence of the Wnt7a polypeptide comprises SEQ ID NO: 2 or SEQ ID NO: 4.

In some embodiments, the active agent is a Wnt7a polypeptide having an amino acid sequence comprising SEQ ID NO: 2 or SEQ ID NO: 4, or a sequence that is at least about 70%, 80%, 85%, 90%, 91%, 92%, 93%, 94%, 95%, 96%, 97%, 98% or 99% identical to SEQ ID NO: 2 or SEQ ID NO: 4.

In some embodiments, the % identity is assessed over at least about 50, 100, 200, 300, or more contiguous amino acids. In some embodiments, the % identity is assessed over the full length of the mature peptide sequence.

In certain embodiments, the active agent comprises a Wnt7a polypeptide. In some embodiments, the Wnt7a polypeptide is a human Wnt7a polypeptide. In some embodiments, the Wnt7a polypeptide is a murine Wnt7a polypeptide. Other species are also contemplated.

In some embodiments, the Wnt7a polypeptide has an amino acid sequence comprising or consisting of SEQ ID NO: 2 or SEQ ID NO: 4.

In some embodiments, the active agent comprises an isolated polynucleotide encoding a peptide or polypeptide capable of binding to and/or activating Fzd7. The peptide or polypeptide capable of binding to and/or activating Fzd7 may be as described above. Thus, in some embodiments, the polynucleotide encodes a Wnt7a polypeptide or an active analogue, variant, fragment, or derivative thereof capable of binding to and activating Fzd7.

Exemplary Wnt7a polynucleotides are shown in FIG. 21 (SEQ ID NO: 1) and 23 (SEQ ID NO: 3), which are mouse an human sequences, respectively.

In some embodiments, the active agent comprises a polynucleotide encoding a polypeptide having an amino acid sequence comprising SEQ ID NO: 2 or SEQ ID NO: 4, or a sequence that is at least about 70%, 80%, 85%, 90%, 91%, 92%, 93%, 94%, 95%, 96%, 97%, 98% or 99% identical to SEQ ID NO: 2 or SEQ ID NO: 4.

In some embodiments, the active agent comprises a polynucleotide having an amino acid sequence comprising SEQ ID NO: 1 or SEQ ID NO: 3, or a sequence that is at least about 70%, 80%, 85%, 90%, 91%, 92%, 93%, 94%, 95%, 96%, 97%, 98% or 99% identical to SEQ ID NO: 1 or SEQ ID NO: 3.

In some embodiments, the % identity is assessed over at least about 50, 100, 200, 300, 500, 750 or 100 or more contiguous nucleotides. In some embodiments, the % identity is assessed over the full length of the polynucleotide.

In some embodiments, the polynucleotide comprises a Wnt7a polynucleotide sequence comprising or consisting of SEQ ID NO: 1 or SEQ ID NO: 3.

In some embodiments, the active agent is a small molecule capable of binding to and/or activating Fzd7.

In some embodiments, the active agent is a polynucleotide or polypeptide capable of increasing expression of Fzd7 on the stem cell. In some embodiments, the active agent comprises a Fzd7 polynucleotide. Exemplary Fzd7 polynucleotides are shown in FIGS. 25 (SEQ ID NO 5) and 27 (SEQ ID NO: 7). In some embodiments, the active agent comprises a polynucleotide having an amino acid sequence comprising SEQ ID NO: 6 or SEQ ID NO: 8, or a sequence that is at least about 70%, 80%, 85%, 90%, 91%, 92%, 93%, 94%, 95%, 96%, 97%, 98% or 99% identical to SEQ ID NO: 6 or SEQ ID NO: 8.

In some embodiments, the polypeptides correspond to modulators of Wnt7a signaling, for example, Fzd7, Fzd3, Celsr1, Celsr2, Celsr3, Dvl1, Dvl2, Dvl3, Pk1, Pk2, Pk3, Pk4, Rac/RhoA, Vangl1, Vangl2, Syndecan 4 (Syn4) and α7-β1-integrin, or active fragments, variants or derivatives thereof.

In some embodiments, the active agent comprises a polynucleotide or polypeptide capable of modulating a downstream effector molecule in the PCP pathway to thereby promote or inhibit symmetrical cell division. Exemplary polarity effectors that may be modulated to affect cell division decisions in adult stem cells include Prickle, Flamingo (Celsr2), Disheveled (Dsh) or PTK7. Exemplary targets of modulation in the PCP pathway include, but are not limited to, Fzd7, Vangl1, Vangl2, Dvl2, Dvl3, Pk1, Pk2, Celsr2 and α7-integrin.

In some embodiments, the active agent comprises a polynucleotide or polypeptide capable of activating a downstream effector molecule in the PCP pathway to thereby promote symmetrical stem cell division. The downstream effector molecule may, for example be, Vangl2, α7-integrin, Prickle 1 or Celsr2.

In one embodiment, the effector molecule is Vangl2. The active agent may, for example, be a polypeptide or polynucleotide capable of inducing expression or polarized redistribution of Vangl2 in the cell membrane.

In some embodiments, the active agent may comprise a polynucleotide encoding a Vangl2 polypeptide. Exemplary Vangl2 polypeptides are shown in FIGS. 30 (SEQ ID NO: 10) and 32 (SEQ ID NO: 12). In some embodiments, the Vangl2 polypeptide has substantially identical activity to the wild-type protein.

In some embodiments, the composition additionally comprise one or more stem cell modulators. The stem cell modulator may, for example, promote one more of stem cell proliferation, differentiation, lineage commitment, or terminal differentiation of committed progenitor cells.

In some embodiments, the modulator increases the rate of stem cell division. Any suitable activator of stem cell division rate can be used, such as a suitable growth factor. Known growth factors include FGF, HGF and SDF. In some embodiments, a growth factor that increases stem cell division rate without promoting differentiation is selected.

In some embodiments, the modulator is one that increases proliferation in a population of expanding stem cells, or one that promotes differentiation in a population of stem cells that have been previously expanded by treatment with Wnt7a.

In some embodiments, a stem cell modulator promotes stem cell survival. Exemplary compounds that enhance the survival of the stem cells would include, for example, a sonic hedgehog (Shh) protein.

In some embodiments, a stem cell modulator is an inhibitor of canonical Wnt/β-catenin signaling.

In one embodiment, there is provided a composition for enhancing tissue formation, regeneration, maintenance or repair in a mammal comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In another embodiment, there is provided a composition for promoting symmetrical stem cell division comprising as active agent one or more activators of the Fzd7 receptor, wherein the one or more activators may include, but are not limited to, one or more small molecules, nucleic acids, polypeptides, peptides, macromolecules, antibodies or a combination thereof, that activate Fzd7 receptor in adult stem cells.

In some embodiments, the adult stem cells are satellite stem cells.

The compositions described herein may be used to deliver a polynucleotide of interest into a cell or tissue. The composition may be administered in vitro, for example, to expand a population of stem cells, or in vivo, for example, in a gene therapy method.

The polynucleotide of interest may be delivered directly into a cell or tissue (e.g. naked). More typically, the polynucleotide will be cloned into an expression vector capable of expressing the encoded polypeptide. A cell or tissue may therefore be transformed to express a polypeptide of interest. Any suitable transformation method known in the art may be employed.

Various expression systems are known in the art and are publically available through a number of sources (e.g. Invitrogen, Clontech). Any suitable expression vector may be used. In some embodiments, the expression vector is a mammalian expression vector. In some embodiments, the expression vector is a plasmid. In some embodiments, the plasmid is an virally-derived plasmid. In some embodiments, the plasmid comprises a CMV promoter sequence. In some embodiments, the plasmid comprises pCMV or pCMV-Sport6. In one embodiment, the plasmid is Wnt7a-CMV.

Gene expression may optionally be under the control of an inducible promoter. Several inducible promoters are known in the art.

In some embodiments, the composition comprises an expression vector carrying a polynucleotide encoding a polypeptide capable of activating PCP signaling in a stem cell, to thereby promote symmetrical stem cell expansion.

In some embodiments, a cell or tissue is transformed to express a modulator of PCP signaling in a stem cell. A number of exemplary modulators have been described above.

In some embodiments, a cell or tissue is transformed to overexpress Wnt7a to thereby induce symmetrical division of a stem cell. Wnt7a may be secreted from the transformed cell and may act on the cell from which is it secreted or may act on a nearby stem cell. In some embodiments, the transformed cell is a helper cell that may be co-cultured or co-administered with the stem cell. The helper cell may also be a resident cell in a tissue that is transformed to overexpress Wnt7a or another protein of interest.

In some embodiments, the helper cell is a myoblast or muscle cell transformed to overexpress Wnt7a.

In some embodiments, muscle tissue is transformed to overexpress Wnt7a. In some embodiments, the muscle tissue is skeletal muscle. Overexpression of Wnt7a expands the satellite stem cell pool in vivo, increases satellite cell numbers, and promotes muscle regeneration and repair.

In some embodiments, a stem cell is transformed to overexpress Fzd7, Vangl2, α7-integrin, or another effector of PCP signaling in the stem cell.

In some embodiments, the composition comprises cells and may therefore be a cell composition. For example, the composition may comprise a helper cell. In some embodiments, the helper cell is transformed to express and secrete Wnt7a. In some embodiments, the helper cell is a myoblast or muscle cell.

In some embodiments, the composition comprises stem cells and is therefore a stem cell composition.

In some embodiments, stem cells may be expanded in vitro using a method according to the invention and may subsequently be added to a composition of the invention to form a stem cell composition. For instance, stem cells can be cultured and expanded in vitro using methods of the invention and then administered to a subject as a therapeutic stem cell composition according to methods known to skilled persons.

In some embodiments, the composition comprises: a stem cell; and an activator of PCP signaling in the stem cell. In some embodiments, the stem cell is a satellite stem cell.

In some embodiments, the composition comprises a stem cell transformed to express a polynucleotide of interest. Any suitable transformation method known in the art may be employed.

In one embodiment, there is provided a composition for enhancing tissue regeneration or repair comprising: a stem cell; and one or more activators or effectors of PCP signaling. Various activators and effectors of PCP signaling have been described above.

In some embodiments, the composition comprises a stem cell transformed to overexpress an activator or effector of the PCP pathway, for example, Wnt7a, Fzd7 or Vangl2.

The composition may comprise a physiologically acceptable diluent, carrier or excipient. Methods of making various pharmaceutical compositions for various routes of administration are known in the art and are further describe in a later section.

In some embodiments, the composition is formulated for injection. For instance, the composition may be formulated for one or more of intravenous injection, intramuscular injection, intracardiac injection, subcutaneous injection, or intraperitoneal injection. In one embodiment, the composition if for systemic injection. In one embodiment, the composition if for intramuscular injection.

In some embodiments, there is provided a use of a composition as described herein for the manufacture of a medicament for promoting stem cell expansion. In some embodiments, there is provided a composition as described herein for use in the manufacture of a medicament for promoting stem cell expansion.

In some embodiments, there is provided a use of a composition as described herein for the manufacture of a medicament for promoting muscle formation, maintenance, repair, or regeneration of muscle in a subject in need thereof. In some embodiments, there is provided a composition as described herein for use in the manufacture of a medicament for promoting muscle formation, maintenance, repair, or regeneration of muscle in a subject in need thereof.

In some embodiments, the composition is for promoting muscle regeneration or repair.

The composition may be administered in an effective amount, such as a therapeutically effective amount.

The invention provides for methods of modulating stem cells, in particular, methods of modulating division symmetry of adult stem cells, such as satellite stem cells.

In some embodiments, there is provided a method for modulating division symmetry of stem cells in vivo or in vitro comprising contacting the stem cells with a composition as described herein.

As described in the embodiments above, the composition comprises as an active agent a modulator of planar cell polarity (PCP) signaling in the stem cell.

Is some embodiments the active agent is an activator of PCP signaling in the stem cell and the method thereby promotes stem cell expansion. Such methods are useful, for example, for increasing the relative proportion of symmetrical to asymmetrical cell divisions in a population of stem cells in vivo or in vitro. Such methods are therefore useful for expanding a population of stem cells in vivo or in vitro.

In some embodiments, the methods disclosed herein are capable of promoting symmetrical stem cell division without altering the rate of stem cell division.

In some embodiments, the methods may be useful for promoting survival of a population of stem cells.

In some embodiments, the methods are administered in vitro.

In some embodiments, the methods are administered in vivo. In some embodiments, the in vivo method comprises administering the composition to a subject in need thereof.

In some embodiments, there is provided a method for expanding a population of satellite stem cells in vivo or in vitro comprising contacting the stem cells with an effective amount of a composition comprising (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In some embodiments, the active agent is a Wnt7a polypeptide or an analogue, derivative, variant or active fragment thereof.

In some embodiments, there is provided a method of promoting satellite stem cell expansion comprising contacting the satellite stem cell with Wnt7a or an active fragment, variant, analogue or derivative thereof capable of activating Fzd7.

In another embodiment, there is provided a method of increasing the number of satellite cells in a tissue, and thereby providing enhanced regeneration potential of the tissue, comprising contacting the stem cells with a composition as described herein.

In some embodiments, the methods of the invention are used in vivo for treatment of resident stem cells in a tissue, e.g. resident satellite stem cells in muscle tissue.

In some embodiments, there are provided methods of promoting stem cell expansion using compounds that activate Wnt7a, result in an increase of endogenous Wnt7a or an increase in endogenous Wnt7a activity. Wnt7a activators may be polypeptides or genes encoding polypeptides that act upstream of Wnt7a in vivo to upregulate expression or activity of Wnt7a, or they may be small molecule activators. Wnt7a activators may act at a genetic level, for example to upregulate the expression of a gene encoding Wnt7a, or they may act at the protein level to increase the activity of a Wnt7a polypeptide or to decrease the activity of an inhibitor of Wnt7a. Wnt7a activators can be, for example, polypeptides and peptides (or analogues, derivatives, variants or peptidomimetic compounds corresponding to polypeptides, as described above), polynucleotides, oligonucleotides, antibodies or antibody fragments, or organic or inorganic small molecules.

In some embodiments, the method may additionally comprise contacting the stem cell with one or more stem cell modulators, for example, a modulator that increases the rate of stem cell division or increases stem cell survival.

In some embodiments, the method comprises administering cells to a subject. The cells may, for example, be administered simultaneously or sequentially with a composition described herein.

In some embodiments, the method comprises administering stem cells to a subject. The stem cells may, for example, be administered simultaneously or sequentially with a composition described herein that promotes stem cell expansion. For example, the stem cells may be administered prior to administration of the composition (i.e. the composition may be administered after a desired period). In some embodiments, the composition itself may comprise the stem cells to be administered.

Stem cells may be maintained and expanded in vitro for subsequent experimental or therapeutic uses. In some embodiments, stem cells, e.g. satellite stem cells, are expanded in vitro and are subsequently administered to a subject in need thereof. For instance, stem cells can be cultured and expanded in vitro using methods of the invention and then administered to a patient as a therapeutic stem cell composition according to methods known to skilled persons.

In some embodiments, stem cells may be obtained from an individual and maintained in culture. The population of cultured stem cells may be treated with Wnt7a, or another activator of PCP signaling, to promote symmetrical expansion in vitro.

In some embodiments, the method may comprise administering helper cells to a subject. The helper cells may, for example, be administered simultaneously or sequentially with the composition. In some embodiments, the composition itself may comprise helper cells.

The present invention also contemplates administration of polynucleotides encoding Wnt7a, a variant or active fragment thereof, or another activator of PCP signaling, and optionally a stem cell modulator, which then express the encoded product in vivo, by various gene therapy methods known in the art.

In some embodiments, the method comprises transforming a cell or tissue. Some exemplary methods have been described previously above. Various methods of transformation are known to those of skill in the art.

In some embodiments, a cell or tissue is transformed to express Wnt7a, or an active fragment or variant thereof, which is then secreted and acts at the surface of stem cells by binding to the Fzd7 receptor.

In some embodiments, helper cells are transformed to overexpress Wnt7a, or an active fragment or variant thereof.

In some embodiments, stem cells are transformed to express Fzd7 or an effector of PCP signaling, such as Vangl2.

In some embodiments, satellite stem cells are transformed to overexpress Wnt7a, or an active fragment or variant thereof, or another activator of PCP signaling. In one embodiment, satellite stem cells are transformed to overexpress Vangl2. In another embodiment, satellite stem cells are transformed to overexpress Fzd7.

In some embodiments, stem cells are co-cultured with a differentiated cell transformed to overexpress and secrete Wnt7a or another stimulator of PCP signaling in the stem cell, e.g. an activator of Fzd7.

In one embodiment, satellite stem cells are co-cultured with muscle cells transformed with CMV-Wnt7a to overexpress and secrete Wnt7a.

Any suitable expression vector may be used, including but not limited to those described previously. Where in vivo methods are performed, cell- or tissue-specific vectors or promoters may also be used. In one embodiment, the vector is a muscle-specific AAV vector. An inducible promoter may optionally be used.

Polypeptide activators or effectors of PCP-signaling may be directly introduced into cells, bypassing the DNA transfection step. Means to directly deliver polypeptides into cells include, but are not limited to, microinjection, electroporation, cationic lipids and the construction of viral fusion proteins. Typically, transfection of a suitable expression system carrying a polynucleotide will be used.

The methods of promoting stem cell expansion can be used to stimulate the ex vivo or in vitro expansion of stem cells and thereby provide a population of cells suitable for transplantation or administration to a subject in need thereof.

The stem cells to be administered may be treated with a stem cell modulator, for example, a modulator that promotes survival of a stem cell. Sequential methods that promote expansion followed by proliferation and/or differentiation of stem cells are also contemplated. For example, a stem cell population may be expanded in vitro by contacting the cells, directly or indirectly, with Wnt7a or another activator of PCP signaling. The expanded population of cells may then be treated with one or more stem cell modulators in vitro or in vivo, e.g. that promote proliferation and/or differentiation of the stem cells in situ or promote stem cell survival. Alternatively, both steps may be conducted in vitro prior to administration of the cells to a subject.

In vitro is sometimes used interchangeably with ex vivo herein. For in vivo and ex vivo transplant methods, the stem cells can be autologous, allogeneic or xenogeneic. In embodiments where stem cells from a donor subject are transplanted into a recipient subject in need thereof, preferably, the donor and recipient are matched for immunocompatibility. For example, but not wishing to be limiting, it is preferable that the donor and the recipient are matched for compatibility to the major histocompatibility complex (MHC) (human leukocyte antigen (HLA))-class I (e.g., loci A, B, C) and -class II (e.g., loci DR, DQ, DRW) antigens. Immunocompatibility between donor and recipient may be determined according to methods generally known in the art (see, e.g., Charron, D. J., Curr. Opin. Hematol., 3: 416-422 (1996); Goldman, J., Curr. Opin. Hematol., 5: 417-418 (1998); and Boisjoly, H. M. et al., Opthalmology, 93: 1290-1297 (1986)).

In one embodiment of the present invention, the gene therapy vector is an adenovirus-derived vector.

In one embodiment, Wnt7a-CMV is administered to a patient under the control of a muscle-specific promoter or vector.

In some embodiments, the subject is a human.

The methods described herein have a number of applications. For example, the methods can be used in vitro to promote expansion of stem cells wherein the cells are destined for further in vitro use, for example, for research or diagnostic purposes. The methods can be used for maintaining stem cell cultures in vitro and also have potential application in the development of new in vitro models for drug testing or screening.

The compositions and methods described herein are also useful for various therapeutic applications. In particular, the compositions and methods described herein are useful for promoting tissue formation, regeneration, repair or maintenance in a subject in need thereof. In some embodiments, the tissue is muscle. In some embodiments, the muscle is skeletal muscle.

Relevant therapeutic applications may pertain to situations where there is a need to regenerate lost or damaged muscle tissue, for example, after chemotherapy or radiation therapy, after muscle injury, or in the treatment or management of diseases and conditions affecting muscle. In some embodiments, the disease or condition affecting muscle may include a wasting disease (e.g. cachexia, which may be associated with an illness such as cancer or AIDS), muscular attenuation or atrophy (e.g. sarcopenia, which may be associated with aging), ICU-induced weakness, prolonged disuse (e.g. coma, paralysis), surgery-induced weakness (e.g. following hip or knee replacement), or a muscle degenerative disease (e.g. muscular dystrophies). This list is not exhaustive.

In some embodiments, compositions and methods described herein are employed where there is a need to prevent loss of tissue, as in wasting diseases or atrophy.

In some embodiments, compositions and methods described herein are employed where there is a need or desire to increase the proportion of resident stem cells, or committed precursor cells, in a muscle tissue, for example, to replace damaged or defective tissue, or to prevent muscle atrophy or loss of muscle mass, in particular, in relation to diseases and disorders such as muscular dystrophy, neuromuscular and neurodegenerative diseases, muscle wasting diseases and conditions, atrophy, cardiovascular disease, stroke, heart failure, myocardial infarction, cancer, HIV infection, AIDS, and the like.

In some embodiments, the methods can be used with satellite stem cells in the treatment, management or prevention of degenerative muscle disorders.

In some embodiments, the compositions and methods are useful for promoting muscle cell formation, for example, for repairing or regenerating dysfunctional skeletal muscle, for instance, in subjects having muscle degenerative diseases.

The subject may therefore have, be suspected of having, or be at risk of at having skeletal muscle damage, degeneration or atrophy. The skeletal muscle damage may be disease related or non-disease related. The human subject may exhibit or be at risk of exhibiting muscle degeneration or muscle wasting. The muscle degeneration or muscle wasting may be caused in whole or in part by a disease, for example aids, cancer, a muscular degenerative disease, or a combination thereof.

Muscle degeneration may be due to a muscle degeneration disease such as muscular dystrophy.

Examples of muscular dystrophies include, but are not limited to Duchenne muscular dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy. See, e.g., Hoffman et al., N. Engl. J. Med., 318.1363-1368 (1988); Bonnemann, C. G. et al., Curr. Opin. Ped., 8: 569-582 (1996); Worton, R., Science, 270: 755-756 (1995); Funakoshi, M. et al., Neuromuscul. Disord., 9(2): 108-114 (1999); Lim, L. E. and Campbell, K. P., Cure. Opin. Neurol., 11(5): 443-452 (1998); Voit, T., Brain Dev., 20(2): 65-74 (1998); Brown, R. H., Annu. Rev. Med., 48: 457-466 (1997); Fisher, J. and Upadhyaya, M., Neuromuscul. Disord., 7 (1): 55-62 (1997).

In some embodiments, the muscular dystrophy is Duchenne muscular dystrophy (DMD).

In some forms of urinary continence, the culprit muscle can be treated with a composition or method of the invention, for example, by electroporation of the muscle. Thus, in one embodiment, the method is useful for treating urinary incontinence.

In one aspect, there is provided a method for promoting muscle formation, regeneration or repair in a subject in need thereof comprising administering to the mammal a composition comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In another aspect, there is provided a method for preventing muscle wasting, atrophy or degeneration in a subject in need thereof comprising administering to the mammal a therapeutically effective amount of a composition comprising (a) a Wnt7a polypeptide or an active variant, fragment, analogue or derivative thereof capable of binding to and activating Fzd7, or (b) a polynucleotide encoding a Wnt7a polypeptide or an active variant, fragment, analogue or derivative thereof capable of binding to and activating Fzd7.

In some aspects, the compositions and methods described herein are useful for promoting formation, maintenance, repair or regeneration of skeletal muscle in a human subject in need thereof. In one aspect, there is provided a method for enhancing tissue formation, regeneration, maintenance or repair in a mammal comprising administering to a subject in need thereof a composition comprising as an active agent (a) a Wnt7a polypeptide or an active variant, fragment, analogue or derivative thereof capable of binding to and activating Fzd7, or (b) a polynucleotide encoding a Wnt7a polypeptide or an active variant, fragment, or derivative thereof capable of binding to and activating Fzd7.

The promotion of muscle cell formation can further be, in an embodiment, for preventing or treating muscle destruction or atrophy of a subject, e.g. in subjects with disuse atrophy or sarcopenia. In some embodiments, the compositions are used to treat or prevent atrophy and to maintain muscle mass.

The promotion of muscle cell formation can also be, in an embodiment, for repairing damaged muscle tissue. In an alternative embodiment, the promotion of muscle cell formation can be for increasing muscle mass in a subject.

In a further embodiment, damaged or dysfunctional muscle tissue may be caused by an ischemic event. For instance, the damaged muscle tissue may be cardiac muscle damaged by a cardiovascular event such as myocardial infarct, or heart failure.

In a further embodiment, damaged or dysfunctional muscle tissue may be cardiac muscle. For instance, the damaged muscle tissue may be cardiac muscle damaged by a cardiovascular event such as myocardial infarct, or heart failure, where the target stem cell would be a cardiac stem sell. In accordance with another aspect of the present invention, there is provided a method of promoting cardiac stem cell expansion in a mammal comprising administering to said mammal an effective amount of a composition as described herein.

The compositions and methods described herein may be used in combination with other known treatments or standards of care for given diseases, injury, or conditions. For example, in the context of muscular dystrophy, a composition of the invention for promoting symmetrical stem cell expansion can be administered in conjunction with such compounds as CT-1, pregnisone or myostatin. The treatments may be administered together, separately or sequentially.

The present invention also contemplates methods of inhibiting symmetrical stem cell expansion, for example, using compounds that inhibit components of PCP signaling pathway. In another aspect, there is provided a method for promoting asymmetrical stem cell division comprising contacting a stem cell or population of stem cells with an inhibitor of PCP signaling.

In one aspect, there is provided a composition wherein the active agent is an inhibitor of PCP signaling capable of inhibiting symmetrical division of the stem cell. The inhibitor may, for example, be a peptide, polypeptide, polynucleotide or small molecule capable of directly or indirectly inhibiting PCP signaling via inhibition of Wnt7a, Fzd7, or a an effector molecule in the PCP pathway, e.g., Vangl2, α7-integrin, Prickle 1 or Celsr2.

In some embodiments, the inhibitor is a polynucleotide capable of inhibiting expression of Wnt7a, Fzd7, or an effector molecule in the PCP pathway, e.g. siRNA or miRNA. In one embodiment, the inhibitor is Vangl2 siRNA or Fzd7 siRNA.

Inhibition of PCP signaling in stem cells could be used, for example, in the treatment of cancer, such as in the case of muscle tumors rhabdomyosarcoma, or to treat diseases such as Fibrodysplasia Ossificans Progressiva.

In some embodiments, the method may comprise contacting stem cells with an inhibitor of canonical Wnt/β-catenin signaling in the stem cell. Such inhibition may further promote symmetrical stem cell division. In some embodiments, the composition may comprise a polynucleotide or polypeptide inhibitor of canonical Wnt/β-catenin signaling in the stem cell.

The present invention further provides pharmaceutical compositions comprising Wnt7a, an analogue, derivative, variant or active fragment thereof, another activator or effector of PCP signaling, and a pharmaceutically acceptable diluent or excipient. The pharmaceutical compositions may optionally further comprise one or more stem cell modulators, one or more stem cells, or a combination thereof. Administration of the pharmaceutical compositions may be via a number of routes depending upon whether local or systemic treatment is desired and upon the area to be treated. Typically, the compositions are administered systemically or locally to the area to be treated.

Administration may be topical (including ophthalmic and to mucous membranes including vaginal and rectal delivery), pulmonary (e.g. by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection, for example, but not limited to intracardial injection or infusion, or intracranial, e.g. intrathecal or intraventricular administration. In some embodiments, compositions are administered by injection or infusion.

The compositions of the present invention may be delivered in combination with a pharmaceutically acceptable vehicle. Preferably, such a vehicle would enhance the stability and/or delivery properties. Examples include liposomes, microparticles or microcapsules. In various embodiments of the invention, the use of such vehicles may be beneficial in achieving sustained release of the active component. When formulated for parenteral injection, the pharmaceutical compositions are preferably used in the form of a sterile solution, containing other solutes, for example, enough saline or glucose to make the solution isotonic.

For administration by inhalation or insufflation, the pharmaceutical compositions can be formulated into an aqueous or partially aqueous solution, which can then be utilized in the form of an aerosol. For topical use, the modulators or pharmaceutical compositions comprising the modulators can be formulated as dusting powders, creams or lotions in pharmaceutically acceptable vehicles, which are applied to effected portions of the skin.

In some embodiments, where the composition comprises a palmitoylated protein, such as Wnt7a, a lipid carrier may be employed.

The dosage requirements for the pharmaceutical compositions vary with the particular compositions employed, the route of administration and the particular subject being treated. Dosage requirements can be determined by standard clinical techniques known to a worker skilled in the art. Treatment will generally be initiated with small dosages less than the optimum dose of each compound. Thereafter the dosage is increased until the optimum effect under the circumstances is reached. In general, the pharmaceutical compositions are administered at a concentration that will generally afford effective results without causing any harmful or deleterious side effects. Administration can be either as a single unit dose or, if desired, the dosage can be divided into convenient subunits that are administered at suitable times throughout the day.

When ex vivo methods of treating the stem cells are employed, the stem cells can be administered to the subject by a variety of procedures. Typically, administration of the stem cells is localized. The stem cells can be administered by injection as a cell suspension in a pharmaceutically acceptable liquid medium. Alternatively, the stem cells can be administered in a biocompatible medium which is, or becomes in site a semi-solid or solid matrix. For example, the matrix maybe an injectable liquid which forms a semi-solid gel at the site of tissue damage or degeneration, such as matrices comprising collagen and/or its derivatives, polylactic acid or polyglycolic acid, or it may comprise one or more layers of a flexible, solid matrix that is implanted in its final boron, such as impregnated fibrous matrices. Such matrices are letdown in the art (for example, Gelfoam available from Upjohn, Kalamazoo, Mich.) and function to hold the cells in place at the site of injury, which enhances the opportunity for the administered cells to expand and thereby for a reservoir of stem cells, to develop.

The stem cells may or may not be cryopreserved at some point.

In some embodiments, the stem cells are administered with a compound for promoting stem cell expansion to minimize risk of stem cell depletion following transplantation. In some embodiments, the transplanted stem cells have been transformed to overexpress an activator of PCP signaling, such as Fzd7 or Vangl2.

In some embodiments, the stem cells are co-administered with muscle cells or other satellite cells transformed to overexpress and secrete Wnt7a.

In some embodiments, the stem cells are injected intramuscularly.

In a preferred embodiment, satellite stem cells or a composition comprising satellite stem cells is injected into muscle tissue, preferably in an area proximal to diseased, injured or damaged tissue. However, injection into the circulation or at a distal site is also contemplated. Intracardiac administration is also contemplated.

The present invention additionally provides for kits comprising a composition as described herein together with one or more of instructions for use in promoting stem cell expansion or promoting tissue (e.g. muscle) formation, repair, regeneration, or maintenance.

The present invention additionally provides for therapeutic kits containing one or more modulators of the PCP pathway in stem cells, in pharmaceutical compositions.

The present invention additionally provides for therapeutic or diagnostic kits containing Wnt7a, an analogue, derivative, variant or active fragment thereof, or another activator of PCP signaling, and optionally one or more stem cell modulators in pharmaceutical compositions.

Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human or animal administration.

When the components of the kit may be provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient.

The components of the kit may also be provided in dried or lyophilized form and the kit can additionally contain a suitable solvent for reconstitution of the lyophilized components. Irrespective of the number or type of containers, the kits of the invention also may comprise an instrument for assisting with the administration of the composition to a patient. Such an instrument may be an inhalant, syringe, pipette, forceps, measured spoon, eye dropper or any such medically approved delivery vehicle.

Further, in addition to using the stem cells in transplants, stem cells, or compositions comprising stem cells may be used as a research tool and/or as part of a diagnostic assay or kit. Without wishing to be limiting a kit may comprise muscle stem cells, a promoter of Wnt 7a signaling, cell culture or growth medium, cell cryopreservation medium, one or more pharmaceutically acceptable delivery media, one or more nucleotide sequences or genetic constructs, one or more devices for implantation or delivery of cells to a subject in need thereof, instructions for using, delivering, implanting, culturing, cryopreserving or any combination thereof the cells as described herein.

The ability of Wnt7a, analogues, derivatives, variants and active fragments thereof, or PCP activators or effectors, alone or in combination with other stem cell modulators, to promote stem cell expansion can be tested in vitro or in vivo using standard techniques including, but not limited to, those described herein. Inhibition of stem cell expansion by one more inhibitors can also be measured in vitro or in vivo.

Candidate activators and inhibitors of stem cell expansion can also be tested and identified using in vitro methods know to those skilled in the art. Methods of maintaining stem cells in culture are known in the art (see, for example, Madlambayan, G. J., et al., (2001) J. Hematother. Stem Cell Res. 10, 481-492; Hierlihy, A. M., et al., (2002) FEBS Lett. 530, 239-243; Asakura, A., et al., (2002) J Cell Biol. 159, 123-134). The stem cells can be cultured alone as a monoculture or they can be co-cultured with educator cells. Additional steps may be included in the screening methods before, during, or after the culture period, such as steps to identify or isolate cell populations or otherwise contribute to the success of the assay. For example, growth factors or other compounds may be employed to isolate and expand the stem cell population. EGF and FGF have been used for this purpose with neural stem cells as described by Gritti et al (J. Neurosci. (1999) 19:3287-3297), and 13c1-2 has been used in the isolation of "muscle stem cell" populations (see U.S. Pat. No. 6,337,184). In one embodiment, the culture medium used in DMEM plus 10% FCS.

Various screening methods known in the art can be employed to identify candidate activators of Wnt7a or another component of the PCP pathway, such as Vangl2. For example, activators that up- or down-regulate a target gene can be identified by monitoring cells treated with the candidate activator for an increase or decrease in the expression of the target gene. Methods such as Northern blot analysis, quantitative RT-PCR or microarray analysis can be used for this purpose. Alternatively, an increase or decrease in the corresponding protein level can be monitored, for example, by Western blot analysis.

For polypeptide or peptide activators (or analogues, derivatives, variants or peptidomimetic compounds corresponding to the polypeptides) that bind a specific protein, for example, Fzd7, the binding ability can be determined using one of a variety of binding assays known in the art (see, for example, Coligan et al., (eds.) Current Protocols in Protein Science, J. Wiley & Sons, New York, N.Y.).

For antibody or antibody fragment activators, various immunoassays can be used.

In order to identify potential enhancers of symmetrical stem cell division, a population of stem cells can be cultured and exposed to various test compounds. Furthermore, stem cells can be transfected to express various test genes of interest. Alternatively, stem cells can be co-cultured with "educator" cells, the educator cells are exposed to the test compound(s) and at least one indicator of expansion is subsequently monitored in the stem cells. Educator cells may be exposed to the test compound(s) prior to, or during, co-culture. Adult stem cells derived from a variety of tissues can be used. Examples include, but are not limited to, stem cells from cardiac or skeletal muscle, pancreatic tissue, neural tissue, liver tissue or bone marrow, haematopoletic cells, myoblasts, hepatocytes, thymocytes, cardiomyocytes, and the like. Embryonic stem cells may also be used.

Generally, a compound is tested over a range of concentrations, typically about a 1000-fold range, and a suitable exposure protocol can be readily established by one skilled in the art. When a co-culture is used, stem cell exposure to a compound can occur before, during or after the initial exposure of the stem cells to the educator cells.

Alternatively, when the test compound is a polynucleotide or a compound encoded by a polynucleotide, such as a polypeptide or peptide, the stem cells can be transfected with the nucleic acid, or an expression vector comprising the polynucleotide, using standard methods described herein and elsewhere, such that the test compound is produced endogenously. Additionally, the stem cells can be exposed to a test compound by co-culture of the stem cells with another cell line, which has been transfected with the polynucleotide, or an expression vector comprising the polynucleotide, and which expresses the test compound.

As indicated above, it is further contemplated that the stem cells may not be directly exposed to the compound. For example, an educator cell population or a third cell type can be first treated with the compound and subsequently co-cultured with the stem cells. Alternatively, the stem cells can be indirectly exposed by the addition of medium that has been conditioned by such a cell population, but which is not itself included in the co-culture. In addition, it is contemplated that the stem cells may be exposed to a compound that has been incorporated into a non-liquid medium of the culture, for example, a solid, gel or semi-solid growth support such as agar, a polymer scaffold, matrix or other construct.

Indicators of stem cell expansion may be monitored qualitatively or quantitatively and include, for example, changes in gross morphology, total cell number, histology, histochemistry or immunohistochemistry, or the presence, absence or relative levels of specific cellular markers. The presence, absence or relative levels of cellular markers can be analyzed by, for example, histochemical techniques, immunological techniques, electrophoresis, Western blot analysis, FACS analysis, flow cytometry and the like. Alternatively the presence of mRNA expressed from the gene encoding the cellular marker protein can be detected, for example, using PCR techniques, Northern blot analysis, the use of suitable oligonucleotide probes and the like.

For those cells treated with both Wnt7a (or another PCP activator or effector) and a stem cell modulator, one or more indicators of differentiation may also be monitored in the stem cell population after treatment with the modulator. Typically differentiation is monitored by changes in gross morphology, as described above, or by the presence of lineage specific cellular markers, which can be analyzed using a number of standard techniques as indicated above. Suitable lineage-specific cellular markers that can be monitored are known in the art.

Furthermore screening methods can be employed to identify new modulators capable of promoting stem cell expansion or promoting muscle regeneration and repair.

In one aspect of the invention, there is provided a method of screening for a compound useful in the repair or regeneration of muscle. For example, the method could comprise (a) providing a population of satellite stem cells; (b) treating the stem cells with a test compound; and (c) determining the proportion of symmetrical to asymmetrical divisions of the treated stem cells compared to control, wherein a increase in the proportion of symmetrical divisions compared to control indicates that the compound is useful in the repair or regeneration of muscle.

In another aspect of the invention, there is provided a method of screening for a compound useful in the repair or regeneration of muscle. For example, the method could comprise (a) providing a population of satellite stem cells; (b) treating the stem cells with a test compound; and (c) determining whether the compound activates stimulates PCP signaling in the treated stem cells, wherein a increase in PCP signaling indicates that the compound is useful in the repair or regeneration of muscle.

In some embodiments, the stimulation of PCP signaling occurs via activation of Fzd7. In some embodiments, the increase is an increase of at least about 10%, 25%, 50%, 75% or greater.

Alternatively, the ability of Wnt7a, analogues, derivatives, variants and active fragments thereof, or another activator or effector of PCP signaling, to promote stem cell expansion, optionally in combination with one or more stem cell modulators, may be tested in vivo on resident stem cell populations in an appropriate experimental animal. Similarly inhibitors may be tested in vivo. Typically, the test compound(s) are administered directly to the tissue being investigated, for example, by injection. After a suitable period of time, cells are harvested from the animal and the stem cell population is analyzed as described above.

If desired, an inhibitor can also be tested, for example an inhibitor of canonical Wnt/ß-catenin signaling. The compound and the inhibitor may be provided to the stem cells concomitantly, or the compound may be provided before or after the inhibitor.

In one embodiment, the ability of the compound(s) to promote stem cell expansion is tested in vivo in murine skeletal muscle tissue. The increase in satellite stem cells isolated from treated mice is monitored and compared to that in control mice, which are either untreated or treated with a placebo, such as buffer or saline solution. In accordance with one embodiment of the invention, a compound is considered to promote stem cell expansion when the satellite stem cell population increases by at least about 10%, e.g. compared to control. Another measure is an increase in the proportion of symmetrical to asymmetrical divisions. The increase in stem cells is measured over a time period of at least 24 hours and more typically over a period of at least 96 hours.

The ability of Wnt7a, analogues, derivatives, variants and active fragments thereof, or other PCP activators or effectors to repair damaged or dysfunctional tissue can be tested in a suitable animal model. Exemplary animal models are described in the Methods section. For example, the ability of the compound(s) and treatments to repair damaged muscle tissue can be tested by administering the compound(s) or treatments to mice exposed to freeze-induced or cardiotoxin induced muscle damage, and monitoring repair of the damaged muscle (see Megeney et al., (1996) Genes Dev., 10:1173-1183; Asakura et al., (2000) J: Cell Biol., 159:123-134).

It has been demonstrated that Fzd7 may be used as a marker for satellite stem cells when used in combination with at least one other stem cell marker. This feature can be used to identify or isolate stem cells for subsequent analysis, treatment, and/or transplantation. It was found that Fzd7 was particularly expressed on quiescent satellite stem cells. Therefore, Fzd7 could also be used as a marker of proliferative state in a stem cell.

It has also been demonstrated that a satellite stem cell may be identified or isolated by selecting for the marker Pax7+ in combination with YFP− or Myf−. In one embodiment, there is provided a method of identifying or isolating satellite stem cells based on the characteristics YFP−/Pax7+. The method can be used to identify and isolate cells for subsequent analysis, treatment, and/or transplantation.

SUMMARY OF EXPERIMENTAL FINDINGS

This section is a summary of the research findings described below in the Examples. The scope of the invention is not in any way limited to the content of this summary or the Examples that follow.

The present inventors previously identified a small population of satellite stem cells and reported that satellite cells represent a heterogeneous population of stem cells and progenitor cells. The satellite stem cells were shown to be capable of self-renewal and long-term reconstitution of the satellite cell niche following transplantation (Kuang et al., 2007).

Figure 4:
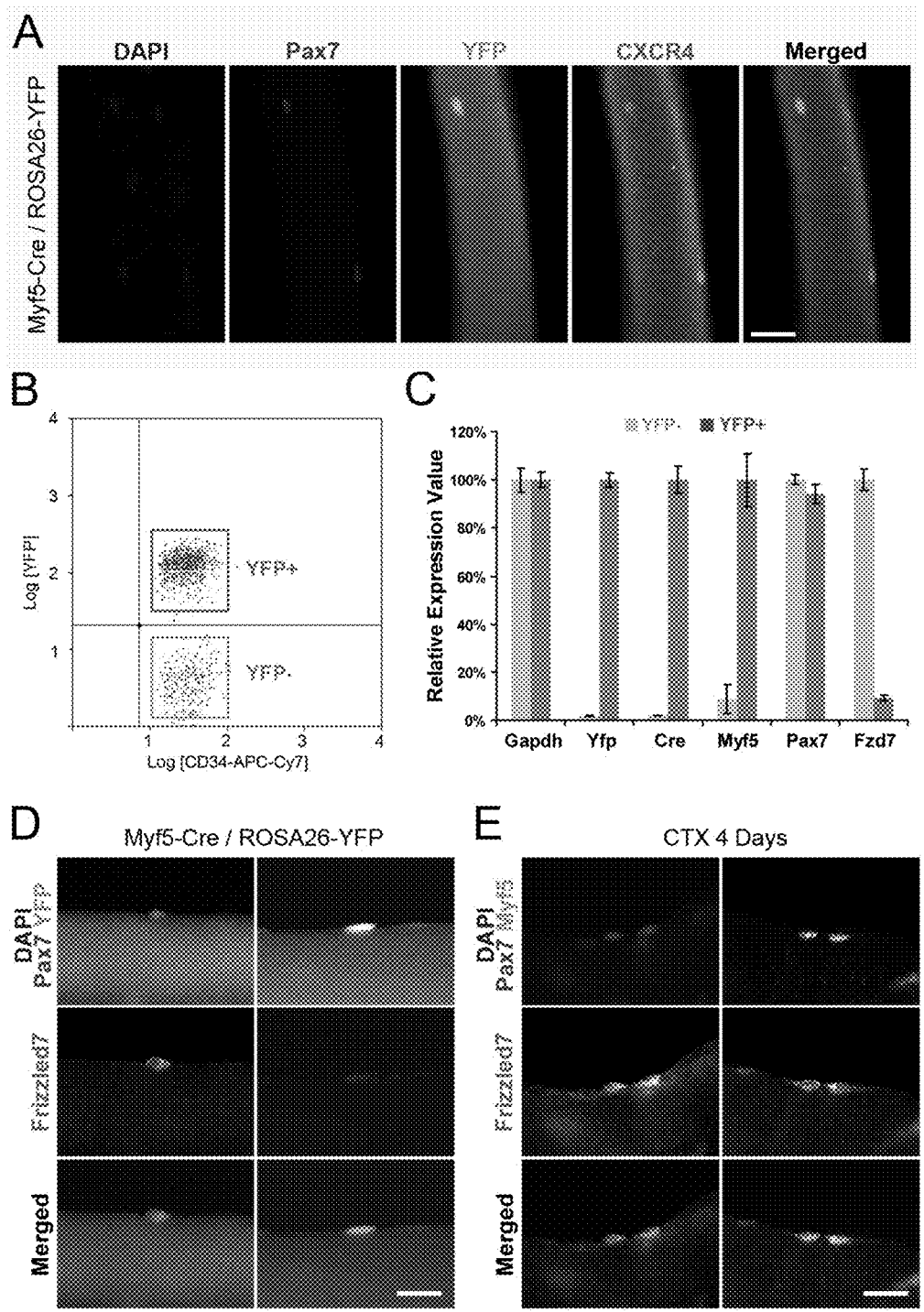
FIG. 4. Satellite Stem Cells Express the Wnt receptor Frizzled7. (A) Single myofibers isolated from Myf5-Cre/ROSA26-YFP mice. 90% of Pax7$^+$ cells expressed YFP, and 10% of Pax7$^+$ cells were YFP$^-$. Satellite cells uniformly expressed the stem cell marker CXCR4. (B) Gated satellite cells ($\alpha 7$-Integrin$^+$, CD34$^+$, CD45$^-$, CD31$^-$, CD11b$^-$, Sca1$^-$) extracted from resting limb skeletal muscle were separated on the basis of Myf5-Cre activated YFP fluorescence. (C) Real-time PCR analysis of sorted cells showing the absence of Myf5 and YFP transcripts as well as the expression of Fzd7 transcripts in YFP$^-$ sorted cells (n=3). (D) Fzd7 was expressed specifically in quiescent Pax7$^+$/YFP$^-$ satellite stem cells (left) but not in Pax7$^+$/YFP$^+$ satellite myogenic cells (right) in freshly isolated Myf5-Cre/ROSA26-YFP myofibers (E) Proliferating satellite cells and myogenic precursor cells express Fzd7. Regenerating EDL myofibers were isolated 4 days after TA muscle injury. Both Pax7$^+$/Myf5$^-$ (left) and Pax7$^+$/Myf5$^+$ (right) dividing satellite cells expressed Fzd7. Bars are 10 µm. Errors bars represent SEM.
Figure 5:
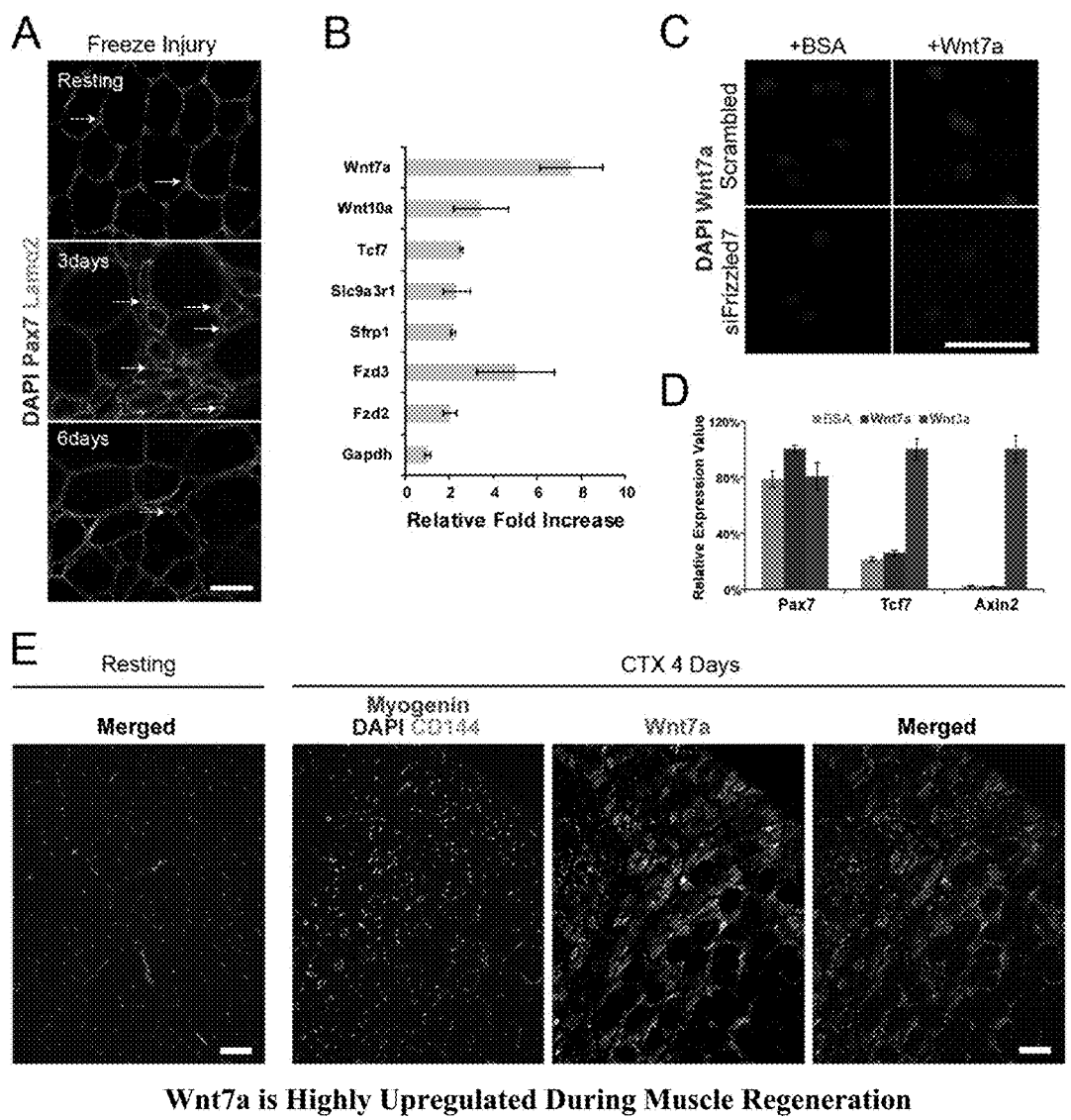
FIG. 5. Wnt7a is Highly Upregulated During Muscle Regeneration. (A) Cryosections of resting (top) and freeze-injured TA muscles analyzed at 3 (middle) and 6 (bottom) days following injury. The basal lamina of myofibers is revealed by Laminin $\alpha 2$ chain staining and satellite cell nuclei were visualized by Pax7 staining. (B) Real-time PCR-array analysis of regenerating TA muscle 6-days following freeze-injury, revealed upregulation of Wnt7a mRNA at the time that satellite cells return to quiescence (n=3). (C) Recombinant Wnt7a protein binds Frizzled7 at the surface of myogenic cells, and this binding is abolished after knock-down of Frizzled7. (D) Wnt3a but not Wnt7a activates $\beta$-catenin/TCF target genes. Real-time PCR analysis of cultured myogenic cells after stimulation with BSA (control), and recombinant Wnt proteins. Only Wnt3a induced the transcription of the $\beta$-catenin/TCF target genes Tcf7 and Axin2 (n=5). (E) Wnt7a protein is expressed by regenerating myofibers, and not by vascular endothelial cells. Cryosections of 4-days cardiotoxin-induced regenerating (left) and resting contralateral (right) TA muscles. Sections were examined for the expression of Myogenin (differentiating myogenic cells), CD144 (endothelial cells) and Wnt7a proteins. Bars are 25 µm. Errors bars represent SEM.
Figure 6:
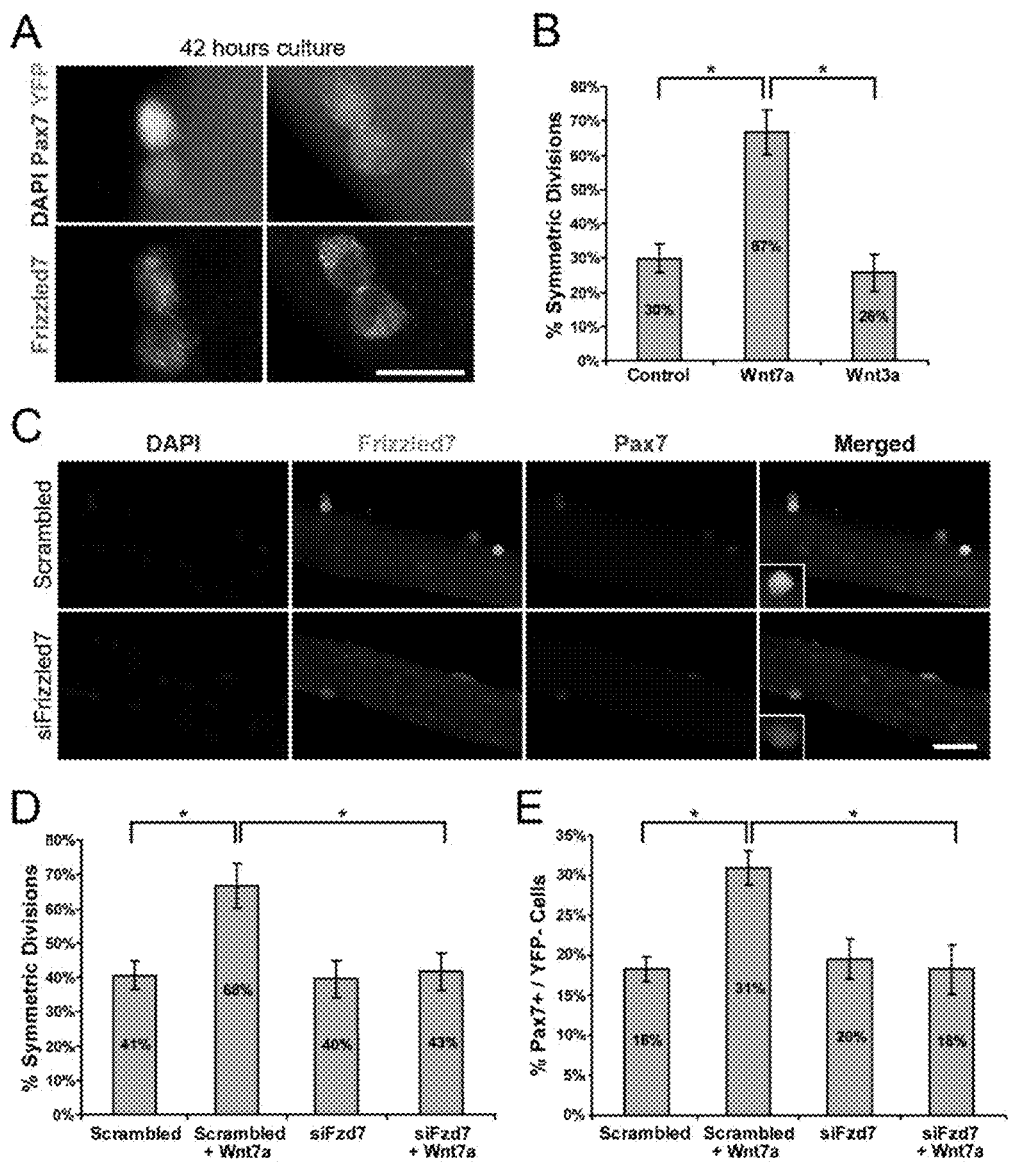
FIG. 6. Wnt7a-Frizzled7 Signaling Drives Satellite Stem Cell Expansion. (A) First division of Pax7$^+$/YFP$^-$ satellite stem cells, 42 hours after isolation of EDL single myofibers from Myf5-Cre/ROSA26-YFP mice, cultured in floating conditions. Satellite stem cells either give rise to one YFP$^-$ stem cell and one YFP$^+$ committed cell, via asymmetric cell division (left), or alternatively give rise to two YFP$^-$ daughter cells by symmetric cell division (right). (B) Wnt7a but not Wnt3a stimulation markedly increased the proportion of symmetric cell divisions resulting in satellite stem cell expansion (n=3, *p=0.009). (C) Activated satellite cells on cultured myofibers at 42 h after isolation, do not express Fzd7 (bottom) after knock-down of Fzd7 with siRNA, as compared to cells in non-silencing conditions (top). (D) The Wnt7a-induced increase in the rate of symmetric satellite stem cell divisions was abrogated following silencing of Fzd7 on myofibers after 42 h of culture (n=3, *p<0.02). (E) The increase in symmetric satellite stem cell numbers induced by Wnt7a was blocked by silencing of Fzd7 on myofibers after 52 h of culture (n=3, *p<0.03). Bars are 10 µm. Errors bars represent SEM.

Through diligent research efforts, the present inventors have now determined that the non-canonical Wnt receptor Fzd7 is specifically expressed in quiescent satellite cells (FIG. 4). Wnt7a was examined as a candidate ligand for Fzd7. We found by Real-time PCR and immunohistochemistry that Wnt7a was markedly upregulated in newly formed myofibers during regenerative myogenesis (FIG. 5B, 5E), and that the Fzd7 receptor is necessary for Wnt7a binding at the surface of myogenic cells (FIG. 5C). Satellite stem cells undergo apical-basal asymmetric cell divisions to give rise to committed myogenic cells that express Myf5, and to maintain their population through self-renewal. Alternatively, satellite stem cells can undergo planar symmetric cell divisions to drive expansion of their population (Kuang et al., 2007). Importantly, the present inventors found that recombinant Wnt7a protein dramatically stimulated the symmetric expansion of satellite stem cells and that this expansion required Fzd7 and Vangl2 (FIGS. 6 and 8), both components of the planar cell polarity (PCP) signaling pathway. Moreover, Wnt7a induced polarized localization of Vangl2 at opposite poles in pairs of dividing cells (FIG. 7), in a manner consistent with Wnt7a activating PCP signaling.

Figure 9:
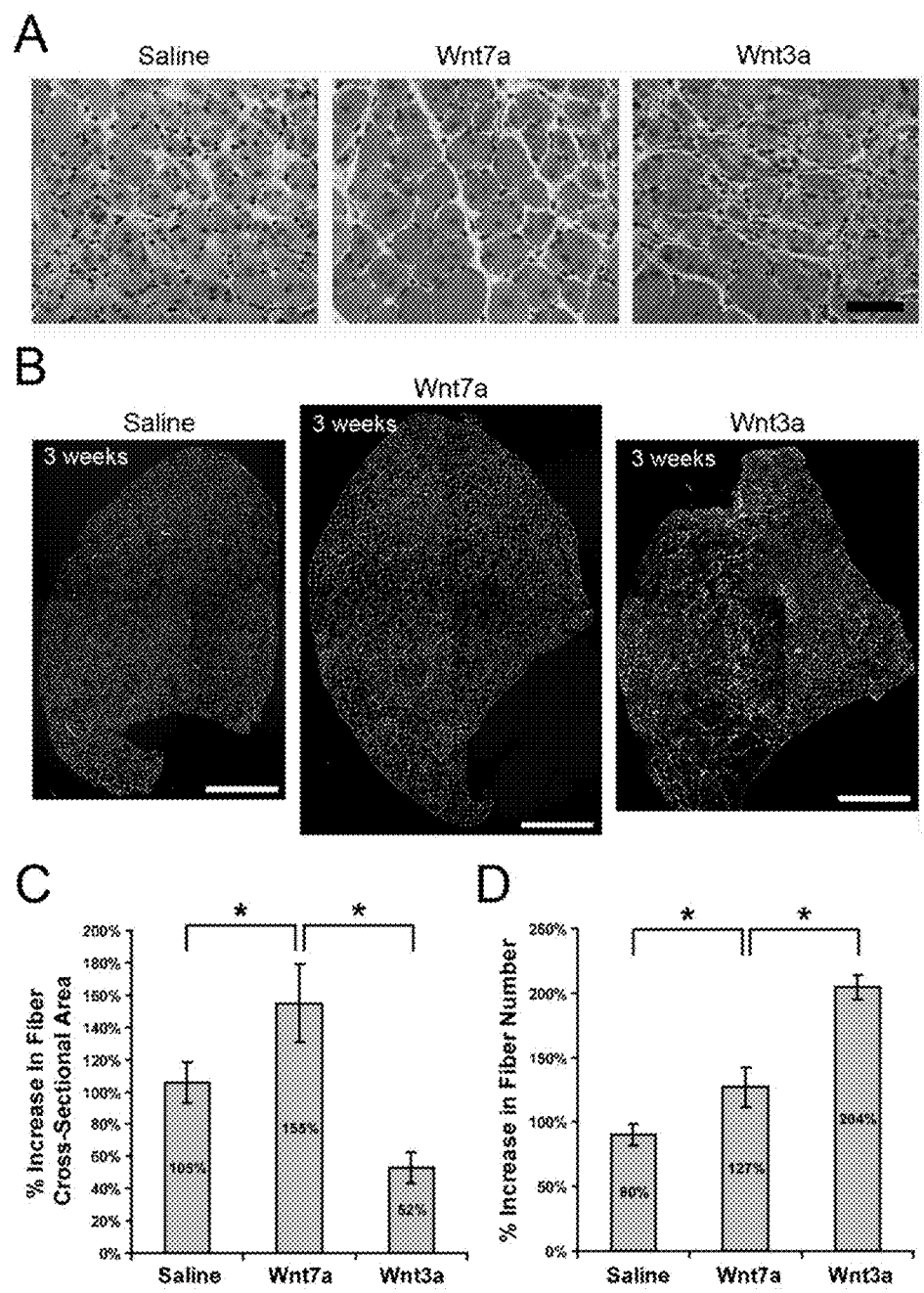
FIG. 9. Ectopic Wnt7a Enhances Muscle Regeneration. (A) Representative histology of regenerated TA muscles of 3-month old mice, 8 days following electrotransfer-induced injury. Regenerated myofibers show centrally-located nuclei. Bar is 25 µm. (B) Representative cryosections of TA muscles 3 weeks following electroporation with CMV-Wnt7a plasmid exhibit accelerated regeneration as evidenced by increased mass, and number and caliber of fibers. Electroporation with CMV-Wnt3a resulted in malformed muscle with abnormal accumulation of matrix. The basal lamina of myofibers was detected by Laminin $\alpha 2$ chain immunostaining. Bars are 200 µm. (C) Quantification of muscle fiber caliber in TA muscles electroporated with either saline or a Wnt7a/Wnt3a expression plasmids, as compared to contralateral leg, 3 weeks after electroporation (n=4, *p<1.008). Wnt7a and Wnt3a have divergent effects on myofiber caliber. (D) Quantification of muscle fiber number in TA muscles electroporated with either saline or a Wnt7a/

Over expression of Wnt7a during muscle regeneration resulted in an impressive enhancement of the regeneration process, generating more fibers of bigger caliber, independent of an effect on myoblast proliferation or differentiation (FIG. 9). Importantly, Wnt7a over-expression resulted in a large expansion of the satellite stem cell population, and Wnt7a loss resulted in impaired maintenance of the satellite cell compartment (FIG. 10). These results provide important new insights into the molecular regulation of satellite cell self-renewal, and for the first time implicate the Wnt non-canonical PCP pathway in the regulation of adult stem cell function.

Figure 7:
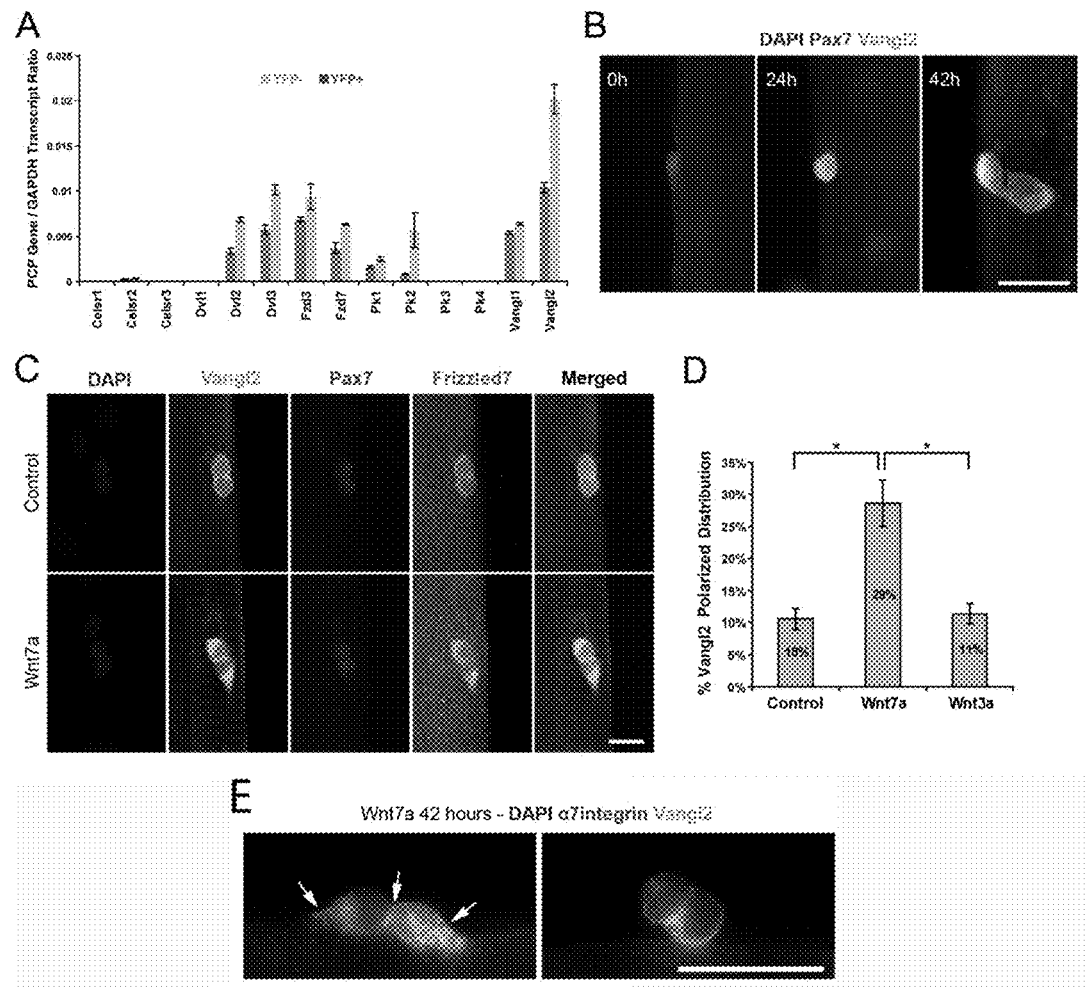
FIG. 7. PCP Components are Expressed by Myogenic Cells. (A) Quantitative real-time PCR analysis indicated expression of PCP core component transcripts by YFP$^+$ and YFP$^-$ satellite cell-derived myoblasts (n=3). (B) Immunostaining indicated that Vangl2 is upregulated during activation of Pax7$^+$ satellite cells by 24 h on cultured myofibers. (C) Wnt7a induces polarized Vangl2 cellular localization on opposite poles of dividing Pax7$^+$ satellite cells on cultured myofibers. EDL myofibers were cultured in control medium or medium supplemented with Wnt7a and fixed 42 hours after isolation. (D) Effects of Wnt treatment on Vangl2 polarization during initial division. Wnt7a signaling, but not Wnt3a, induces polarized localization of Vangl2 and Fzd7 during satellite cell division (n=3, *p=0.006). (E) Wnt7a-treated myofibers were immunolocalized for Vangl2 and the membrane marker $\alpha 7$-Integrin. Vangl2 is polarized and co-localize to the membrane in planar-dividing satellite cells (arrows). Note the polarized and upregulated expression of $\alpha 7$-integrin, which facilitates adhesion to the basal lamina of both daughter cells. Bars are 10 µm. Errors bars represent SEM.
Figure 8:
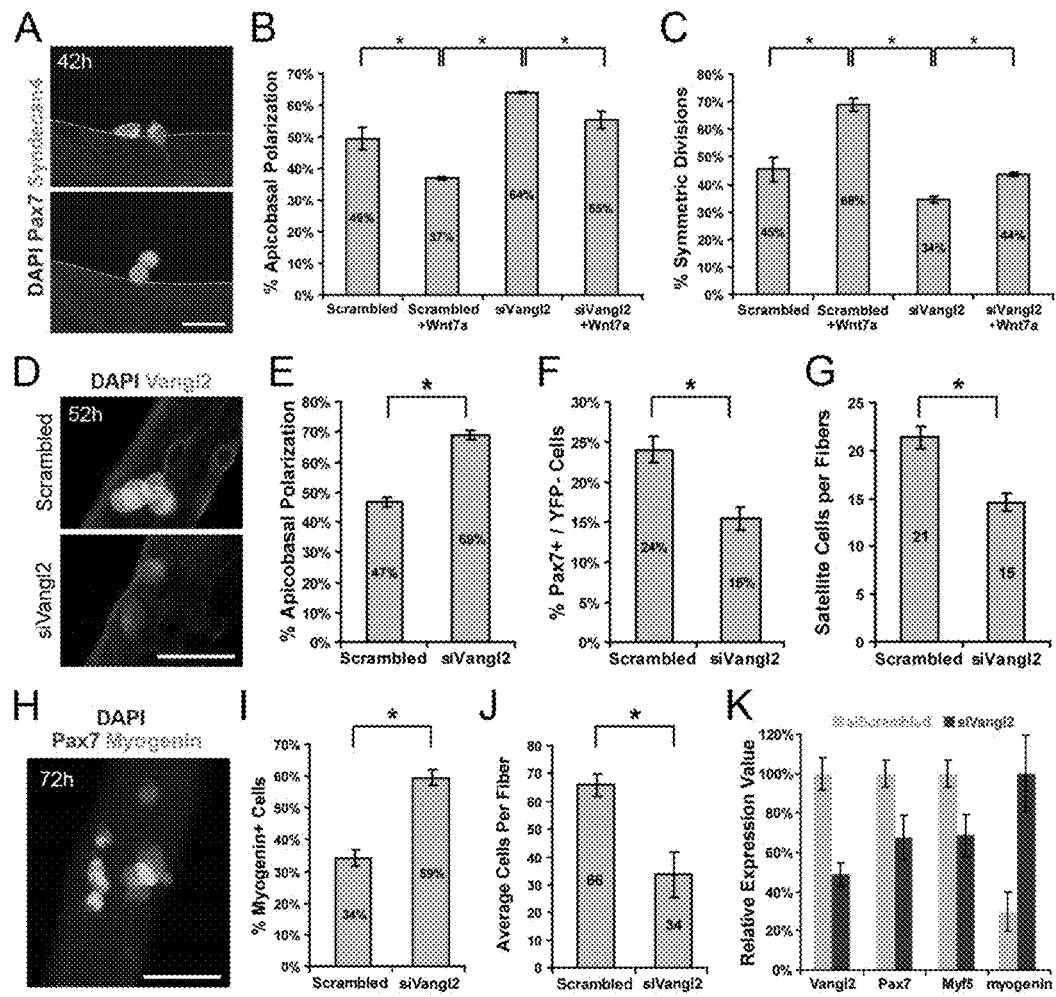
FIG. 8. Vangl2 is Required for Symmetric Expansion of Satellite Stem Cells. EDL single myofibers from Myf5-Cre/ROSA26-YFP mice were cultured in floating conditions and subjected to either non-silencing or Vangl2 siRNA transfection. (A) Orientation of Pax7$^+$/Syndecan4$^+$ satellite cell first cell division at 42 hours. Divisions were scored either as planar (top) or apical-basal (bottom). Note, in myofiber culture, satellite cells translocate to the outside surface of the basal lamina and apical-basal cell divisions are directed into the media. (B) Wnt7a induces a significant decrease in the proportion of apical-basal cell divisions after 42 h of culture supporting its function in stimulating stem cell expansion. Knock down of Vangl2 inhibits the ability of Wnt7a to stimulate planar cell divisions (n=3, *p<0.02). (C) The Wnt7a-induced increase in symmetric satellite stem cell divisions was abrogated following silencing of Vangl2 on myofibers after 42 h of culture (n=3, *p<0.02). (D) Activated satellite cells on myofibers knocked-down for Vangl2 after 52 h of culture do not express Vangl2 (bottom) as compared to cells in non-silencing conditions (top). (E) Knock-down of Vangl2 increased the rate of apical-basal divisions (n=5, *p=0.001). (F) Knock-down of Vangl2 decreased the proportion of Pax7$^+$/YFP$^-$ stem cells (n=3, *p=0.03). (G) Knock-down of Vangl2 decreased the number of cells per fibers (n=5, *p=0.001). (H and I) Silencing of Vangl2 increased the proportion of differentiating Myogenin$^+$/Pax7$^-$ cells myofibers after 3 days of culture (n=4, * p=10$^{-5}$). (J) Silencing of Vangl2 depleted the satellite cells pool (n=4, *p=0.001). (K) Vangl2 silencing promotes myogenic differentiation as revealed by Real-time PCR analysis of gene expression in satellite cell-derived myoblasts (n=4). Bars are 10 µm. Errors bars represent SEM.

The Wnt-PCP pathway plays a role in patterning by instituting polarity of cells within a tissue, such as with the organized orientation of epithelial cells in *Drosophila* (Zallen, 2007). In vertebrates, PCP signaling, and particularly its effecter Vangl2 (also known as Strabismus), is required for the polarization of stereociliary bundles in the cochlea (Montcouquiol et al., 2003), for convergent extension (CE) movements regulating gastrulation and neurulation (Torban et al., 2004), neural tube closure (Torban et al., 2008), and in regulating myocyte orientation in the developing myotome (Gros et al., 2009). During zebrafish neurulation, loss of Vangl2 abrogates polarization of neural keel cells by preventing re-intercalation of daughter cells into the neuroepithelium, resulting in ectopic neural progenitor accumulation (Ciruna et al., 2006). Based on the findings presented herein, it is now proposed that the symmetric expansion of satellite stem cells results from a PCP-mediated orientation of the axis of stem cell division. Since PCP is a positional signaling relying on the redistribution of effector proteins, polarization of PCP core molecules on opposite poles of the daughter cells allows both cells to maintain contact with the basal lamina and thus preserve their orientation relative to the niche (FIG. 7). Notably, Wnt7a induced polarized distribution of Vangl2 and $\alpha$7-integrin (FIG. 7E). The upregulated and polarized localization of $\alpha$7-integrin allows both daughter cells to remain attached to the basal lamina. By contrast, $\alpha$7-integrin expression is reduced and evenly distributed in apical-basal oriented cell divisions. Daughter cells that are "pushed" towards the sarcolemma, thus losing contact with the basal lamina, activate Myf5 transcription and commit to a progenitor state (Kuang et al., 2007). Therefore, these data suggest that the PCP pathway intersects with the mechanisms that control apical-basal cell divisions and commitment and function through a mechanism that promotes adhesion to the basal lamina.

The experiments suggest that polarized distribution of Vangl2 protein at the poles of a couplet of daughter cells allows both cells to remain attached to the basal lamina, and therefore maintain a stem cell state, resulting in expansion of the stem cell population. Subsequent cell divisions will generate larger numbers of committed daughter cells through apical-basal asymmetric divisions that will undergo normal expansion and differentiation (FIG. 9). We previously noted that the proportion of Pax7$^+$/Myf5$^-$ satellite stem cells increased from 10% to about 30% at 3 weeks following injury (Kuang et al., 2007), and we have now demonstrated that overexpression of Wnt7a further increased the level to 50% (FIG. 10C, 10D). By contrast, satellite cell numbers decreased by 36% in Wnt7a-deficient muscle following injury and regeneration (FIG. 10G). These data suggest that Wnt7a regulates the homeostatic maintenance of the satellite stem cell pool by modulating the increase in satellite stem cell expansion during regenerative myogenesis, and that basal levels of PCP signaling are insufficient to maintain the satellite cell pool at normal levels.

Canonical Wnt-signaling plays a well-documented role in regulating myogenic growth and differentiation. The experiments described herein indicate that activation of Wnt/β-catenin signaling using Wnt3a did not interfere with satellite stem cell choice between commitment and symmetric expansion (FIGS. 6B, 6D). Nevertheless, over-expression of Wnt3a in vivo appeared to impair regeneration, likely by promoting premature differentiation and the formation of myofibers of reduced size (FIG. 9). Indeed, Wnt3a stimulation of satellite cells on single myofibers drove their differentiation as evidenced by significant increase in the number of Pax7−/MyoD+ cells (not shown). However, Wnt3a expression was not detected in undamaged or regenerating skeletal muscle by Real-Time PCR. Potentially, other upregulated Wnts, such as Wnt10a (FIG. 5B), may function to activate the Wnt/β-catenin signaling pathway in myogenic cells. Furthermore, a large up-regulation of the Wnt-inhibitors sFRPs was observed during the early stages of the regenerative process. This may represent a physiological feedback system that inhibits canonical Wnt signaling, allowing the proliferation of myogenic progenitors. Thus, it is hypothesized that inhibition of Wnt/β-catenin signaling would act to promote muscle regeneration.

In *Xenopus* embryos, the Vangl2 homolog Strabismus inhibits Wnt/β-catenin activated transcription by competing for Disheveled (Park and Moon, 2002). Thus, without wishing to be bound by theory, PCP signaling may also act to keep satellite stem cells in an uncommitted state by antagonizing canonical Wnt/β-catenin signaling. In *Drosophila* eye development, Frizzled (Fzd)/PCP signaling induces cell-fate specification of the R3/R4 photoreceptors through regulation of Notch activation in R4 (del Alamo and Mlodzik, 2006). This raises the possibility that cross-talk between Frizzled/PCP and Notch pathways, as well as Wnt/β-catenin pathways, act to coordinate satellite stem cell choice between self-renewal/commitment versus expansion. Molecular characterization of satellite stem cells is providing important insights into the molecular mechanisms regulating their function. The present identification of a role for the Wnt7a/Fzd7/Vangl2 signal transduction cascade reveals an unanticipated role for the PCP pathway in regulating the symmetric expansion of satellite stem cells. This finding represents a significant advance in our understanding of satellite cell biology and muscle regeneration. Future experiments will investigate both the utility of modulating the PCP pathway to augment muscle regeneration towards ameliorating the loss of muscle function in neuromuscular disease.

EXAMPLES

Example 1

Frizzled7 is Highly Expressed in Quiescent Satellite Stem Cells

Satellite cells are a heterogeneous population composed of stem cells and committed progenitors. All satellite cells express Pax7 and markers such as CXCR4, however, the present inventors identified a subset of about 10% of Pax7+ cells that have never expressed Myf5 during their developmental history (FIG. 4A). This subset of Pax7+/Myf5− satellite was identified as a stem cell population within the satellite cell niche (Kuang et al., 2007). Towards performing gene expression analysis of quiescent satellite stem cells, the inventors first developed an improved methodology for satellite cell isolation by fluorescence activated cell sorting (FACS), as described in the Methods section. FACS-purified cells (CD34+, α7-Integrin+, CD31−, CD45−, CD11 b−, Scat) (FIG. 11A), were >95% satellite cells as determined by Pax7 and Syndecan4 expression (FIG. 11B), and exhibited robust growth and differentiation potential in vitro (FIG. 11C).

FACS-purified satellite cells were further separated on the basis of Myf5-conditional YFP fluorescence (FIG. 4B). In vitro cultured YFP− satellite cells gave rise to proliferating cells expressing Pax7, but not YFP or Myf5 protein, when maintained at low density (FIG. 12), thus validating that YFP− cells do not and have not expressed Myf5. Real-Time PCR analysis of freshly sorted cells confirmed Pax7 expression (FIG. 4C), as well as several other satellite cell markers such as cMet, Syndecan4, Caveolin1 and α7-Integrin (not shown) in isolated YFP+ and YFP− satellite cells. In addition, YFP and Myf5 transcripts were detected in YFP+ satellite cells while virtually no YFP and Myf5 expression (not significantly different from RT− controls) were detected in YFP− satellite cells (FIG. 4C). Suppressive subtractive hybridization (SSH) of cDNAs (Diatchenko et al., 1997) was employed to identify genes expressed specifically in quiescent Pax7+/Myf5− satellite stem cells. Notably, one of the differentially expressed clones encoded a fragment from within the Frizzled7 (Fzd7) mRNA. Fzd7 is a G-protein-coupled transmembrane Wnt receptor that belongs to a protein family encoded by multiple genes (Egger-Adam and Katanaev, 2008). Real-time PCR analysis confirmed that Fzd7 transcripts were abundantly expressed in YFP− satellite cells and only marginally detected in YFP+ satellite cells (FIG. 4C).

To confirm the differential expression suggested by Real-Time PCR, Fzd7 protein expression was examined in myofibers fixed immediately following isolation from extensor digitorum longus (EDL) muscles. Immunohistological analysis revealed that 12±3% of Pax7+ satellite cells expressed readily detectable levels of Fzd7 (n=3 mice, >150 cells/mouse). Analysis of myofibers isolated from Myf5-Cre/ROSA26-YFP EDL muscles demonstrated that Fzd7 was specifically upregulated in satellite stem cells (Pax7+/Myf5−) that do not contain detectable levels of YFP (FIG. 4D). However, culture of fibers in suspension for 2 days resulted in upregulation of Fzd7 in virtually all satellite cells (99%, n=3 mice, ≥100 cells per mouse). Furthermore, examination of regenerating myofibers from EDL muscle following cardiotoxin (CTX) induced damage of the tibialis anterior (TA) muscle (Kuang et al., 2007), revealed Fzd7 expression on doublets of Pax7+/Myf5− and Pax7+/Myf5+ cells (FIG. 4E).

Taken together, these results demonstrate that, in resting muscle, the Wnt receptor Fzd7 is specifically expressed in quiescent satellite stem cells. However, Fzd7 is also upregulated in proliferating satellite cells and myoblasts. Thus, the Fzd7 receptor may be considered a marker of quiescent satellite stem cells in resting muscle, and may be particularly useful as a marker of quiescent satellite stem cells in combination with other stem cells markers. The Fzd7 receptor may also be used as a target for purification of quiescent satellite stem cells, for instance, employing antibodies reactive to Fzd7.

Example 2

Wnt Expression During Muscle Regeneration

The present inventors hypothesized that Wnt7a was a candidate ligand for Fzd7 receptor. Coexpression of Fzd7 and Wnt7a during embryonic myogenesis had been reported (Cossu and Borello, 1999) and Wnt7a had been implicated as a regulator of embryonic and adult myogenesis (Chen et al., 2005; Polesskaya et al., 2003; Tajbakhsh et al., 1998). Real-Time PCR-Array analysis of freeze-injured TA muscle was employed to document Wnt expression during regenerative myogenesis. Freeze injury of muscle was chosen because of the significantly reduced inflammatory response relative to other methods such as cardiotoxin (CTX) injection. Changes in gene expression were analyzed at 3 days post-injury, during the acute phase of regeneration, where most of the Pax7+ cells are proliferating, and at 6 days post-injury, when satellite cells have returned to a quiescent sub-laminar position (FIG. 5A).

At 3 days post-injury significant increases (as compared to contralateral leg, n=3 mice, p<0.05) in 31 transcripts were detected, including those for multiple Wnts (Wnt-1, -2, -5b, -8b, -10a, -16a), Frizzled receptors and sFRP inhibitors. Notably, at 6 days post-injury a significant increase (n=3 mice, p<0.05) was detected in the transcript levels for Wnt7a and Wnt10a, (FIG. 5B). Wnt3a levels were below the limit of detection in the analyses at both 3 and 6 days of regeneration. Therefore, Wnt7a mRNA was markedly upregulated at the time when satellite stem cells replenish the resident satellite cell pool.

To confirm Wnt7a up-regulation during muscle regeneration in another muscle injury model, immunohistochemical analysis of Wnt7a protein expression was performed on cryosections of CTX-injured TA (fixed 4 days post-injury) and the contralateral resting TA. In undamaged muscle, Wnt7a was not expressed at detectable levels (FIG. 5E, left). By contrast, Wnt7a was strongly upregulated in regenerating fibers (of smaller size than the intact fibers and containing Myogenin+ nuclei), and was not expressed by CD144+ endothelial cells (FIG. 5E, right).

Figure 1:
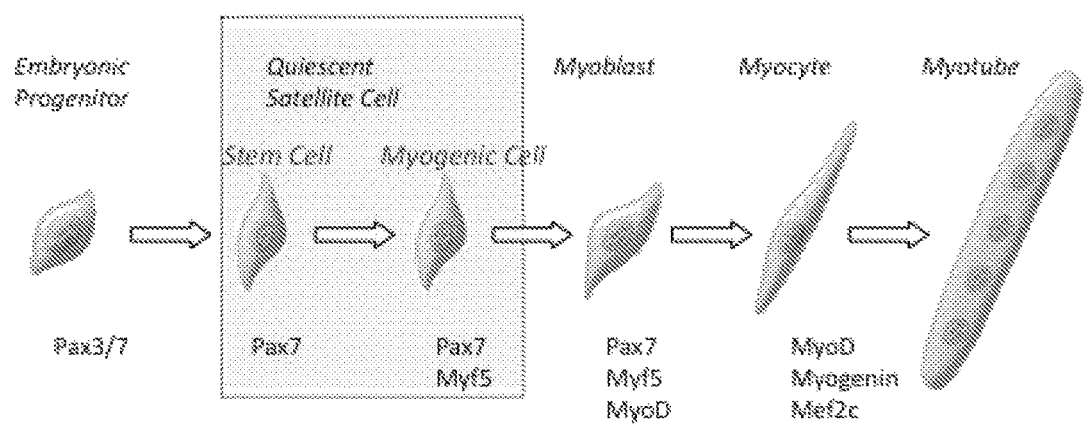
FIG. 1: Developmental program of satellite cells in skeletal muscle. Progenitors of satellite stem cells originate in the somite as Pax3 and/or Pax7 expressing progenitors. Satellite stem cells express Pax7 whereas satellite myogenic cells have additionally activated Myf5 transcriptional competence as revealed by expression of Myf5-lacZ and Myf5-cre knock in alleles. Following activation and entrance into the cell cycle, myogenic precursor cells express Myf5 and MyoD. Induction of Myogenin and Mef2c together with downregulation of Myf5 then MyoD mark withdrawal from the cell cycle and entrance into the terminal differentiation program.
Figure 2:
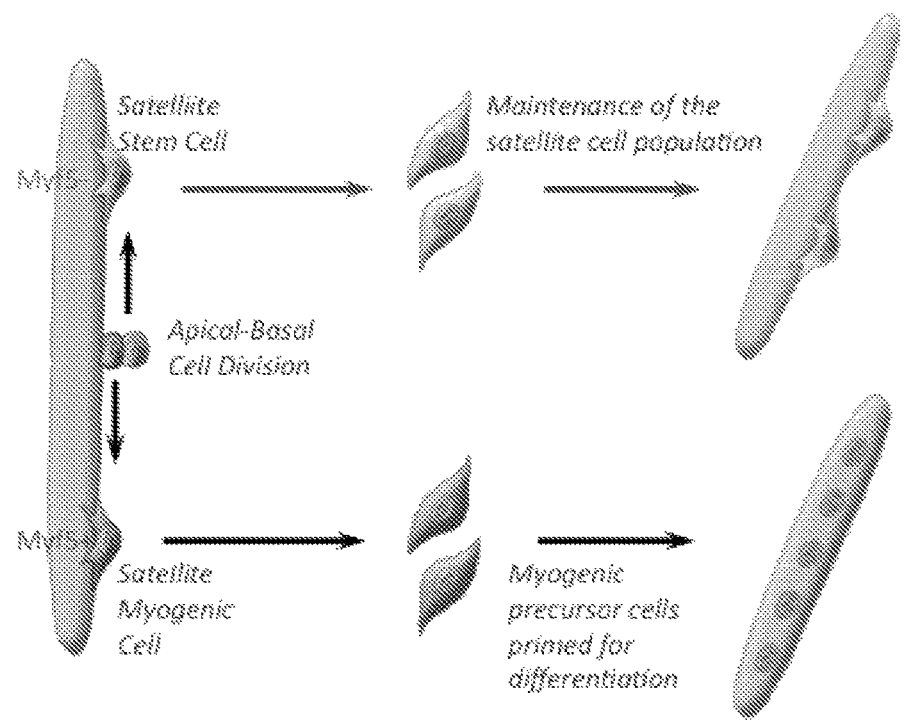
FIG. 2: The satellite cell population is heterogeneous composed of satellite stem cells and satellite myogenic cells. Using Myf5-Cre and ROSA26-YFP Ore alleles, the present inventors found that, in vivo, about 10% of sub-laminar Pax7-expressing satellite cells have never expressed Myf5. Moreover, they found that Pax7$^+$/Myf5$^-$ satellite cells gave rise to Pax7/Myf5$^+$ satellite cells through apical-basal oriented divisions that asymmetrically generated a basal Pax7$^+$/Myf5$^-$ and an apical Pax7$^-$/Myf5$^+$ cells. Prospective isolation and transplantation into muscle revealed that whereas Pax7$^-$/Myf5$^+$ cells exhibited precocious differentiation, Pax7$^+$/Myf5$^-$ cells extensively contributed to the satellite cell reservoir throughout the injected muscle. Therefore, satellite cells are a heterogeneous population composed of stem cells and committed progenitors.
Figure 3:
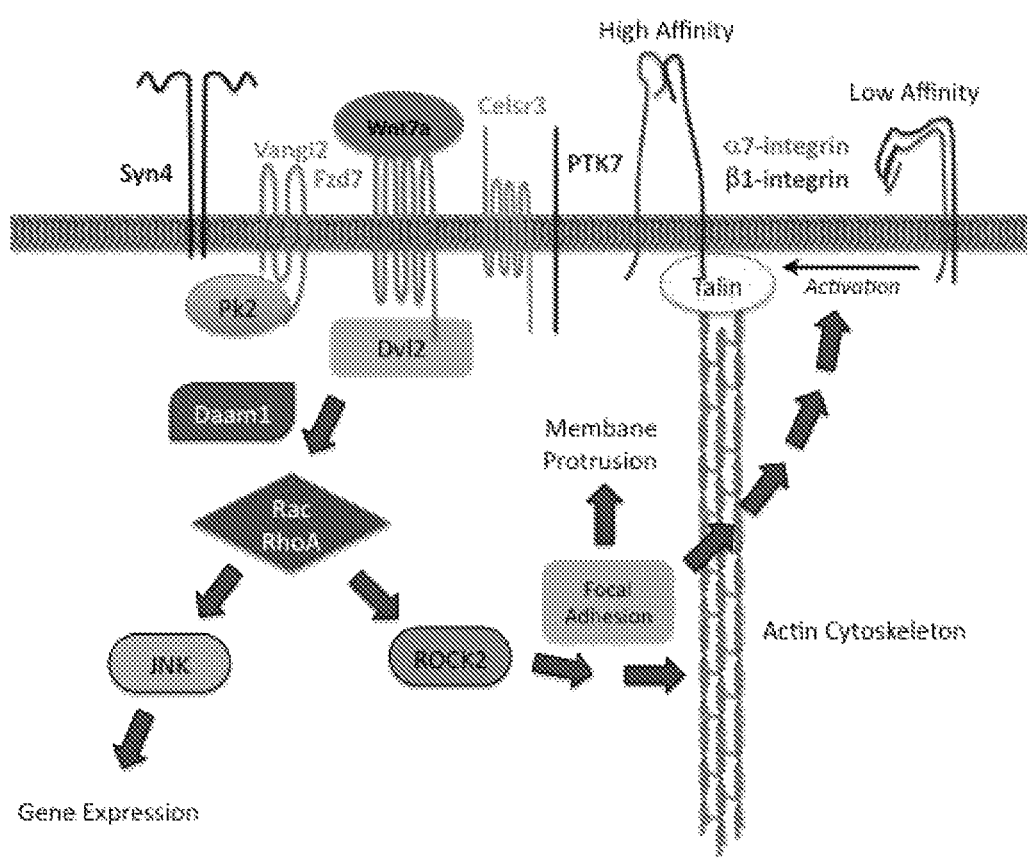
FIG. 3. Symmetric expansion of satellite stem cells results from a PCP-mediated orientation of the axis of stem cell division. Wnt7a through binding of its receptor Fzd7 induced a polarized distribution of Vangl2 and its coreceptor Syn4 through activation of Rac/RhoA. This signaling leads to activation of the α7/β1-integrin receptor together with its concommittent polarization as a consequence of PCP signaling through Fzd7 and Vangl2. The resulting upregulated and polarized localization of α7/β1-integrin allows both daughter cells to remain attached to the basal lamina.

To determine whether Wnt7a is a ligand for Fzd7, cultured satellite cell-derived myoblasts were incubated with recombinant human Wnt7a protein for 30 minutes, washed, fixed and immunostained with anti-Wnt7a antibody. Cells incubated with BSA did not show membrane staining for Wnt7a protein. By contrast, cells incubated with Wnt7a protein exhibited immunostaining on the membrane (FIG. 5C). Importantly, transfection of Fzd7 siRNA abrogated binding of Wnt7a (FIG. 2C). Fzd7 silencing was effective, specific and did not significantly alter the other Frizzled transcripts expressed in myoblasts (FIG. 14A). Taken together, these data indicate that Fzd7 is the receptor for Wnt7a in myogenic cells.

Wnt7a has been described as either a canonical (Hirabayashi et al., 2004) or non canonical Wnt (Kengaku et al., 1998), depending on cell-type and receptor context. To evaluate the possible function of Wnt7a as a canonical Wnt, satellite cell-derived myoblasts were stimulated with Wnt7a and Wnt3a proteins for 24 hours. Wnt3a activates the canonical Wnt pathway in myogenic cells (Brack et al., 2008), and in the present experiment, Wnt3a stimulation resulted in increased expression of β-catenin/TCF target genes, for example a 5-fold and 50-fold increase of Tcf7 and Axin2 mRNAs respectively, (n=5, p≤1.001). By contrast, Wnt7a stimulation did not result in any significant change in Tcf7 and Axin2 levels which were similar to BSA-treated samples (FIG. 5D). In addition, Wnt3a but not Wnt7a stimulation robustly induced the stabilization and nuclear localization of activated-β-catenin (FIG. 13), and Wnt3a but not Wnt7a robustly activated the β-catenin luciferase reporter TOP-Flash in transient transfection experiments (not shown).

Taken together, these results indicate that Wnt7a is markedly upregulated by newly formed myofibers during regenerative myogenesis, binds to the Fzd7 receptor at the surface of myogenic cells, and does not utilize the canonical Wnt/8-catenin signaling pathway.

Example 3

Symmetry of Satellite Stem Cell Divisions is Regulated by Wnt7a-Frizzled7

The expression of Fzd7 in quiescent satellite stem cells and the marked upregulation in Wnt7a during muscle regeneration suggested that Wnt7a-Fzd7 signaling is involved in regulating muscle stem cell function. In addition, Wnt7a had no effect on the growth or differentiation of cultured primary myoblasts in vitro (FIG. 16). Therefore, to investigate the role of Wnt7a-Fzd7 signaling in satellite cells, the ability of recombinant Wnt7a to alter the ratio between asymmetric and symmetric cell divisions of satellite stem cells was examined in vitro. Myofibers were isolated from Myf5-Cre/ROSA26-YFP EDL muscle and cultured under non-adherent conditions. In the culture system, quiescent satellite cells become activated immediately following myofiber isolation. Satellite cells leave their niche, migrate across the basal lamina, and undergo their first cell division in a synchronous fashion. Thus, the outcome of the first division was visualized by fixing and staining the myofibers after 42 hours of culture. Importantly, live imaging analysis confirms that satellite cells do not move on myofibers before dividing and that scored cell doublets are of clonal origin (Kuang et al., 2007).

Satellite stem cells (YFP−) either underwent a symmetrical cell division to give rise to two YFP− daughter cells, or an asymmetric cell division to give rise to one YFP− stem cell and one YFP+ committed precursor (FIG. 6A). When stimulated with Wnt7a, a dramatic increase in the proportion of symmetric cell divisions from 30% to 67% was observed (n=3, n≥152 pairs, p=0.009). By contrast, Wnt3a treatment did not induce any significant change (FIG. 6B). Therefore, Wnt7a stimulated an increase in symmetric satellite stem cell divisions.

The experimental analysis suggested that Wnt7a specifically binds the Fzd7 receptor (FIG. 5C, 5D). Therefore, to determine whether the induction of symmetric stem cell divisions by Wnt7a required the presence of Fzd7, Fzd7 knock-down experiments were performed on isolated myofibers. Immunostaining of treated fibers demonstrated extensive silencing of Fzd7 expression after 42 hours (FIG. 5C). Importantly, siRNA-induced knock-down of Fzd7 resulted in a complete abrogation of the ability of Wnt7a to induce symmetric satellite stem cell divisions (n=3, ≥123 pairs, p≤1.02). By contrast, scrambled siRNA treatment did not significantly affect this activity of Wnt7a (FIG. 6D). Consistent with these results, the proportion of satellite stem cells (Pax7+/YFP−) after the second division (50 hours) was significantly increased by 13% after Wnt7a treatment (n=3, ≥1203 cells, p≤1.03) this resulting in an increase in the number of stem cells per fibers (FIGS. 6E, 14B). Similarly, Fzd7 silencing efficiently blocked the effect of Wnt7a stimulation. The total number of Pax7+ cells per fiber remained constant between each condition, confirming that Wnt7a does not effect cell proliferation or differentiation (FIG. 14C).

These results demonstrate that Wnt7a signals via Fzd7 to stimulate symmetric satellite stem cell division and thus drive the expansion of the satellite stem cell pool.

Example 4

Role for the PCP Component Vangl2 in Satellite Stem Cell Self-Renewal

The analysis indicated that Wnt7a does not activate the canonical Wnt/β-catenin signaling pathway (FIG. 5D), and that Wnt7a signals through the Fzd7 receptor to drive satellite stem cell symmetric divisions (FIGS. 5C, 6B, 6D). Therefore, it was hypothesized that Wnt7a acts through Fzd7 to activate the PCP pathway and drive satellite stem cell expansion. To investigate if Wnt7a activates the PCP pathway, the relative transcript levels of a set of core PCP components (Seifert and Mlodzik, 2007) were analyzed in myogenic cells. Interestingly, myoblasts expressed significant levels of Dvl-2 and -3, Fzd-3 and -7, Pk-1 and -2 and yang/4 and -2, and low levels of Celsr2. Other PCP component genes tested were called absent with cut-off values over 30 cycles (FIG. 4A). In addition, cultured satellite stem cells (YFP⁻) expressed significantly higher levels of all PCP components (n=3, p<0.05), with a marked upregulation of Vangl2, consistent with a role for PCP signaling in regulating satellite stem cell function.

Vangl2 is a crucial regulator of PCP and non-canonical Wnt-signaling in *Drosophila* and vertebrates (Torban et al., 2004). In cells with active PCP signaling, Vangl2 protein is distributed at the poles at either end of the axis of polarization and this distribution is lost in PCP mutants (Montcouquiol et al., 2006). Vangl2 protein was not detected in quiescent satellite cells on isolated myofibers, but was upregulated in activated satellite cells as they entered the cell cycle by 24 hours in culture. After 48 h, all Pax7⁺ activated satellite cells were also positive for Vangl2 (100%, n=3 mice, ≥100 cells per mouse) (FIG. 7B). The expression in satellite cells of Prickle1 and Celsr2 proteins that interact with Vangl2 in vivo was also confirmed (not shown).

Importantly, in the presence of Wnt7a, a significant proportion of dividing doublets of satellite cells on cultured myofibers (29±4%, n=3, ≥240 pairs, p<1.006) exhibited polarized localization of Vangl2 on opposite poles of the daughter cells (FIG. 7C, 7D). By contrast, following BSA (control) or Wnt3a-treatment, Vangl2 protein was uniformly dispersed in satellite cell doublets (90±2% and 89±2% respectively) (FIG. 7C, 7D). Moreover, double staining with anti-Vangl2 and anti-☐α7-integrin antibodies revealed that Wnt7a appeared to induce enhanced membrane localization of Vangl2 and polarized distribution of α7-integrin. This redistribution did not occur in untreated cells or in cells undergoing apical-basal cell divisions (FIG. 7E). Taken together, these observations strongly support the assertion that Wnt7a induces a redistribution of the polarity effector Vangl2 and α7-integrin and the upregulated expression of α7-integrin at the poles of daughter cells allows them to remain adherent with the basal lamina and to remain in the stem cell niche.

To investigate the role of Vangl2 in satellite stem cell function, siRNA silencing of Vangl2 was performed on single Myf5-Cre/ROSA26-YFP myofibers stimulated with Wnt7a. Myofibers were first stained with Pax7 and Syndecan4 antibodies to allow visualization of the plane of satellite cell division relative to the fiber, and cell divisions scored as either planar or apical-basal (FIG. 8A). At 42 h after the first cell division, Wnt7a stimulation induced planar divisions and accordingly resulted in a 12% decrease in apical-basal cell divisions. By contrast, Vangl2 silencing increased the proportion of apical-basal cell divisions by 15%, (n=3, ≥154 pairs, p≤1.02) (FIG. 8B). Myofibers from the same experiments were also stained with Pax7 and YFP antibodies, and the percentage of symmetric cell divisions scored. A close inverse correlation between the proportions of apical-basal versus symmetric cell divisions was observed. Wnt7a stimulation increased the proportion of symmetric cell divisions, whereas Vangl2 knock-down markedly impaired the ability of Wnt7a to stimulate symmetric cell divisions (n=3, ≥65 pairs, p≤1.02) (FIG. 8C).

To analyze the role of Vangl2 in regulating symmetric satellite cell cell divisions, fibers were cultured for 50 hours and assessed Vangl2 silencing by immunostaining (FIG. 8D). At this point, Vangl2 knock-down continued to increase the rate of apical-basal cell divisions (n=5, ≥150 pairs, p=0.001) (FIG. 8E), while depleting the population of satellite stem cells (n=3, ≥330 cells, p=0.03) (FIG. 8F). This resulted in a marked diminution in the total number of satellite cells per fibers (n=5, ≥500 cells, p=0.001) (FIG. 8G). At 3-days after knock-down of Vangl2 (FIG. 8H), a doubling in the number of cells expressing myogenin, an early marker for differentiation, was observed (n=4, ≥550 cells, p=10⁻⁵) (FIG. 8I) along with a loss of half the cells on fibers (n=4, ≥550 cells, p=0.001) (FIG. 8J). Vangl2 silencing on satellite cell-derived myoblasts resulted in reduced levels of Pax7 and Myf5 transcripts, along with increased levels of Myogenin (n=4, p≤1.05) (FIG. 8K). Together, these data suggest that Vangl2 is required for self-renewal of both satellite stem cells and the generation of transient-amplifying myoblasts.

These data demonstrate that Wnt7a signaling through Fzd7 requires Vangl2 to induce symmetric expansion of the satellite stem cell pool. Wnt7a also induces polarized distribution of Vangl2 protein at the opposite poles of cells undergoing a symmetric planar cell division. Hence, Wnt7a utilizes the planar cell polarity pathway to control the orientation of satellite cell division and their fate within the niche.

Example 5

Wnt7a Enhances Muscle Regeneration by Expanding the Stem Cell Pool

To investigate the role of the Wnt7a-Fzd7-Vangl2 pathway in muscle regeneration in vivo, Wnt7a was over-expressed by electroporation of a CMV-Wnt7a expression plasmid into TA muscles of 3-month old mice. Histological analysis of muscles electroporated with CMV-LacZ plasmid revealed that majority (>80%) of the myofibers expressed the β-galactosidase (FIG. 15A) and no regeneration deficit was detected following electroporation of control plasmid (FIG. 15B). In addition, immunostaining revealed that myofibers electroporated with CMV-Wnt7a plasmid secreted readily detectable levels of Wnt7a protein (FIG. 15C).

Notably, TA muscles electroporated with CMV-Wnt7a exhibited an 18±4% (p=0.009, n=8) increase in mass after 3 weeks. Examination of serial sections of electroporated muscles revealed an increase in the overall size of the muscle as well as a significant increase in caliber size and numbers of fibers throughout the body of the muscle (FIG. 9). By contrast, over-expression of Wnt3a resulted in a larger increase in the number of myofibers but these exhibited a dramatic reduction in cross-sectional area, resulting in reduced regeneration efficiency (FIG. 9). No effect of Wnt7a over-expression on other cell types in muscle tissue was observed. However, overexpression of Wnt3a resulted in abnormal matrix deposition suggesting an enhancement of proliferation of fibroblastic/smooth muscle progenitors resulting in increased fibrosis (FIG. 9B). Taken together, these results indicate that over-expression of Wnt7a markedly enhances muscle regeneration, as evidenced by the presence of increased numbers of larger fibers and the significantly increased mass of muscle.

As previously noted, Wnt7a treatment did not alter the growth or differentiation of activated satellite cells or primary myoblasts in vitro (FIG. 14C, 16A, 16C, 16D). In addition, Wnt7a did not induce the expression of MyoD or of Wnt/β-catenin target genes in differentiated myocytes (FIG. 16B, 16E). However, the in vitro experiments established that Wnt7a-Fzd7-Vangl2 signaling stimulated the symmetrical expansion of satellite stem cells, which would then give rise to transient amplifying progenitors that undergo normal proliferation and differentiation. Thus, promotion of symmetric stem cell expansion with normal rates of proliferation and differentiation of progenitor cells showed improved tissue regeneration when compared to stimulated proliferation and differentiation. This is a remarkable finding and also mitigates concern of stem cell depletion.

To assess whether Wnt7a similarly stimulates the expansion of satellite stem cells in vivo, the numbers of satellite cells and satellite stem cells in regenerated muscle were assessed following electroporation of CMV-Wnt7a. Overexpression of Wnt7a resulted in about a 2-fold increase in the number of Pax7$^+$ satellite cells per myofiber on sections at 3 weeks after electroporation (p=0.03, n=4). By contrast, over-expression of Wnt3a did not alter the number of satellite cells (FIG. 10A, 10B). To enumerate the proportion of satellite stem cells, FACS-isolated satellite cells were isolated from Myf5-Cre/ROSA26-YFP TA muscle at 3 weeks following electroporation, cultured for 24 hours, then immunostained for Pax7 and YFP (FIG. 10C). Consistent with the observations that Wnt7a induces symmetrical satellite stem cell divisions in vitro, it was observed that overexpression of Wnt7a in regenerating muscle resulted in about a 20% increase (n=5, p=0.0001) in the proportion of Pax7$^+$/YFP$^-$ satellite stem cells (FIG. 10C, 10D). Therefore, these data indicate that similarly Wnt7a acts on the satellite stem cell compartment in vitro and in vivo.

To investigate satellite stem cell function in the absence of Wnt7a, the regeneration phenotype of 3 mo-old Wnt7a$^{-/-}$ null mice (Miller and Sassoon, 1998) was examined. Quantification of Pax7-expressing satellite cells on freshly isolated myofibers from EDL muscle demonstrated that Wnt7a$^{-/-}$ null mice exhibit about an 18% decrease in number of satellite cells per fiber (p=0.03, n=4) (FIG. 10E). Three-weeks following a freeze-crush injury, the regenerated Wnt7a$^{-/-}$ TA muscles appeared grossly normal (FIG. 10F), however upon closer examination, the fibers appeared to display a less uniform distribution of calibers, and the basal lamina were of irregular thickness, consistent with a defect in regeneration. Importantly, examination of sections of regenerated Wnt7a$^{-/-}$ TA muscles revealed a significant 36% decrease in the numbers of satellite cells (p=0.03, n=3) (FIG. 10G). This result strongly supports the notion that Wnt7a plays an important role in regulating satellite stem cell function.

Overexpression of Wnt7a in muscle drives expansion of the satellite stem cell pool, and conversely, the satellite cell compartment becomes depleted in the absence of Wnt7a. Together, these data demonstrate a novel role for Wnt7a signaling via the PCP pathway to stimulate satellite stem cell symmetrical cell division to drive expansion. Therefore, Wnt7a regulates the homeostatic levels of the satellite stem cell compartment and thus regulates the efficiency of regenerative myogenesis in adult skeletal muscle.

Example 6

Electroporation of Wnt7a Expression Vector in Mdx Mice Results in Enhanced Number of Satellite Cells and Increased Fiber Diameter Mdx mice are a well known mouse model for Duchenne muscular dystrophy. The mdx mice harbor a mutation in exon 23 of the dystrophin gene resulting in the generation of a stop codon. The mutation in the dystrophin gene leads to a disruption of the DGC complex (dystrophin-glycoprotein complex) which is crucial for the integrity of muscle fibers.

Referring to FIG. 17, Electroporation of Wnt7a cDNA into the TA muscle of adult wt mice leads to an increase in satellite cell numbers as well as in the number of satellite stem cells (myf5 negative, Pax7 positive). As can be seen from the figure, the number of satellite stem cells in the Wnt7a group was nearly doubled.

Referring to FIG. 18, the TA muscle of mdx mice was electroporated after injection of a control (lacZ) plasmid or a plasmid containing the coding region of Wnt7a under control of the CMV promoter. The total number of satellite cells (all Pax7 positive cells) as well as satellite stem cells (myf5 negative satellite cells) was counted. The total number of satellite cells was significantly increased in mdx mice electroporated with a Wnt7a containing plasmid (p=0.005). Electroporation of a plasmid containing the coding region of Wnt7a lead to a significant increase in the total number of satellite cells while the proportion of satellite stem cells to committed progenitor cells showed a tendency that more satellite stem cells were present in mdx mice electroporated with Wnt7a plasmid.

Referring to FIG. 19, mdx mice as well as age-matched wt mice (3 month old, male) were electroporated with either the Wnt7a containing plasmid or the lacZ control plasmid. Electroporation of Wnt7a cDNA lead to a significant increase in fiber diameter in mdx and wt mice (p<0.001).

In summary, electroporation of Wnt7a cDNA into the TA muscle of wt as well as mdx mice increased the number of satellite cells. Also the fiber diameter was increased in wt and mdx mice. These findings suggest that Wnt7a could be a possible treatment for Duchenne muscular dystrophy by increasing the number of satellite cells and thereby preventing an exhaustion of the satellite cell pool. The application of Wnt7a could also be used to increase healing of skeletal muscle after injury or surgery.

Example 7

Figure 20:
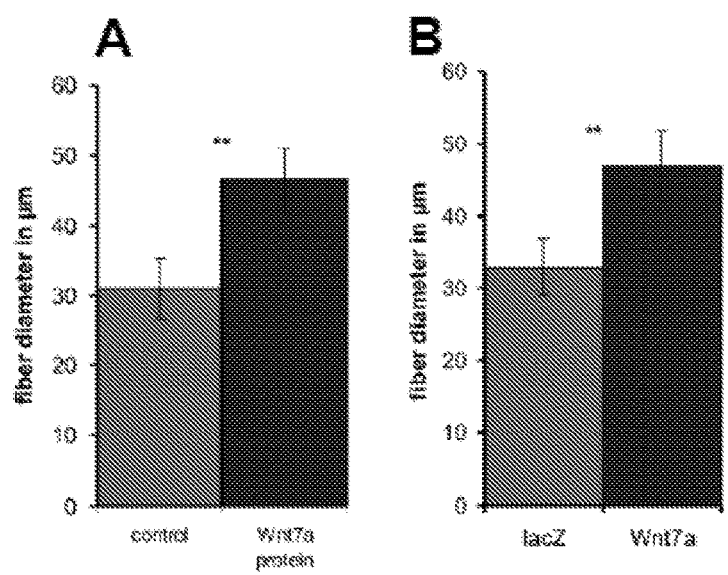

Administration of Wnt7a Recombinant Protein Produces Effects Similar to Electroporation of a Wnt7a Expression Vector Referring to FIG. 20, (A) human Wnt7a protein was injected into the TA muscle and was found to significantly enhance muscle fibre size two weeks after injection (p<0.001) (A). The observed effects were similar to those produced by electroporation of CMV-driven mouse Wnt7a (B).

EXPERIMENTAL PROCEDURES

Mice and Animal Care

Adult (8-12 weeks of age) Myf5-Cre/ROSA26-YFP mice were obtained by crossing the knock-in Myf5-Cre (Tallquist et al., 2000) heterozygous mice with ROSA26-YFP (Srinivas et al., 2001) homozygous reporter mice. ROSA26-YFP mice were used as wild type controls. Wnt7a-null mice and their littermates controls were obtained by crossing heterozygous Wnt7a$^{+/-}$ mice. All mice were maintained inside a barrier facility and experiments were performed following the University of Ottawa regulations for animal care and handling.

Cell Sorting

Mononucleated muscle derived cells were isolated from hind-limb muscles and staining was performed as previously described (Ishibashi et al., 2005; Kuang et al., 2007). Cells were separated on a MoFlo cytometer (DakoCytomation), equipped with 3 lasers. Dead cells and debris were excluded by Hoescht staining, and by gating on forward and side scatters profiles (FIG. 11).

Myofiber Isolation, Culture and Immunohistochemistry

Single myofibers were isolated from the EDL muscles as previously described (Charge et al., 2002). Isolated myofibers were cultured in suspension in 6-well plates coated with horse serum to prevent fiber attachment (Kuang et al., 2006). Fibers were incubated in plating medium consisting of 15% FBS (Hyclone) and 1% chick embryo extract (CEE, Accurate Chemicals) in DMEM containing 2% L-glutamine, 4.5% Glucose and 110 mg/ml Sodium Pyruvate. For myoblast culture, satellite cells were sorted and plated on collagen-coated dishes in Ham's F10 medium supplemented with 20% FBS and 5 ng/ml of basic FGF (Invitrogen). For Wnt stimulation, recombinant Wnt7a or Wnt3a proteins were added in the plating medium (25 ng/ml, R&D Systems). For in vivo activation of satellite cells, regeneration was induced by CTX injection in the TA muscle, and four days later, individual myofibers were isolated from the neighboring EDL muscle. Immunochemical labeling of cryosections, myofibers and cells were performed at previously reported (Kuang et al., 2006). The primary antibodies used are listed in Supplemental Table 1.

siRNA Knock-Down

For EDL myofibers, transfections were carried at 4 hours and 24 hours post-dissection in plating medium using Lipofectamine 2000 reagent (Invitrogen) as per manufacturer's instructions. Fibers were re-fed in fresh media on the next mornings and fixed after 42 hours to 72 hours of culture. For Satellite cell-derived myoblasts, cells were re-fed 3 hours prior to transfection and transfections were carried in growth medium. Cells were washed and re-fed with Ham's Complete media 6 hours following transfections. RNA was harvested 48 hours following transfection. siRNA duplexes were from Ambion siFzd7 (ID s66314), siVangl2 (ID s96802) and used at the final concentration of 10 nM each. Transfection efficiency was monitored using Cy3-labeled siRNA. Knock-down efficiency was assessed by real-time PCR (FIGS. 14A and 13K).

Real-Time PCR

RNA was isolated using the RNEasy kits (Qiagen) and subjected to on column DNase digestion as per manufacturers instructions. cDNA synthesis was performed using the Superscript III reverse transcriptase and random hexamer primers (Invitrogen). Real-Time PCR was carried out as previously described (Ishibashi et al., 2005). Transcript levels were normalized to GAPDH transcript levels. Relative fold change in expression was calculated using the ΔΔCT method (CT values <30). For relative transcript quantification, each cDNA sample was run on a 5-point standard curve as to assure a PCR efficiency of ≥95%. Wnt Signaling Pathway PCR Arrays were purchased from Superarray Bioscience Corporation (PAMM-043) and analysis was performed as per manufacturer' instructions. See Table 2 for primer sequences.

Statistical Analysis

A minimum of 3 and up to 5 replicates was done for experiments presented. Data are presented as standard error of the mean. Results were assessed for statistical significance using Student's T Test (Microsoft Excel) and differences were considered statistically significant at the p<0.05 level. Table 1 below lists antibodies used in carrying out the various experiments performed in connection with the present invention. Table 2 below lists PCR primers used in carrying out the various experiments performed in connection with the present invention.

Muscle Injury

For freeze-induced muscle regeneration, skin and fascia of anesthetized mice were opened and the TA muscles were subjected to three consecutive cycles of freezing-thawing by applying a liquid nitrogen-cooled metallic rod, and the wound closed by suture. For CTX-induced muscle regeneration, 25 ul of diluted cardiotoxin were directly injected into the TA muscle without opening of the skin.

In Vivo Electroporation

40 μg of plasmid DNA in 0.9% NaCl or 0.9% NaCl (saline) was injected directly into the left TA muscle of anesthetized mice, that had been exposed by an incision through the skin. Immediately after injection, electric stimulation was applied directly to the TA by a pulse generator (ECM 830, BTX) of 100-150 volts for 6 pulses, with a fixed duration of 20 ms and an interval of 200 ms using 5 mm needle electrodes (BTX). Experimental and contralateral TA muscles were isolated and embedded in OWNT7A5% Sucrose (Tissue-Tek) and frozen with isopentane cooled by cold nitrogen.

In Vivo Electroporation of MDX Mice

We electroporated mdx mice (3 month old, male, 3 animals per group) with either 40 ug of a vector containing the coding region of the Wnt7a protein connected to the sequence for an HA (hemagglutinin) epitope under control of the CMV promoter (pHANpuro-Wnt7a-HA) or the pSPORT6-lacZ vector (Invitrogen) as a control. The latter vector was also used to determine the efficiency of the electroporation. Electroporation was carried out as described by LeGrand et al. 2009, mice were sacrificed 2 weeks after electroporation. Electroporation was carried out using the tibialis anterior (TA) muscle. The plasmid used for electroporation was dissolved in 0.9% NaCl, the total volume per TA muscle was 40 ul. For the experiments only one TA was injected and electroporated, the other TA was used as a control.

Sections (14 um) of the TA muscle were stained for Pax7, a marker for all satellite cells, as well as myf5, a marker for committed progenitor cells. Cells which were stained positively for both marker proteins were counted as committed progenitor cells whereas cells only positive for Pax7 were counted as satellite stem cells.

Histology and Quantification

Transverse sections (8 μm) of experimental and contralateral muscles were cut with a cryostat (Leica CM1850). The entire TA muscles were sectioned, in order to compare experimental and contralateral muscles at the same level on serial sections (around 400 sections were obtained from each TA muscle). For LacZ reaction, cryosections were fixed with 0.1% gluteraldehyde and exposed to X-gal solution. For H&E and immonostaining, sections were fixed with 4% paraformaldehyde. For enumeration of fibers, pictures of laminin-stained cryosections were assembled and counted on Adobe Photoshop CS2. Quantification of myofibers caliber was performed with ImageJ. The satellite cell enumeration was performed on Photoshop, on pictures of Pax7 and Laminin co-immunostained cryosections taken in regenerated areas where all the fibers had centrally located nuclei. "Satellite Cell Content" represents the number of sublaminar Pax7+ve satellite cells normalized per fiber number, and to the contralateral leg.

Subtractive Hybridization

RNA samples (10 ng) from sorted YFP+ and YFP− satellite cells were amplified using the Super-SMART cDNA amplification kit (Clontech) following the protocols provided. 2 ug of representative cDNA from each sample were used to generate a subtractive library with the PCR-Select kit (Clontech) as per manufacturer' instructions. The amplified cDNA from sorted YFP− was used as "tester" and the amplified cDNA from sorted YFP+ was used as "driver". SSH products were cloned in pCR®2.1 vector using a TA cloning Kit (Invitrogen) and 200 clones from the SSH library were sequenced with nested primers using the ABI 3730 DNA Analyzers (Applied Biosystems), according to the manufacturers' protocols and manuals.

TABLE 1

| | Antibodies | | |
|---|---|---|---|
| | Dilution | Supplier | Catalog number |
| α7-Integrin | 1/200 | MBL International | K0046-3 |
| Active-β-Catenin | 1/500 | Millipore Corp | 05-665 |

TABLE 1-continued

| | Antibodies | | |
|---|---|---|---|
| | Dilution | Supplier | Catalog number |
| CD11b | 1/200 | eBiosciences | 12-0112 |
| CD144 | 1/200 | BD Biosciences | 555289 |
| CD31 | 1/200 | eBiosciences | 12-0451 |
| CD34 | 1/50 | BD Biosciences | 553732 |
| CD45 | 1/200 | eBiosciences | 12-0311 |
| Celsr2 | 1/200 | MBL International | LS-A1943 |
| CXCR4 | 1/100 | BD Biosciences | 551968 |
| Frizzled7 | 1/100 | R&D Systems | MAB-1981 |
| GFP | 1/500 | Invitrogen | A21311 |
| Laminin α2 | 1/200 | Alexis Biochemicals | ALX-804-190 |
| Myf5 | 1/50 | Santa Cruz Biotechnology Inc | sc-302 |
| MyoD | 1/50 | Santa Cruz Biotechnology Inc | sc-304 |
| Myogenin | 1/100 | Santa Cruz Biotechnology Inc | sc-578 |
| Myosin Heavy Chain | 1/20 | DSHB | MF20 |
| Pax7 | 1/10 | DSHB | PAX7 |
| Prickle1 | 1/100 | Abcam | Ab15577 |
| Sca1 | 1/202 | eBiosciences | 12-5981 |
| Syndecan4 | 1/5000 | Gift from Brad Olwin | |
| Vangl2 | 1/200 | Santa Cruz Biotechnology Inc | sc-46561 |
| Wnt7a | 1/100 | Santa Cruz Biotechnology Inc | sc-26360 |

TABLE 2

| PCR Primers | | | | |
|---|---|---|---|---|
| Primer | Sequence | Exon | Amplicon | SEQ ID NO |
| Axin2_F | AAGAGAAGCGACCCAGTCAA | 2 | 198 | 13 |
| Axin2_R | CTGCGATGCATCTCTCTCTG | 3 | | 14 |
| Celsr1_F | GGGGACTACTGCGAGACTGA | 2 | 177 | 15 |
| Celsr1_R | CCCGTTTTTGCATACTCCAC | 3 | | 16 |
| Celsr2_F | CCGAGGTGGACCTCTGTTAC | 2 | 186 | 17 |
| Celsr2_R | CCACCAACAGGTTGACACAG | 3 | | 18 |
| Celsr3_F | ATGACCCGGATGTCTCTGAC | 1 | 216 | 19 |
| Celsr3_R | ACTCCTCCGTGATGATGACC | 2 | | 20 |
| Dvl1_F | CTTACCAGGACCCTGGCTTC | 11 | 246 | 21 |
| Dvl1_R | CCTGACTTCGAGGGCTACTG | 12 | | 22 |
| Dvl2_F | TATGTCTTCGGGGACCTCAG | 13 | 212 | 23 |
| Dvl2_R | CGAAGAAAGCTCGTGGTAGG | 14 | | 24 |
| Dvl3_F | GCCTATGGCTTTCCCTTACC | 14 | 198 | 25 |
| Dvl3_R | ACTTGGAGTCCCCAGCTTTT | 15 | | 26 |
| Fzd1_F | CAAGGTTTACGGGCTCATGT | 1 | 180 | 27 |

TABLE 2-continued

PCR Primers

| Primer | Sequence | Exon | Amplicon | SEQ ID NO |
|---|---|---|---|---|
| Fzd1_R | GTAACAGCCGGACAGGAAAA | 1 | | 28 |
| Fzd3_F | CCTTGAGGATGTGCCAAGAT | 2 | 178 | 29 |
| Fzd3_R | GCTATAGGCACGCTGACACA | 3 | | 30 |
| Fzd4_F | AACCTCGGCTACAACGTGAC | 1 | 150 | 31 |
| Fzd4_R | TGGCACATAAACCGAACAAA | 2 | | 32 |
| Fzd6_F | AATGGACACTTTTGGCATCC | 3 | 223 | 33 |
| Fzd6_R | AGGGGCACACTGTTCAATTC | 4 | | 34 |
| Fzd7_F | GCTTCCTAGGTGAGCGTGAC | 1 | 216 | 35 |
| Fzd7_R | AACCCGACAGGAAGATGATG | 1 | | 36 |
| Gapdh_F | ATGCCAGTGAGCTTCCCGTC | 1 | 470 | 37 |
| Gapdh_R | CATCACCATCTTCCAGGAGC | 1 | | 38 |
| Myf5_F | TGAAGGATGGACATGACGGACG | 1 | 133 | 39 |
| Myf5_R | TTGTGTGCTCCGAAGGCTGCTA | 1 | | 40 |
| MyoD_F | TACCCAAGGTGGAGATCCTG | 1 | 200 | 41 |
| MyoD_R | CATCATGCCATCAGAGCAGT | 1 | | 42 |
| Myogenin_F | GAAAGTGAATGAGGCCTTCG | 1 | 248 | 43 |
| Myogenin_R | ACGATGGACGTAAGGGAGTG | 3 | | 44 |
| Notch3_F | GATGACACATCAGCCAGCAT | 32 | 248 | 45 |
| Notch3_R | GAGCGGTTCCTGATGAGAAT | 33 | | 46 |
| Pax7_F | CTGGATGAGGGCTCAGATGT | 3 | 245 | 47 |
| Pax7_R | GGTTAGCTCCTGCCTGCTTA | 4 | | 48 |
| Tcf7_F | CCCCAGCTTTCTCCACTCTA | 4 | 165 | 49 |
| Tcf7_R | TCACAGTATGGGGGAGCTGT | 5 | | 50 |
| Vangl1_F | GCACTACCACAGCATGGAGA | 7 | 235 | 51 |
| Vangl1_R | ATTGACCACGAGGCTGAAGT | 8 | | 52 |
| Vangl2_F | CCCCAGTTCACACTCAAGGT | 4 | 157 | 53 |
| Vangl2_R | ACTTGGGCAGGTTGAGGAG | 5 | | 54 |
| Yfp_F | GCACGACTTCTTCAAGTCCGCCATG CC | 1 | 263 | 55 |
| Yfp_R | GCGGATCTTGAAGTTCACCTTGATG CC | 1 | | 56 |

NON-PATENT REFERENCES

Anakwe, K., Robson, L., Hadley, J., Buxton, P., Church, V., Allen, S., Hartmann, C., Harfe, B., Nohno, T., Brown, A. M., et al. (2003). Wnt signalling regulates myogenic differentiation in the developing avian wing. Development 130, 3503-3514.

Bae, G. U., Gaio, U., Yang, Y. J., Lee, H. J., Kang, J. S., and Krauss, R. S. (2008). Regulation of myoblast motility and fusion by the CXCR4-associated sialomucin, CD164. J Biol Chem 283, 8301-8309.

Borello, U., Berarducci, B., Murphy, P., Bajard, L., Buffa, V., Piccolo, S., Buckingham, M., and Cossu, G. (2006). The Wnt/beta-catenin pathway regulates Gli-mediated Myf5 expression during somitogenesis. Development 133, 3723-3732.

Brack, A. S., Conboy, I. M., Conboy, M. J., Shen, J., and Rando, T. A. (2008). A temporal switch from notch to Wnt signaling in muscle stem cells is necessary for normal adult myogenesis. Cell Stem Cell 2, 50-59.

Cerletti, M., Jurga, S., Witczak, C. A., Hirshman, M. F., Shadrach, J. L., Goodyear, L. J., and Wagers, A. J. (2008).

Highly efficient, functional engraftment of skeletal muscle stem cells in dystrophic muscles. Cell 134, 37-47.

Charge, S. B., Brack, A. S., and Hughes, S. M. (2002). Aging-related satellite cell differentiation defect occurs prematurely after Ski-induced muscle hypertrophy. Am J Physiol Cell Physiol 283, C1228-1241.

Charge, S B., and Rudnicki, M. A. (2004). Cellular and molecular regulation of muscle regeneration. Physiol Rev 84, 209-238.

Chen, A. E., Ginty, D. D., and Fan, C. M. (2005). Protein kinase A signalling via CREB controls myogenesis induced by Wnt proteins. Nature 433, 317-322.

Ciruna, B., Jenny, A., Lee, D., Mlodzik, M., and Schier, A. F. (2006). Planar cell polarity signalling couples cell division and morphogenesis during neurulation. Nature 439, 220-224.

Clevers, H. (2006). Wnt/beta-catenin signaling in development and disease. Cell 127, 469-480.

Collins, C. A., Olsen, I., Zammit, P. S., Heslop, L., Petrie, A., Partridge, T. A., and Morgan, J. E. (2005). Stem cell function, self-renewal, and behavioral heterogeneity of cells from the adult muscle satellite cell niche. Cell 122, 289-301.

Cornelison, D. D., Filla, M. S., Stanley, H. M., Rapraeger, A. C., and Olwin, B. B. (2001). Syndecan-3 and syndecan-4 specifically mark skeletal muscle satellite cells and are implicated in satellite cell maintenance and muscle regeneration. Dev Biol 239, 79-94.

Cornelison, D. D., Wilcox-Adelman, S. A., Goetinck, P. F., Rauvala, H., Rapraeger, A. C., and Olwin, B. B. (2004). Essential and separable roles for Syndecan-3 and Syndecan-4 in skeletal muscle development and regeneration. Genes Dev 18, 2231-2236.

Cossu, G., and Borello, U. (1999). Wnt signaling and the activation of myogenesis in mammals. Embo J 18, 6867-6872.

Dann et al. Nature, 412, Jul. 5, 2001, p. 86-90 del Alamo, D., and Mlodzik, M. (2006). Frizzled/PCP-dependent asymmetric neutralized expression determines R3/R4 fates in the *Drosophila* eye. Dev Cell 11, 887-894.

Diatchenko, L., Lau, Y., Campbell, A., Chenchik, A., Moqadam, F., Huang, B., Lukyanov, S., Lukyanov, K., Gurskaya, N., Sverdlov, E., et al. (1997). Suppression subtractive hybridization: a method for generating differentially regulated or tissue-specific cDNA probes and libraries. Proc Natl Acad Sci USA 93, 6025-6030.

Egger-Adam, D., and Katanaev, V. L. (2008). Trimeric G protein-dependent signaling by Frizzled receptors in animal development. Front Biosci 13, 4740-4755.

Goto, T., Davidson, L., Asashima, M., and Keller, R. (2005). Planar cell polarity genes regulate polarized extracellular matrix deposition during frog gastrulation. Curr Biol 15, 787-793.

Gros, J., Serralbo, O., and Marcelle, C. (2009). WNT11 acts as a directional cue to organize the elongation of early muscle fibres. Nature 457, 589-593.

Hirabayashi, Y., Itoh, Y., Tabata, H., Nakajima, K., Akiyama, T., Masuyama, N., and Gotoh, Y. (2004). The Wnt/beta-catenin pathway directs neuronal differentiation of cortical neural precursor cells. Development 131, 2791-2801.

Ishibashi, J., Perry, R. L., Asakura, A., and Rudnicki, M. A. (2005). MyoD induces myogenic differentiation through cooperation of its NH2- and COOH-terminal regions. J Cell Biol 171, 471-482.

Kengaku, M., Capdevila, J., Rodriguez-Esteban, C., De La Pena, J., Johnson, R. L., Belmonte, J. C., and Tabin, C. J. (1998). Distinct WNT pathways regulating AER formation and dorsoventral polarity in the chick limb bud. Science 280, 1274-1277.

Kuang, S., Charge, S. B., Seale, P., Huh, M., and Rudnicki, M. A. (2006). Distinct roles for Pax7 and Pax3 in adult regenerative myogenesis. J Cell Biol 172, 103-113.

Kuang, S., Gillespie, M. A., and Rudnicki, M. A. (2008). Niche regulation of muscle satellite cell self-renewal and differentiation. Cell Stem Cell 2, 22-31.

Kuang, S., Kuroda, K., Le Grand, F., and Rudnicki, M. A. (2007). Asymmetric self-renewal and commitment of satellite stem cells in muscle. Cell 129, 999-1010.

Matthews, H. K., Marchant, L., Carmona-Fontaine, C., Kuriyama, S., Larrain, J., Holt, M. R., Parsons, M., and Mayor, R. (2008). Directional migration of neural crest cells in vivo is regulated by Syndecan-4/Rac1 and non-canonical Wnt signaling/RhoA. Development 135, 1771-1780.

McKinnell, I. W., Ishibashi, J., Le Grand, F., Punch, V. G., Addicks, G. C., Greenblatt, J. F., Dilworth, F. J., and Rudnicki, M. A. (2008). Pax7 activates myogenic genes by recruitment of a histone methyltransferase complex. Nat Cell Biol 10, 77-84.

Miller, C., and Sassoon, D. A. (1998). Wnt-7a maintains appropriate uterine patterning during the development of the mouse female reproductive tract. Development 125, 3201-3211.

Montarras, D., Morgan, J., Collins, C., Relaix, F., Zaffran, S., Cumano, A., Partridge, T., and Buckingham, M. (2005). Direct isolation of satellite cells for skeletal muscle regeneration. Science 309, 2064-2067.

Montcouquiol, M., Rachel, R. A., Lanford, P. J., Copeland, N. G., Jenkins, N. A., and Kelley, M. W. (2003). Identification of Vangl2 and Scrb1 as planar polarity genes in mammals. Nature 423, 173-177.

Montcouquiol, M., Sans, N., Huss, D., Kach, J., Dickman, J. D., Forge, A., Rachel, R. A., Copeland, N. G., Jenkins, N. A., Bogani, D., et al. (2006). Asymmetric localization of Vangl2 and Fz3 indicate novel mechanisms for planar cell polarity in mammals. J Neurosci 26, 5265-5275.

Munoz, R., Moreno, M., Oliva, C., Orbenes, C., and Larrain, J. (2006). Syndecan-4 regulates non-canonical Wnt signalling and is essential for convergent and extension movements in *Xenopus* embryos. Nat Cell Biol 8, 492-500.

Oustanina, S., Hause, G., and Braun, T. (2004). Pax7 directs postnatal renewal and propagation of myogenic satellite cells but not their specification. The EMBO journal 23, 3430-3439.

Park, M., and Moon, R. T. (2002). The planar cell-polarity gene stbm regulates cell behaviour and cell fate in vertebrate embryos. Nat Cell Biol 4, 20-25.

Polesskaya, A., Seale, P., and Rudnicki, M. A. (2003). Wnt signaling induces the myogenic specification of resident CD45+ adult stem cells during muscle regeneration. Cell 113, 841-852.

Rochat, A., Fernandez, A., Vandromme, M., Moles, J. P., Bouschet, T., Carnac, G., and Lamb, N. J. (2004). Insulin and wnt1 pathways cooperate to induce reserve cell activation in differentiation and myotube hypertrophy. Mol Biol Cell 15, 4544-4555.

Sacco, A., Doyonnas, R., Kraft, P., Vitorovic, S., and Blau, H. M. (2008). Self-renewal and expansion of single transplanted muscle stem cells. Nature 456, 502-506.

Seale, P., Sabourin, L. A., Girgis-Gabardo, A., Mansouri, A., Gruss, P., and Rudnicki, M. A. (2000). Pax7 is required for the specification of myogenic satellite cells. Cell 102, 777-786.

Seifert, J. R., and Mlodzik, M. (2007). Frizzled/PCP signalling: a conserved mechanism regulating cell polarity and directed motility. Nat Rev Genet 8, 126-138.

Srinivas, S., Watanabe, T., Lin, C. S., William, C. M., Tanabe, Y., Jessell, T. M., and Costantini, F. (2001). Cre reporter strains produced by targeted insertion of EYFP and ECFP into the ROSA26 locus. BMC Dev Biol 1, 4.

Tajbakhsh, S., Borello, U., Vivarelli, E., Kelly, R., Papkoff, J., Duprez, D., Buckingham, M., and Cossu, G. (1998). Differential activation of Myf5 and MyoD by different Wnts in explants of mouse paraxial mesoderm and the later activation of myogenesis in the absence of Myf5. Development 125, 4155-4162.

Tallquist, M. D., Weismann, K. E., Hellstrom, M., and Soriano, P. (2000). Early myotome specification regulates PDGFA expression and axial skeleton development. Development 127, 5059-5070.

Torban, E., Kor, C., and Gros, P. (2004). Van Gogh-like2 (Strabismus) and its role in planar cell polarity and convergent extension in vertebrates. Trends Genet 20, 570-577.

Torban, E., Patenaude, A. M., Leclerc, S., Rakowiecki, S., Gauthier, S., Andelfinger, G., Epstein, D. J., and Gros, P. (2008). Genetic interaction between members of the Vangl family causes neural tube defects in mice. Proc Natl Acad Sci USA 105, 3449-3454.

Torrente, Y., Belicchi, M., Sampaolesi, M., Pisati, F., Meregalli, M., D'Antona, G., Tonlorenzi, R., Porretti, L., Gavina, M., Mamchaoui, K., et al. (2004). Human circulating AC133(+) stem cells restore dystrophin expression and ameliorate function in dystrophic skeletal muscle. J Clin Invest 114, 182-195.

Zallen, J. A. (2007). Planar polarity and tissue morphogenesis. Cell 129, 1051-1063. All references cited are incorporated herein by reference in their entirety.

The above-described embodiments of the invention are intended to be examples only. Alterations, modifications and variations can be effected to the particular embodiments by those of skill in the art without departing from the scope of the invention, which is defined solely by the claims appended hereto.

The invention claimed is:

1. A method for modulating division symmetry of satellite stem cells comprising contacting isolated satellite stem cells with a composition comprising as an active agent a Wnt7a polypeptide or an active variant thereof having at least 95% identity to SEQ ID NO:2 or SEQ ID NO:4 and capable of binding to and activating Fzd7.

2. A method for increasing the number of satellite stem cells in a skeletal muscle in a subject in need thereof comprising contacting isolated satellite stem cells with a composition comprising as an active agent a Wnt7a polypeptide or an active variant thereof having at least 95% identity to SEQ ID NO:2 or SEQ ID NO:4 and capable of binding to and activating Fzd7, and administering the satellite stem cells to the skeletal muscle.

3. The method of claim 2, wherein the subject has a degenerative disease.

4. The method of claim 3, wherein the degenerative disease is a muscular dystrophy.

5. The method of claim 4, wherein the muscle dystrophy is muscular dystrophy selected from the group consisting of Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

6. The method of claim 2, wherein the subject suffers from muscle wasting or atrophy associated with injury or illness.

7. A method for expanding a population of satellite stem cells comprising isolating satellite stem cells and contacting the isolated satellite stem cells with an effective amount of a composition comprising a Wnt7a polypeptide or an active variant thereof having at least 95% identity to SEQ ID NO:2 or SEQ ID NO:4 and capable of binding to and activating Fzd7.

* * * * *